US009636303B2

(12) United States Patent
Barnscheid et al.

(10) Patent No.: US 9,636,303 B2
(45) Date of Patent: May 2, 2017

(54) TAMPER RESISTANT DOSAGE FORM COMPRISING AN ANIONIC POLYMER

(75) Inventors: Lutz Barnscheid, Mönchengladbach (DE); Sebastian Schwier, Grevenbroich (DE); Johannes Bartholomäus, Aachen (DE)

(73) Assignee: GRUENENTHAL GMBH, Aachen (DE)

( * ) Notice: Subject to any disclaimer, the term of this patent is extended or adjusted under 35 U.S.C. 154(b) by 286 days.

(21) Appl. No.: 13/223,384

(22) Filed: Sep. 1, 2011

(65) Prior Publication Data
US 2012/0065220 A1 Mar. 15, 2012

Related U.S. Application Data

(60) Provisional application No. 61/379,507, filed on Sep. 2, 2010.

(30) Foreign Application Priority Data

Sep. 2, 2010 (EP) ..................... 10009125

(51) Int. Cl.
| A61K 31/485 | (2006.01) |
| A61K 31/135 | (2006.01) |
| A61P 25/04 | (2006.01) |
| A61K 47/34 | (2006.01) |
| A61K 9/20 | (2006.01) |
| A61K 31/137 | (2006.01) |

(52) U.S. Cl.
CPC .......... *A61K 9/2031* (2013.01); *A61K 9/2095* (2013.01); *A61K 31/137* (2013.01); *A61K 9/2013* (2013.01); *A61K 9/2027* (2013.01); *A61K 9/2054* (2013.01)

(58) Field of Classification Search
None
See application file for complete search history.

(56) References Cited

U.S. PATENT DOCUMENTS

| 2,524,855 | A | 10/1950 | Schnider et al. |
| 2,806,033 | A | 9/1957 | Lewenstein et al. |
| 2,987,445 | A | 6/1961 | Levesque |
| 3,332,950 | A | 7/1967 | Blumberg et al. |
| 3,370,035 | A | 2/1968 | Ogura et al. |
| 3,652,589 | A | 3/1972 | Flick et al. |
| 3,806,603 | A | 4/1974 | Gaunt et al. |
| 3,865,108 | A | 2/1975 | Hartop |
| 3,941,865 | A | 3/1976 | Miller et al. |
| 3,966,747 | A | 6/1976 | Monkovic et al. |
| 3,980,766 | A | 9/1976 | Shaw et al. |
| 4,002,173 | A | 1/1977 | Manning et al. |
| 4,014,965 | A | 3/1977 | Stube et al. |
| 4,070,494 | A | 1/1978 | Hoffmeister et al. |
| 4,070,497 | A | 1/1978 | Wismer et al. |
| 4,175,119 | A | 11/1979 | Porter |
| 4,200,704 | A | 4/1980 | Stanley et al. |
| 4,207,893 | A | 6/1980 | Michaels |
| 4,262,017 | A | 4/1981 | Kuipers |
| 4,343,789 | A | 8/1982 | Kawata et al. |
| 4,353,887 | A | 10/1982 | Hess et al. |
| 4,404,183 | A | 9/1983 | Kawata et al. |
| 4,427,681 | A | 1/1984 | Munshi et al. |
| 4,427,778 | A | 1/1984 | Zabriskie |
| 4,457,933 | A | 7/1984 | Gordon et al. |
| 4,462,941 | A | 7/1984 | Lee et al. |
| 4,473,640 | A | 9/1984 | Combie et al. |
| 4,483,847 | A | 11/1984 | Augart |
| 4,485,211 | A | 11/1984 | Okamoto |
| 4,529,583 | A | 7/1985 | Porter |
| 4,599,342 | A | 7/1986 | La Hann |
| 4,603,143 | A | 7/1986 | Schmidt |
| 4,612,008 | A | 9/1986 | Wong et al. |
| 4,629,621 | A | 12/1986 | Snipes |

(Continued)

FOREIGN PATENT DOCUMENTS

| AR | 46994 A1 | 12/2004 |
| AR | 045353 A1 | 10/2005 |

(Continued)

OTHER PUBLICATIONS

"Polyox water soluble resins" 2003. http://www.dow.com/webapps/lit/litorder.asp?filepath=polyox/pdfs/noreg/326-00002.pdf.*
Bauer et al. Lehrbuch der Pharmazeutischen Technologie. Eight Edition 2006. Stuttgart, pp. 343-352.
Hartauer, Pharma. Dev. & Tech, 5 (3) 303-310 (2000).
Marques, Tablet breaking force, 2008.
Ritschel et al. Die Tablette: Handbuch der Entwicklung, Herstellung und Qualitatssicherung, 2nd Edition, 2002. Ch 6, pp. 69-82 and 115-136.
Ritschel et al. Die Tablette: Handbuch der Entwicklung, Herstellung und Qualitatssiehcrung 2nd Edition, 2002, Table of content.
Wagner, Pharmazeutische Biologie—Drogen und ihre Inhaltsstoffe—Scharfstoffdrogen. 2nd., revised edition, Gustav Fischer Verlag, Stuttgart-N.Y., 1982, Table of Content.

(Continued)

*Primary Examiner* — Robert A Wax
*Assistant Examiner* — Danah Al-Awadi
(74) *Attorney, Agent, or Firm* — Norris McLaughlin & Marcus, P.A.

(57) ABSTRACT

A pharmaceutical dosage form and method of using same, the pharmaceutical dosage form exhibiting a breaking strength of at least 500 N, said dosage form containing
 a pharmacologically active ingredient (A);
 a physiologically acceptable polymer (B) obtainable by polymerization of a monomer composition comprising an ethylenically unsaturated monomer bearing an anionic functional group, in protonated form or a physiologically acceptable salt thereof;
 a polyalkylene oxide (C) having a weight average molecular weight of at least 200,000 g/mol, wherein the content of the polyalkylene oxide (C) is at least 20 wt.-%, based on the total weight of the dosage form;
wherein the pharmacologically active ingredient (A) is present in a controlled-release matrix comprising the polymer (B) and the polyalkylene oxide (C).

10 Claims, 17 Drawing Sheets

(56) References Cited

U.S. PATENT DOCUMENTS

| | | |
|---|---|---|
| 4,667,013 A | 5/1987 | Reichle |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keith et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk et al. |
| 4,940,556 A | 7/1990 | MacFarlane et al. |
| 4,957,668 A | 9/1990 | Placard |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Graudums et al. |
| 5,811,126 A | 9/1998 | Krishanmurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merrill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 * | 6/2003 | Guo .................... 424/468 |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |

(56) References Cited

U.S. PATENT DOCUMENTS

| | | | |
|---|---|---|---|
| 8,101,630 B2* | 1/2012 | Kumar et al. | 514/282 |
| 8,114,383 B2 | 2/2012 | Bartholomaus et al. | |
| 8,114,384 B2 | 2/2012 | Arkenau et al. | |
| 8,114,838 B2 | 2/2012 | Marchionni | |
| 8,192,722 B2 | 6/2012 | Arkenau-Maric et al. | |
| 8,202,542 B1 | 6/2012 | Mehta et al. | |
| 8,309,060 B2 | 11/2012 | Bartholomeus et al. | |
| 8,309,122 B2 | 11/2012 | Kao et al. | |
| 8,323,889 B2 | 12/2012 | Arkenau-Maric et al. | |
| 8,329,216 B2 | 12/2012 | Kao et al. | |
| 8,337,888 B2 | 12/2012 | Wright et al. | |
| 8,383,152 B2 | 2/2013 | Jans et al. | |
| 8,420,056 B2 | 4/2013 | Arkenau-Maric et al. | |
| 8,445,023 B2* | 5/2013 | Guimberteau et al. | 424/490 |
| 8,722,086 B2 | 5/2014 | Arkenau-Marie et al. | |
| 8,858,963 B1 | 10/2014 | Devarakonda et al. | |
| 9,192,578 B2 | 11/2015 | McGinity et al. | |
| 2001/0038852 A1 | 11/2001 | Kolter et al. | |
| 2002/0012701 A1 | 1/2002 | Kolter et al. | |
| 2002/0015730 A1 | 2/2002 | Hoffmann et al. | |
| 2002/0051820 A1 | 5/2002 | Shell et al. | |
| 2002/0114838 A1 | 8/2002 | Ayer et al. | |
| 2002/0132359 A1 | 9/2002 | Waterman | |
| 2002/0132395 A1 | 9/2002 | Iyer et al. | |
| 2002/0176888 A1 | 11/2002 | Bartholomaeus et al. | |
| 2002/0187192 A1 | 12/2002 | Joshi et al. | |
| 2002/0192277 A1 | 12/2002 | Oshlack et al. | |
| 2003/0008409 A1 | 1/2003 | Spearman et al. | |
| 2003/0015814 A1 | 1/2003 | Krull et al. | |
| 2003/0017532 A1 | 1/2003 | Biswas et al. | |
| 2003/0021546 A1 | 1/2003 | Sato | |
| 2003/0031546 A1 | 2/2003 | Araki et al. | |
| 2003/0044458 A1 | 3/2003 | Wright et al. | |
| 2003/0044464 A1 | 3/2003 | Zeigler et al. | |
| 2003/0064099 A1 | 4/2003 | Oshlack et al. | |
| 2003/0068276 A1 | 4/2003 | Hughes et al. | |
| 2003/0068370 A1 | 4/2003 | Sackler et al. | |
| 2003/0068371 A1 | 4/2003 | Oshlack et al. | |
| 2003/0068375 A1 | 4/2003 | Wright et al. | |
| 2003/0068392 A1 | 4/2003 | Sackler | |
| 2003/0069263 A1 | 4/2003 | Breder et al. | |
| 2003/0077297 A1 | 4/2003 | Chen et al. | |
| 2003/0091630 A1 | 5/2003 | Louie-Helm et al. | |
| 2003/0092724 A1 | 5/2003 | Kao et al. | |
| 2003/0104052 A1 | 6/2003 | Berner et al. | |
| 2003/0104053 A1 | 6/2003 | Gusler et al. | |
| 2003/0118641 A1 | 6/2003 | Maloney et al. | |
| 2003/0124185 A1 | 7/2003 | Oshlack et al. | |
| 2003/0125347 A1 | 7/2003 | Anderson et al. | |
| 2003/0129230 A1 | 7/2003 | Baichwal et al. | |
| 2003/0133985 A1 | 7/2003 | Louie-Helm et al. | |
| 2003/0143269 A1 | 7/2003 | Oshlack et al. | |
| 2003/0152622 A1 | 8/2003 | Louie-Helm et al. | |
| 2003/0158242 A1 | 8/2003 | Kugelmann | |
| 2003/0175326 A1 | 9/2003 | Thombre | |
| 2003/0198677 A1 | 10/2003 | Pryce Lewis et al. | |
| 2003/0215508 A1 | 11/2003 | Davis et al. | |
| 2003/0232895 A1 | 12/2003 | Omidian et al. | |
| 2004/0010000 A1 | 1/2004 | Ayer et al. | |
| 2004/0011806 A1 | 1/2004 | Luciano et al. | |
| 2004/0052731 A1 | 3/2004 | Hirsh et al. | |
| 2004/0052844 A1 | 3/2004 | Hsiao et al. | |
| 2004/0081694 A1 | 4/2004 | Oshlack et al. | |
| 2004/0091528 A1 | 5/2004 | Rogers et al. | |
| 2004/0126428 A1 | 7/2004 | Hughes et al. | |
| 2004/0131671 A1 | 7/2004 | Zhang et al. | |
| 2004/0156899 A1 | 8/2004 | Louie-Helm et al. | |
| 2004/0170567 A1 | 9/2004 | Sackler | |
| 2004/0185105 A1 | 9/2004 | Berner et al. | |
| 2004/0213845 A1 | 10/2004 | Sugihara | |
| 2004/0213848 A1 | 10/2004 | Li et al. | |
| 2005/0015730 A1 | 1/2005 | Gunturi et al. | |
| 2005/0031546 A1* | 2/2005 | Bartholomaus et al. | 424/10.1 |
| 2005/0058706 A1 | 3/2005 | Bartholomaeus et al. | |
| 2005/0063214 A1 | 3/2005 | Takashima | |
| 2005/0089475 A1 | 4/2005 | Gruber | |
| 2005/0089569 A1 | 4/2005 | Bar-Shalom | |
| 2005/0095291 A1 | 5/2005 | Oshlack et al. | |
| 2005/0106249 A1 | 5/2005 | Hwang et al. | |
| 2005/0112067 A1 | 5/2005 | Kumar et al. | |
| 2005/0127555 A1 | 6/2005 | Gusik et al. | |
| 2005/0152843 A1 | 7/2005 | Bartholomaeus et al. | |
| 2005/0181046 A1 | 8/2005 | Oshlack et al. | |
| 2005/0186139 A1 | 8/2005 | Bartholomaeus et al. | |
| 2005/0191244 A1 | 9/2005 | Bartholomaeus et al. | |
| 2005/0192333 A1 | 9/2005 | Hinze et al. | |
| 2005/0214223 A1 | 9/2005 | Bartholomaeus et al. | |
| 2005/0220877 A1 | 10/2005 | Patel | |
| 2005/0222188 A1 | 10/2005 | Chapman et al. | |
| 2005/0236741 A1 | 10/2005 | Arkenau et al. | |
| 2005/0245556 A1 | 11/2005 | Brogmann et al. | |
| 2005/0266084 A1 | 12/2005 | Li et al. | |
| 2006/0002859 A1 | 1/2006 | Arkenau et al. | |
| 2006/0002860 A1 | 1/2006 | Bartholomaus et al. | |
| 2006/0004034 A1 | 1/2006 | Hinze et al. | |
| 2006/0009478 A1 | 1/2006 | Friedmann et al. | |
| 2006/0012701 A1 | 1/2006 | Hong | |
| 2006/0017916 A1 | 1/2006 | Clarke et al. | |
| 2006/0039864 A1 | 2/2006 | Bartholomaus et al. | |
| 2006/0073102 A1 | 4/2006 | Huaihung et al. | |
| 2006/0099250 A1 | 5/2006 | Tian et al. | |
| 2006/0104909 A1 | 5/2006 | Vaghefi | |
| 2006/0182801 A1 | 8/2006 | Breder et al. | |
| 2006/0188447 A1 | 8/2006 | Arkenau-Maric et al. | |
| 2006/0193782 A1 | 8/2006 | Bartholomaus et al. | |
| 2006/0193914 A1 | 8/2006 | Ashworth et al. | |
| 2006/0194759 A1 | 8/2006 | Eidelson | |
| 2006/0194826 A1 | 8/2006 | Oshlack et al. | |
| 2006/0240105 A1 | 10/2006 | Devane et al. | |
| 2006/0240110 A1 | 10/2006 | Kiick et al. | |
| 2006/0269603 A1 | 11/2006 | Brown Miller et al. | |
| 2007/0003616 A1 | 1/2007 | Arkenau-Maric et al. | |
| 2007/0003617 A1 | 1/2007 | Fischer et al. | |
| 2007/0020188 A1 | 1/2007 | Sackler | |
| 2007/0020335 A1 | 1/2007 | Chen et al. | |
| 2007/0042044 A1 | 2/2007 | Fischer et al. | |
| 2007/0048228 A1 | 3/2007 | Arkenau-Maric et al. | |
| 2007/0065365 A1 | 3/2007 | Kugelmann et al. | |
| 2007/0092573 A1 | 4/2007 | Joshi et al. | |
| 2007/0183979 A1* | 8/2007 | Arkenau-Maric et al. | 424/10.2 |
| 2007/0183980 A1 | 8/2007 | Arkenau-Maric et al. | |
| 2007/0184117 A1 | 8/2007 | Gregory et al. | |
| 2007/0190142 A1 | 8/2007 | Breitenbach et al. | |
| 2007/0196396 A1 | 8/2007 | Pilgaonkar et al. | |
| 2007/0196481 A1 | 8/2007 | Amidon et al. | |
| 2007/0224129 A1* | 9/2007 | Guimberteau et al. | 424/10.2 |
| 2007/0231268 A1 | 10/2007 | Emigh et al. | |
| 2007/0259045 A1 | 11/2007 | Mannion et al. | |
| 2007/0264327 A1 | 11/2007 | Kumar et al. | |
| 2007/0269505 A1 | 11/2007 | Flath et al. | |
| 2007/0292508 A1 | 12/2007 | Szamosi et al. | |
| 2008/0020032 A1 | 1/2008 | Crowley et al. | |
| 2008/0023452 A1 | 1/2008 | Grek et al. | |
| 2008/0063725 A1 | 3/2008 | Guimberteau et al. | |
| 2008/0069871 A1 | 3/2008 | Vaughn et al. | |
| 2008/0075669 A1 | 3/2008 | Soscia et al. | |
| 2008/0075768 A1 | 3/2008 | Vaughn et al. | |
| 2008/0081290 A1 | 4/2008 | Wada et al. | |
| 2008/0085304 A1 | 4/2008 | Baichwal et al. | |
| 2008/0145429 A1 | 6/2008 | Leyenecker et al. | |
| 2008/0152595 A1 | 6/2008 | Emigh et al. | |
| 2008/0181932 A1 | 7/2008 | Bortz et al. | |
| 2008/0220079 A1 | 9/2008 | Chen | |
| 2008/0234352 A1 | 9/2008 | Fischer et al. | |
| 2008/0247959 A1 | 10/2008 | Bartholomaus et al. | |
| 2008/0248113 A1 | 10/2008 | Bartholomaus et al. | |
| 2008/0280975 A1 | 11/2008 | Badul | |
| 2008/0311049 A1 | 12/2008 | Arkenau-Maric et al. | |
| 2008/0311187 A1 | 12/2008 | Ashworth et al. | |
| 2008/0311197 A1 | 12/2008 | Arkenau-Maric et al. | |
| 2008/0311205 A1 | 12/2008 | Habib et al. | |
| 2008/0312264 A1 | 12/2008 | Arkenau-Maric et al. | |
| 2008/0317695 A1 | 12/2008 | Everaert et al. | |
| 2008/0317854 A1 | 12/2008 | Arkenau et al. | |

(56) References Cited

U.S. PATENT DOCUMENTS

| | | |
|---|---|---|
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | KcKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Andersen et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Fauer et al. |
| 2011/0092515 A1 | 4/2011 | Qiu et al. |
| 2011/0097404 A1 | 4/2011 | Oshlack et al. |
| 2011/0159100 A1 | 6/2011 | Anderson et al. |
| 2011/0187017 A1 | 8/2011 | Haupts |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholom us et al. |
| 2012/0108622 A1 | 5/2012 | Wright et al. |
| 2012/0135071 A1 | 5/2012 | Bartholom us et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Geibler et al. |
| 2013/0129825 A1 | 5/2013 | Billoet et al. |
| 2013/0129826 A1 | 5/2013 | Geibler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau-Maric et al. |
| 2014/0112989 A1 | 4/2014 | Bartholomäus et al. |
| 2014/0170079 A1 | 6/2014 | Arkenau Maric et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0256456 A1 | 9/2016 | Caruso et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006/210145 B2 | 8/2006 |
| AU | 2006210145 A1 | 8/2006 |
| AU | 2009207796 A1 | 7/2009 |
| AU | 2009243681 A1 | 11/2009 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 | 5/1993 |
| CA | 2577233 A1 | 10/1997 |
| CA | 2650637 A1 | 10/1997 |
| CA | 2317747 A1 | 7/1999 |
| CA | 2343234 A1 | 3/2000 |
| CA | 2352874 | 6/2000 |
| CA | 2414349 A1 | 1/2002 |
| CA | 2456322 A1 | 2/2003 |
| CA | 2502965 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 001863513 A | 11/2006 |
| CN | 001863514 A | 11/2006 |
| CN | 01917862 A | 2/2007 |
| CN | 1942174 A | 4/2007 |

(56) References Cited

FOREIGN PATENT DOCUMENTS

| | | |
|---|---|---|
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |
| DE | 2530563 | 1/1977 |
| DE | 4229085 | 3/1994 |
| DE | 4309528 | 9/1994 |
| DE | 4446470 | 6/1996 |
| DE | 69400215 | 10/1996 |
| DE | 19522899 C1 | 12/1996 |
| DE | 2808505 A1 | 1/1997 |
| DE | 19753534 | 6/1999 |
| DE | 19800689 C1 | 7/1999 |
| DE | 19800698 | 7/1999 |
| DE | 19822979 | 12/1999 |
| DE | 69229881 T2 | 12/1999 |
| DE | 19855440 | 6/2000 |
| DE | 19856147 A1 | 6/2000 |
| DE | 19940740 A1 | 3/2001 |
| DE | 19960494 | 6/2001 |
| DE | 10036400 | 6/2002 |
| DE | 69429710 | 8/2002 |
| DE | 10250083 | 12/2003 |
| DE | 10250084 | 5/2004 |
| DE | 10250087 A1 | 5/2004 |
| DE | 10250088 A1 | 5/2004 |
| DE | 10336400 | 3/2005 |
| DE | 10361596 | 9/2005 |
| DE | 102004019916 A1 | 11/2005 |
| DE | 102004020220 A1 | 11/2005 |
| DE | 10 2004 032049 A1 | 1/2006 |
| DE | 10 2004 032051 A1 | 1/2006 |
| DE | 10 2004 032103 A1 | 1/2006 |
| DE | 10 2005 005446 A1 | 8/2006 |
| DE | 10 2005 005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0216453 B1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A1 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0293066 B1 | 11/1988 |
| EP | 0328775 A1 | 8/1989 |
| EP | 0228417 B1 | 8/1990 |
| EP | 0477135 A1 | 3/1992 |
| EP | 0277289 B1 | 4/1992 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0598606 B1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0661045 B1 | 7/1995 |
| EP | 0675710 A1 | 10/1995 |
| EP | 0675710 B1 | 10/1995 |
| EP | 0682945 A2 | 11/1995 |
| EP | 0693475 | 1/1996 |
| EP | 0820693 A1 | 1/1996 |
| EP | 0696598 A1 | 2/1996 |
| EP | 0583726 B1 | 11/1996 |
| EP | 0756480 A1 | 2/1997 |
| EP | 0760654 A1 | 3/1997 |
| EP | 0780369 | 6/1997 |
| EP | 0785775 A1 | 7/1997 |
| EP | 0761211 | 12/1997 |
| EP | 0809488 A1 | 12/1997 |
| EP | 0820698 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0980894 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1127871 B1 | 8/2001 |
| EP | 1138321 A2 | 10/2001 |
| EP | 1152026 A1 | 11/2001 |
| EP | 1166776 A2 | 1/2002 |
| EP | 1201233 A1 | 5/2002 |
| EP | 1250045 | 10/2002 |
| EP | 1250045 A2 | 10/2002 |
| EP | 1251120 A1 | 10/2002 |
| EP | 1293127 | 3/2003 |
| EP | 1293195 A1 | 3/2003 |
| EP | 1293196 A2 | 3/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 A1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |

(56) References Cited

FOREIGN PATENT DOCUMENTS

| | | | |
|---|---|---|---|
| GB | 2238478 A | 6/1991 |
| HR | P20070272 T3 | 6/2007 |
| HR | 20070456 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 3 0501737 A | 4/1991 |
| JP | H06507645 A | 9/1994 |
| JP | 08053331 A | 2/1996 |
| JP | 8 505076 A | 6/1996 |
| JP | H09508410 A | 8/1997 |
| JP | H1057450 A | 3/1998 |
| JP | 2002524150 A | 8/2002 |
| JP | 2002 275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 | 8/2010 |
| MX | 2010012039 A | 11/2010 |
| NO | 20061054 | 3/2006 |
| NO | 20070578 A | 1/2007 |
| NO | 20074412 A | 11/2007 |
| NZ | 528302 A | 2/2007 |
| PT | 1699440 | 12/2004 |
| PT | 1658054 E | 5/2006 |
| PT | 1658055 E | 7/2007 |
| PT | 1515702 | 12/2008 |
| RU | 2131244 | 6/1999 |
| RU | 2198197 C2 | 2/2003 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | I254634 B | 5/2006 |
| WO | WO 80/00841 A1 | 5/1980 |
| WO | 89/05624 A1 | 6/1989 |
| WO | 90/03776 | 4/1990 |
| WO | 93/06723 | 4/1993 |
| WO | 93/10758 | 6/1993 |
| WO | 93/11749 | 6/1993 |
| WO | WO 93/10765 A1 | 6/1993 |
| WO | 93/23017 A1 | 11/1993 |
| WO | 94/06414 | 3/1994 |
| WO | 94/08567 | 4/1994 |
| WO | 95/17174 | 6/1995 |
| WO | 95/20947 | 8/1995 |
| WO | 95/22319 | 8/1995 |
| WO | WO 95/20947 A1 | 8/1995 |
| WO | 95/30422 | 11/1995 |
| WO | 96/00066 | 1/1996 |
| WO | 96/03979 | 2/1996 |
| WO | 96/14058 | 5/1996 |
| WO | WO 97/00673 | 1/1997 |
| WO | 97/33566 | 9/1997 |
| WO | WO 97/49384 A1 | 12/1997 |
| WO | WO 98/35655 A3 | 2/1998 |
| WO | 98/20073 A2 | 5/1998 |
| WO | 98/28698 | 7/1998 |
| WO | 98/35655 | 8/1998 |
| WO | WO 98/51758 A1 | 11/1998 |
| WO | 99/12864 | 3/1999 |
| WO | 99/32120 | 7/1999 |
| WO | 99/44591 | 9/1999 |
| WO | 99/48481 A1 | 9/1999 |
| WO | WO99/45887 A2 | 9/1999 |
| WO | WO 00/13647 A1 | 3/2000 |
| WO | 00/33835 | 6/2000 |
| WO | 00/40205 A2 | 7/2000 |
| WO | 01/08661 A2 | 2/2001 |
| WO | 01/12230 | 2/2001 |
| WO | 01/15667 A1 | 3/2001 |
| WO | 01/52651 A2 | 7/2001 |
| WO | WO 01/58451 | 8/2001 |
| WO | WO 01/58451 A1 | 8/2001 |
| WO | 01/97783 A1 | 12/2001 |
| WO | 02/26061 | 4/2002 |
| WO | 02/26262 | 4/2002 |
| WO | 02/26928 | 4/2002 |
| WO | 0235991 A2 | 5/2002 |
| WO | WO 02/071860 A1 | 9/2002 |
| WO | 02/088217 | 11/2002 |
| WO | WO 02/094254 A2 | 11/2002 |
| WO | 03/006723 | 1/2003 |
| WO | 03/013476 A1 | 2/2003 |
| WO | 03/013479 A1 | 2/2003 |
| WO | 03/015531 | 2/2003 |
| WO | WO 03/013433 A2 | 2/2003 |
| WO | WO 03/013538 | 2/2003 |
| WO | WO 03/013538 A1 | 2/2003 |
| WO | 03/024430 A1 | 3/2003 |
| WO | 03024426 A1 | 3/2003 |
| WO | WO 03/018015 A1 | 3/2003 |
| WO | 03/026624 | 4/2003 |
| WO | 03/026743 A2 | 4/2003 |
| WO | 03/028698 | 4/2003 |
| WO | 03/028990 | 4/2003 |
| WO | 03/031546 A1 | 4/2003 |
| WO | 03/035029 | 5/2003 |
| WO | 03/035053 A1 | 5/2003 |
| WO | 03/035054 A1 | 5/2003 |
| WO | 03/035177 | 5/2003 |
| WO | WO 03/039561 A1 | 5/2003 |
| WO | WO 03/049689 A2 | 6/2003 |
| WO | 03/053417 A2 | 7/2003 |
| WO | 03/068392 A1 | 8/2003 |
| WO | WO 03/070191 A1 | 8/2003 |
| WO | 03/092648 | 11/2003 |
| WO | 03/094812 A1 | 11/2003 |
| WO | 03/105808 A1 | 12/2003 |
| WO | 2004/004693 A1 | 1/2004 |
| WO | 2004/043967 A1 | 2/2004 |
| WO | 2004/026262 | 4/2004 |
| WO | 2004/026263 | 4/2004 |
| WO | WO 2004/026280 A2 | 4/2004 |
| WO | 2004/037230 | 5/2004 |
| WO | 2004/037259 | 5/2004 |
| WO | 2004/037260 | 5/2004 |
| WO | 2004/066910 | 8/2004 |

(56) References Cited

FOREIGN PATENT DOCUMENTS

| | | |
|---|---|---|
| WO | WO 2004/078212 | 9/2004 |
| WO | 2004/084869 | 10/2004 |
| WO | 2004/093801 | 11/2004 |
| WO | 2004/093819 | 11/2004 |
| WO | 2004/100894 | 11/2004 |
| WO | WO 2004/098567 A2 | 11/2004 |
| WO | 2005/016313 | 2/2005 |
| WO | 2005/016314 | 2/2005 |
| WO | 2005/032524 | 4/2005 |
| WO | 2005/041968 | 5/2005 |
| WO | 2005/053656 | 6/2005 |
| WO | 2005/055981 | 6/2005 |
| WO | 2005053587 A1 | 6/2005 |
| WO | 2005/063214 | 7/2005 |
| WO | 2005/065646 | 7/2005 |
| WO | 2005/066183 A1 | 7/2005 |
| WO | WO 2005/060942 A1 | 7/2005 |
| WO | WO 2005/079760 A1 | 9/2005 |
| WO | 2005/102286 | 11/2005 |
| WO | WO 2005/102286 A1 | 11/2005 |
| WO | WO 2005/102294 A2 | 11/2005 |
| WO | WO 2005/105036 A1 | 11/2005 |
| WO | 2006/002883 | 1/2006 |
| WO | 2006/002884 | 1/2006 |
| WO | 2006/002886 | 1/2006 |
| WO | WO 2006/002884 B1 | 1/2006 |
| WO | WO 2006/039692 A2 | 4/2006 |
| WO | 2005102294 A3 | 5/2006 |
| WO | 2006058249 A2 | 6/2006 |
| WO | 2006/082097 | 8/2006 |
| WO | 2006/082099 | 8/2006 |
| WO | WO 2006/105615 A1 | 10/2006 |
| WO | WO 2006/128471 A2 | 12/2006 |
| WO | 2007/005716 | 1/2007 |
| WO | 2007/008752 | 1/2007 |
| WO | WO 2007/014061 A2 | 2/2007 |
| WO | 2007/048233 | 5/2007 |
| WO | 2007/053698 | 5/2007 |
| WO | 2007/085024 | 7/2007 |
| WO | WO 2007/085024 A3 | 7/2007 |
| WO | 2007103286 | 9/2007 |
| WO | WO 2007/103105 A2 | 9/2007 |
| WO | 2007/112285 | 10/2007 |
| WO | WO 2007/112273 A2 | 10/2007 |
| WO | WO 2007/112286 A2 | 10/2007 |
| WO | WO 2007/131357 A1 | 11/2007 |
| WO | WO 2008/023261 A1 | 2/2008 |
| WO | 2008033523 A1 | 3/2008 |
| WO | WO 2008/069941 A2 | 6/2008 |
| WO | 2008/086804 | 7/2008 |
| WO | 2008/107149 | 9/2008 |
| WO | WO 2008/107149 A3 | 9/2008 |
| WO | WO 2008/109462 A2 | 9/2008 |
| WO | WO2008/132707 A1 | 11/2008 |
| WO | WO 2008/142627 A2 | 11/2008 |
| WO | 2008/148798 | 12/2008 |
| WO | 2009/003776 A1 | 1/2009 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | 2009/092601 | 7/2009 |
| WO | 2009092601 A1 | 7/2009 |
| WO | WO 2009/110005 A2 | 9/2009 |
| WO | WO 2009/112273 A2 | 9/2009 |
| WO | 2009135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/0088911 A1 | 8/2010 |
| WO | WO 2010/105672 A1 | 9/2010 |
| WO | 2010140007 A2 | 12/2010 |
| WO | 2010140007 A9 | 12/2010 |
| WO | WO 2010/140007 A9 | 12/2010 |
| WO | WO 2010/149169 A2 | 12/2010 |
| WO | 2011009602 A1 | 1/2011 |
| WO | 2011009603 A1 | 1/2011 |
| WO | 2011009604 A1 | 1/2011 |
| WO | WO 2011/008298 A2 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 | 7/2015 |

OTHER PUBLICATIONS

Zeeshan, F and N. Bukhari, "Development and Evaluation of a Novel Modified-Release Pellet-Based Tablet System for the Delivery of Loratadine and Pseudophedrine Hydrochloride as Model Drugs." AAPS PharmaSciTech 11(2); 910-916 (available on-line May 22, 2010).
Polyok water-soluble resins (DOW Mar. 2002); see http://msds-search.dow.com/PublishedLiteratureDOWCOM/dh_0031/0901b80380031a4a.pdf?filepath=/326-00001.pdf&fromPage=GetDoc).
Swarbrick, Encyclopedia of Pharmaceutical Technology, Informa Healthcare, 1988, 1st edition. vol. 1, table of contents.
Swarbrick, Encyclopedia of Pharmaceutical Technology, Informa Healthcare, 1988, 1st edition, vol. 2. table of contents.
Swarbrick, Encyclopedia of Pharmaceutical Technology, Informa Healthcare, 1988, 1st edition, vol. 3, table of contents.
Swarbrick Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.

(56) References Cited

OTHER PUBLICATIONS

Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 20, table of contents.
European Search Report and Written Opinion for EP Application No. 13169658.5, Aug. 6, 2013.
European Search Report and Written Opinion for EP Application No. 13169659.3, Aug. 6, 2013.
Foye, W., Principles of Medicinal Chemistry; Structural Features and Pharmacologic Activity, pp. 63-66 at 65 (1989).
Foye, W., Principles of Medicinal Chemistry; Analgesics pp. 241-242, at 241 (1989).
Remington, The Science and Practice of Pharmacy, 19th ed., vol. II, p. 1457 (1995) (providing a table of DFA-approved commercially marketed salts).
Spassov et al., Stereochemistry of Diastereomeric 3-Dialkylaminopropanols and O-Derivatives, J.f. prakt. Chemie, 323:5, 793-800 (1981).
Handbuch der Kunststoff-Extrusionstechnik 1, "Grundlagen" in Chapter 1.2 "Klassifizierung von Extrudern", pp. 3-6. 1989.
2.9 Methoden der pharmazeutischen Technologie 143-144, 1997.
Apicella A., Biomaterials, vol. 14, No. 2, pp. 83-90, 1993.
Arnold, "Teen Abuse of Painkiller OxyContin on the Rise," www.npr.org, Dec. 19, 2005.
Bailey F.E., et al., "Some properties of poly(ethylene oxide)' in aqueous solution," Journal of Applied Polymer Science, vol. 1, Issue No. 1, pp. 56-62, 1959.
Bauer, Coated Pharmaceutical Dosage Forms, CRC Press, 1998, 1-10.
Baum et al., Public Health Reports, 102(4): 426-429 (1987).
Braun, et al. Angel Orthodontist, vol. 65 (5) pp. 373-377, 1995.
Caraballo, Journal of Controlled Release, vol. 69, pp. 345-355, 2000.
Coppens et al., "Hypromellose, Ethylcellulose, and Polyethylene Oxide Use in Hot Melt Extrusion"; Pharmaceutical Technology, 62-70, Jan. 2005.
Dachille, F. et al., "High-Pressure Phase Transformation in Laboratory Mechanical Mixers and Mortars", 1960., Nature, 186, pp. 1-2 (abstract).
Davies, et al; European Journal of Pharmaceutics and Biopharmaceutics, 67, 2007, pp. 268-276.
Dejong (Pharmaceutisch Weekblad Scientific Edition 1987, p. 24-28.
Dow Excipients Chem. Of Poly. Water Soluble-Resin 2004.
Dow Technical Data, POLYOX, Feb. 2003.
Efentakis M.,Pharmaceutical Development and Technology, 5 (3), pp. 339-346, 2000.
El-Sherbiny, European Polymer Journal, vol. 41, pp. 2584-2591, 2005.
Adel El-Egakey et al, Pharmacerutica Acta Helvetiae, vol. 46, pp. 31-53,Mar. 19, 1970.
Committee for Proprietary Medicinal Products. Note for Guidance on the Investigation of Bioavailability and Bioequivalence. 2001. pp. 1-18.
Fell, et al, Journal of Pharmaceutical Sciences, vol. 59, No. 5, May 1970, pp. 688-691.
Follonier N., Drug Development and Industrial Pharmacy, 20(8), pp. 1323-1339, 1994.
Follonier N. et al., Journal of Controlled Release 36, pp. 243-250, 1995.
Freed et al., "pH Control of Nucleophilic/electrophilic oxidation", International Journal of Pharmaceutics, vol. 357, pp. 180-188 (2008).
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Inert gas—Wikipedia, Dec. 2009.
Janicki S., Acta Pharm. Technol. 33 (3) 154-155, 1987.
Katz et al., Clin. J. Pain, 23(8): 648-660 (2007).
Kim C.-J. J Pharm. Sciences 1995, 84(3): pp. 303-306.
Kim, Chem. Pharm Bull. 1992, 40(10), 2800-2804.
J.W. McGinity—Letter of Jan. 26, 2009.
Dr. Rick Matos, Ph.D—Letter Jan. 6, 2011.
Levina et al., Drug Development and Industrial Pharmacy, vol. 28, No. 5, pp. 495-514, 2002.
Levina, Journal of Pharmaceutical Sciences, vol. 89, No. 6, pp. 705-723, Jun. 2000.
Lockhart et al, "Packaging of Pharnaceuticals and Health Care Products"; Blackie Academic & Professional; First Edition 1996.
Madorsky S.L., Journal of Polymer Science, vol. 36, No. 3, Mar. 1959.
Maggi. Therapeutic Potential of Capsaicin-like Molecules. Life Sciences, vol. 51, pp. 1777-1781, 1992.
Maggi et al., Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Mank R., Pharmazie 44, H. 11, pp. 773-776, 1989.
Mank R., Pharmazie 45, H. 8, pp. 592-593 1990.
Mesiha M.S., Drug Development and Industrial Pharmacy, 19(8), pp. 943-959, 1993.
Miller, Nursing, pp. 50-52, Feb. 2000.
Mitchell, Special Resource, vol. 35, No. 5, pp. 553-567, 2000.
Moroni A., Drug Development and Industrial Pharmacy, 21(12) pp. 1411-1428, 1995.
Ohnishi N. et al., Chem. Pharm. Bull, 35(8), pp. 3511-3515, 1987.
Ozeki T. et al., Journal of Controlled Release 58, pp. 87-95, 1999.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Verna et al., Manthena et al, Am. J. Drug Deliv. 2004: 2 (1): 43-57.
Pharmazeutische Biologie—Drogen and ihre Inhaltsstoffe—Scharfstoffdrogen, pp. 82-92 (WAGNER).
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Prapaitrakul W., J. Pharm. Pharmacol. 43, pp. 377-381, 1991.
Proeschel, J. Dent. Res., vol. 81, No. 7, pp. 464-468, 2002.
Radko S., Applied ad Theoretical Electrophoresis 5, pp. 79-88, 1995.
Remington's Pharmaceutical Sciences, pp. 1553-1593, Ch. 89, 1980, $16^{th}$ Edition.
Remington's Pharmaceutical Sciences 17th ed., 1418 (1985).
Rippie E.G., Journal of Pharmaceutical Sciences, Vo. 58, No. 4, pp. 428-431, Apr. 1969.
Search result conducted on http://www.unitconversion.org/force/newtons-to-kiloponds-convresion.html, on Jul. 5, 2011 (Conversion of 18.8 kiloponds to newtons).
Scheirs J., "Characterizing the Solid-State Thermal Oxidation of Poly (ethylene oxide) Powder", Polymer, vol. 32, No. 11, 1991.
Schroeder J.,Granulierung hydrophober Wirkstoffe im Planetwalzenextruder 2003, vol. 65, No. 4, 367-372.
Shivanand P.Pharmaceutical Research, Oct. 1991, vol. 8, No. 10, p. S-192.
Sprockel O.L., J. Pharma. Pharmacol. 42, pp. 152-157, 1990.
Stafford J., überzogene feste Formen, 1991, 347-68.
Strang, British Med. J., 302: 969 (1991).

(56) References Cited

OTHER PUBLICATIONS

Stringer J.L., Journal of Controlled Release 42, pp. 195-202, 1996.
Summers et al; Journal of Pharmaceutical Sciences, vol. 66, No. 8, Aug. 1977, pp. 1172-1175.
Tablet, www.docstoc.com (2011).
Third Party Observations, Feb. 2, 2009.
Thoma V.K. et al. "Bestimmung der In-vitro-Freigabe von schwach basischen Wirkstoffen aus Ratardarzneiformen", Pharm. Ind. 51, Nr. 3, 1989.
Tipler, et al, Physics for Scientists and Engineers, 6th Edition, pp. 234-235, 2003.
Tompkins et al., Psychopharma., 210: 471-480 (2010).
US Pharmacopoeia, Chapter 1217, Aug. 1, 2008.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", ACTA ODONTOL SCAND 53 (1995) : 254-258.
Waterman et al., "Stabilization of Pharmaceuticals to Oxidative Degredation", Pharmaceutical Development and Technology, vol. 71(1), pp. 1-32, (2002).
Waters et al., Am. J. Psychiatry, 164(1): pp. 173-174 (2007).
Wu N, Mathematical modeling and in vitro study of controlled drug release via a highly swellable and dissoluble polymer matrix: polyethylene oxide with high molecular weights, J Control Release. Feb. 16, 2005;102(3):569-81.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, Oct. 1996.
Yarbrough et al, Letters to Nature 322, 347-349 (Jul. 24, 1986) "Extraordinary effects of mortar-and -pestle grinding on microstructure of sintered alumina gel".
Zhang et al., Pharmaceutical Development and Technology, 1999, 4, 241-250.
Rowe et al. Handbook of Pharmaceutical Excipients. Sixth Edition. 2009, pp. v-ix, Table of Contents.
Herbert A. Lieberman, Pharmaceutical Dosage Forms, Tablets, Second Edition, Revised and Expanded, 1990.
Brown, "The Dissolution Procedure: Development and Validation" vol. 31(5). Chapter 1092, 2006, pp. 1-15.
Ritschel et al. Die Tablette: Handbuch der Entwicklung, Herstellung and Qualitatssicherung. 2002, Ch 6, pp. 515-519.
Bauer et al. Lehrbuch der Pharmazeutischen Technologie. 1999. pp. IX-XV, Table of contents.
European Pharmacopoeia, Third Edition, Council of Europe, Strasbourg, 1997, pp. 127-152.
European Pharmacopoeia, Third Edition Supplement 2000, Council of Europe, Strasbourg, 2000, pp. 85-107.
Hong et al. Dissolution kinetics and physical characterization of three-layered tablet with poly(ethylene oxide) core matrix capped by Carbopol. Int .J. Pharmacol. 2008, vol. 356, pp. 121-129.
Hoepfner et al. Fiedler Encyclopedia of Excipients. 2007, Table of Contents only.
Cawello, "Parameters for Compartment-free Pharmacokinetics—Standardization of Study Design, Data Analysis and Reporting" 1999, pp. XI-XIII (table of contents).
Ravin, Louis. Preformulation. Chapter 76. In Remington's Pharmaceutical Sciences, 17th Ed, 1985.
Disanto, Anthony. Bioavailability and Bioequivalency Testing. Chapter 77. In Remington's Pharmaceutical Sciences, 17th Ed, 1985.
Knevel, Adelbert. Separation. Chapter 78. In Remington's Pharmaceutical Sciences, 17th Ed, 1985.
Phillips, G. Briggs. Sterilization. Chapter 79. In Remington's Pharmaceutical Sciences, 17th Ed, 1985.
Siegel, Frederick. Tonicity, Osmoticity, Osmolality, and Osmolarity. Chapter 80. In Remington's Pharmaceutical Sciences, 17th Ed, 1985.
Giles et al. Plastic Packaging Materials. Chapter 81. In Remington's Pharmaceutical Sciences, 17th Ed, 1985.
Lintner, Carl. Stability of Pharmaceutical Products. Chapter 82. In Remington's Pharmaceutical Sciences, 17th Ed, 1985.
Erskine, Jr., Clyde. Quality Assurance and Control. Chapter 83. In Remington's Pharmaceutical Sciences, 17th Ed, 1985.
Nairn, J.G., Solutions, Emulsion, Suspensions and Extractives. Chapter 84. In Remington's Pharmaceutical Sciences, 17th Ed, 1985.
Avis, Kenneth. Parenteral Preparations. Chapter 85. In Remington's Pharmaceutical Sciences, 17th Ed, 1985.
Turco et al. Intravenous Admixtures. Chapter 86. In Remington's Pharmaceutical Sciences, 17th Ed, 1985.
Mullins, John. Ophthalmic Preparations. Chapter 87. In Remington's Pharmaceutical Sciences, 17th Ed, 1985.
Block, Lawrence. Medicated Applications. Chapter 88. In Remington's Pharmaceutical Sciences, 17th Ed, 1985.
Rippie, Edward. Powders. Chapter 89. In Remington's Pharmaceutical Sciences, 17th Ed, 1985.
King et al. Oral Solid Dosage Forms. Chapter 90. In Remington's Pharmaceutical Sciences, 17th Ed, 1985.
Porter, Stuart. Coating of Pharmaceutical Dosage Forms. Chapter 91. In Remington's Pharmaceutical Sciences, 17th Ed, 1985.
Longer et al. Sustained-Release Drug Delivery Systems. Chapter 92. In Remington's Pharmaceutical Sciences, 17th Ed, 1985.
Sciarra et al. Aerosols. Chapter 93. In Remington's Pharmaceutical Sciences, 17th Ed, 1985.
Repka MA,Drug Dev Ind Pharm. Oct. 2007;33(10):1043-57. (Abstract).
Kurt H. Bauer, K. Lehmann, Hermann P. Osterwald, Rothgang, Gerhart, 1st edition, 1998, Medpharm Scientific Publishers (table of contents).
O.G. Piringer, A.L. Baner, Plastic Packaging: Interactions with Food and Pharmaceuticals, Wiley VCH, 2nd Completely Revised Edition, Feb. 13, 2008.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Crowley MM,Drug Dev Ind Pharm. Sep. 2007;33(9):909-26.
D.A. Dean, E.R. Evans, I.H. Hall, Pharmaceutical Packaging Technology, Taylor & Francis, 1st Edition, Nov. 30, 2000.
Dexheimer, Terahertz Spectroscopy: Principles and Applications (Optical Science and Engineering Series), CRC; 1 edition 2007.
Encyclopedia of Pharmaceutical Technology, Third Edition, vol. 1, edited by James Swarbrick. Informa Healthcare, 3rd Edition, Oct. 25, 2006.
Encyclopedia of Pharmaceutical Technology, Third Edition, vol. 2, edited by James Swarbrick. Informa Healthcare, 3rd Edition, Oct. 25, 2006.
Encyclopedia of Pharmaceutical Technology, Third Edition, vol. 3, edited by James Swarbrick. Informa Healthcare, 3rd Edition, Oct. 25, 2006.
Encyclopedia of Pharmaceutical Technology, Third Edition, vol. 4, edited by James Swarbrick. Informa Healthcare, 3rd Edition, Oct. 25, 2006.
Encyclopedia of Pharmaceutical Technology, Third Edition, vol. 5, edited by James Swarbrick. Informa Healthcare, 3rd Edition, Oct. 25, 2006.
Encyclopedia of Pharmaceutical Technology, Third Edition, vol. 6, edited by James Swarbrick. Informa Healthcare, 3rd Edition, Oct. 25, 2006.
Y.-S. Lee et al., Principles of Terahertz Science and Technology (Lecture Notes in Physics), Springer; 1 edition 2008.
R.E. Miles et al., Terahertz Frequency Detection and Identification of Materials and Objects (NATO Science for Peace and Security Series B: Physics and Biophysics), Springer; 1 edition 2007.
Guidance for Industry—Statistical Approaches to Establishing Bioequivalence, FDA, BP, Jan. 2001.
Note for Guidance on the Investigation of Bioavailability and Bioequivalence, EMEA, London, Jul. 26, 2001 (CPMP/EWP/QWP/1401/98).

(56) References Cited

OTHER PUBLICATIONS

Application of a modelling system in the formulation of extended release hydrophilic matrices, Reprinted from Pharmaceutical Technology Europe, Jul. 2006.
Application of Opadry II, complete film coating system, on metformin HCI extended release matrices containing Polyox water soluble resin, Colorcon Apr. 2009.
Evaluation of Verapamil HCI (240 mg) Extended Release Matrix Formulation Using USP Apparatus III in Biorelevant Dissolution Media, Jul. 2009.
Formulation of Polyox ER Matrices for a Highly Soluble Active, Colorcon Jul. 2009.
Investigation of a Directly Compressible Metformin HCI 500mg Extended Release Formulation Based on Hypromellose, Colorcon Jul. 2009.
Metformin Hydrochloride 750 mg Extended Release Tablets, Lubrizol Advanced Materials, Inc., Sep. 2010.
Metformin Hydrochloride1000 mg Extended Release Tablets, Lubrizol Advanced Materials, Inc., Nov. 20, 2009, Previous Edition Dec. 19, 2008.
Pentoxifylline 400 mg Extended Release Tablets, Lubrizol Advanced Materials, Inc., Mar. 3, 2011, Previous Edition Nov. 19, 2009.
Physico-mechanical Characterization of Polyox for Table Manufacture, Colorcon Jul. 2009.
Tramadol Hydrochloride 100 mg Extended Release Tablets, Lubrizol Advanced Materials, Inc, Sep. 2010.
Perez-Marcos, B., Usefulness of certain varieties of Carbomer in the formulation of hydrophilic furosemide matrices, International Journal of Pharmaceutics, 67 (1991) 113-121.
Tikhonov, A. et al, Biopharmacy. The Manual for Students of Pharmaceutical Universities and Departments. 2003, pp. 40-41, Kharkov, Ukraine. (Full English translation attached.)
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Sreevivasa, B. et al, Design and evaluation of ethylene vinyl acetate sintered matrix tablets, Indian Journal of Pharmaceutical Sciences, Sep.-Oct. 2003, 65(5): 496-502.
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Andre et al., "O-Demethylation of Opiod Derivatives With Methane Sulfonic Acid/Methoinine: Application to the Synthesis of Naloxone and Analogues" Synthetic Comm. 22(16). pp. 2313-2327, 1992.
Augustine, R.L., Catalytic Hydrogenation of a, B-Unsaturated Ketones. III The Effect of Quantity and Type of Catalysts, J. Org Chem. 28(1), pp. 152-155, Abstract 1963.
Cornish, P. "Avoid the Crush": hazards of medication administration in patients with dysphagia or a feeding tube, CMA Media Inc., CMAJ. 172(7), pp. 871-872, 2005.
Crowley MM,Drug Dev Ind Pharm. Sep. 2007;33(9):909-26.(Abstract only).
Dachille et al., "High-pressure Phase Transformations in Laboratory Mechanical Mixers and Mortars", Nature, vol. 186, Apr. 2, 1960, pp. 34 and 71.
Deighan, C.J. et al., Rhabdomyolysis and acute renal failure resulting from alcohol and drug abuse, Q.J. Med, vol. 93, 2000, pp. 29-33.
Dow Chemical Company, "Using Dow Excipients for Controlled Release of Drugs in Hydrophilic Matrix Systems", Sep. 2006, pp. 1-36.
Encyclopedia of Pharmacological Technology, Informa Healthcare, 1st Ed., 1996, vol. 14 (Table of Content only).

European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Search Report and Opinion Application No. 12002708. 1-1219, Sep. 24, 2012.
European Search Report and Opinion Application No. 11006253. 6-2112, Dec. 16, 2011.
European Search Report and Opinion Application No. 11006254. 4-2112, Dec. 16, 2011.
European Search Report and Opinion Application No. 11008131. 2-1219, Feb. 24, 2012.
European Search Report and Opinion Application No. 11009129. 5-2112, Apr. 10, 2012.
European Search Report and Opinion Application No. 12001296. 8-1219, Jun. 26, 2012.
European Search Report and Opinion Application No. 12001301. 6-1219, Jun. 26, 2012.
European Search Report and Opinion Application No. 12003743. 7-1219, Sep. 24, 2012.
Evonik Industries, Eudragit Application Guidelines, 10th Edition, 2008, (Table of Contents only).
Goodman and Gilman, "The Pharmacological Basis of Therapeutics, Sevents Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Griffin W, "Classification of Surface-Active Agents By HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Guidance for Insutry—Statistical Approaches to Establishing Bioequivalence, FDA, BP, Jan. 2001.
Handbook of Pharmaceutical Excipients, 1986, American Pharmaceutical Association, Washington, DC and London (Table Content Only).
Henriest D. et al. In vitro and in vivo evaluation of starch-based hot stage extruded double matrix systems. Journal of Controlled Release. 2001, vol. 75, pp. 391-400.
James, A. "The legal and clinical implications of crushing tablet medication", Nurse Times 100(50), 28-33, 2004.
Kalant H. et al., Death in Amphetamine Users: Caues and Rates, CMA Journal, vol. 112 (Feb. 8, 1975); 299-304.
Liu J. et al., "Properties of Lipophilic Matrix Tables Containing Phenylpropanolamine Hydrochloride Prepared by Hot-Melt Extrusion", EPJB, 52 (2001), pp. 181-190.
McGary, C.W. Jr. "Degradation of Poly(ethylene Oxide)", Journal of Polymer Science vol. XLVI,1960, pp. 51-57.
McGinty et al., Hot-Melt Extrusion as a Pharmaceutical Process, American Pharmaceutical Review, vol. 4 (2), pp. 25-36, 2001.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.
Mitchell, "Oral Dosage Forms That Should Not Be Crushed: 2000 Update" Hospital Pharmacy 35(5), 553-557, 2000.
Miles, R.E. et al., Terahertz Frequency Detection and Identification of Materials and Objects (NATO Science for Peace and Security Series B: Physics and Biophysics), Springer; 1 edition 2007.(Table of contents).
Munjal M. et al"Polymeric Systems for Amorphous Delta9—Tetrahydrocannabinol Produced by a Hot-Melt Method, Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Note for Guidance on Stability Testing, EMEA, Aug. 2003, pp. 1-20.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.

(56) References Cited

OTHER PUBLICATIONS

Ozeki T. et al. "Controlled Release From Solid Dispersion Composed of Poly(ethylene oxide)-Carbopol Interpolymer Complex With Various Cross-Linking Degrees of Carbopol", Journal of Controlled Release 63, 2000. pp. 287-295.
Pillay V. et al. A novel approach for constant rate delivery of highly soluble bioactives from a simple monolithic system. Journal of Controlled Release, 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007;33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rowe C et al., Handbook of Pharmaceutical Excipients, 7th Edition, 2012, Table of Contents.
Schier et al. "Fatality from Administration of Labetalol and Crushed Extended-Release Nifedipine" The Annals of Pharmacotherapy vol. 37, 1420-1423, Oct. 2003.
Wade and Weller, "Handbook of Pharmaceutical Excipients: 2nd Edition", The American Pharmaceutical Association and The Pharmaceutical Press, Washington and London, Table of Contents pp. v-vi, 1994.
Waters et al "Intravenous Quetiapine-Cocaine Use ("Q-Ball")", Letter to the Editor, Am. J. Psychiatry, 164(1): pp. 173-174 (2007).
Weiss, U, "Derivatives of Morphine. I 14-Dihydroxydihydromorphinone," J. Am. Chem. Soc. 77, pp. 5891-5892, Nov. 20, 1955.
Woodburn, K.R. et al., Vascular complications of injecting drug misuse, Br. J. of Surgery, vol. 83, 1996, pp. 1329-1334.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Ritschel et al. Die Tablette: Handbuch der Entwicklung, Herstellung und Qualitatssicherung. 2nd Edition, 2002, Ch 6, pp. 515-519. (Full English translation attached).
Albertini, B. "New spray congealing atomizer for the microencapsulation of highly concentrated solid and liquid substances," European Journal of Pharmaceutics and Biopharmaceutics 69 (2008) 348-357.
European Search Report and Written Opinion for EP Application No. 13197503.9-1460, Feb. 18, 2014.
Jannetto, P. et al, "Oxycodone: Recognition and Pharmacogenomics," Toxicology News, Mar. 2003, 1-7.
Kolter, K., "Compression Behaviour of Kollidon SR," APV/ APGI 2002, Florence, Apr. 11, 2002.
Mises à jour cumulatives, Vidal, Jan./Oct. 2002.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Pontier, C. et al, "Use of cycles of compression to characterize the behavior of apatitic phosphate powders," Journal of the European Ceramic Society 22 (2002), 1205-1216.
Silver, J. "Painkiller OxyContin most commonly abused prescription drug on the streets of Western Pennsylvania", Pittsburg Post-Gazette, Apr. 8, 2001.
Wikipedia-Dextromethorphan Aug. 12, 2013 (and attached related English-language entry dated Dec. 11, 2013).
Gryczke et al, "Development and evaluation of orally disintegrating tablets (ODTs) containing Ibuprofen granules prepared by hot melt extrusion", Colloids and surfaces., B: Biointerfaces, Elsevier, Amsteram, NL, vol. 86, No. 2, Apr. 5, 2011, pp. 275-284.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
European Search Report and Written Opinion for EP Application No. 13425151.1-1460, Mar. 11, 2014.
Carbopol 71G, retrieved Mar. 10, 2014 from http://www.lubrizol.com/LifeScience/Products/Carbopol71G-NF.html.
Polyox WSR-303, retrieved Mar. 10, 2014 from URL http://www.dow.com/dowwolff/en/industrial_solutions/polymers/polyethylene.
Li et al, "Characterization of Poly (Ethylene Oxide) as a Drug Carrier in Hot-Melt Extrusion", Drug Development and Industrial Pharmacy, vol. 32, No. 8, Jan. 1, 2006, pp. 991-1002.
European Search Report and Written Opinion for EP Application No. 13176309.9-1460, Oct. 9, 2013.
Lenindzer, A., "The molecular basis of the structure and functions of cells" Moscow 1974, p. 68.
Kondrat, T. , "Technology dosage forms" Moscow 1991, p. 96.
Costa et al. "Modeling and comparison of dissolution profiles"; European Journal of Pharmaceutical Sciences 13 (2001) 123-33.
Eggleston, The seat of the emetic action of various drugs: J. Pharmacol. Exp. Ther. 7, 225-253 (1915).
Morissette et al. Adv. Drug. Del. Rev. 26 (2004), 275-300.
Vippagunta et al. Adv. Del. Rev. (2001), 3-26.
POLYOX, Colorcon, Application Data (Apr. 2009) downloaded from http://www.colorcon.com/literature/marketing/mr/Extended%20Release/POLYOX/English/ads_PEO_Antioxidant.pdf.
PCT Second Written Opinion for PCT Application PCT/EP2013/057851 dated Apr. 15, 2014.
PCT International Search Report and Written Opinion for PCT Application No. PCT/EP2014/075618 dated Feb. 11, 2015
Eudragit NE40D web page from Evonik website; downloaded Feb. 24, 2015.
Eudragit RS PO web page from Evonik website; downloaded Feb. 24, 2015.
Glyceryl behenate monograph; European Pharmacopeia 5.0; dated Jan. 2005; downloaded Feb. 24, 2015.
Dierickx et al., "Co-extrusion as manufacturing technique for fixed-dose combination mini-matrices," European Journal of Pharmaceutics and Biopharmaceutics 81 (2012), 683-689.
Eggleston, "The seat of the emetic action of various drugs," J. Pharmacol. Exp. Ther. 7, 225-253 (1915).
European Search Report and Opinion Application No. 14176277.3-1460, Dec. 15, 2014.
European Search Report and Written Opinion for EP Application No. 14169801.9-1455 Oct. 20, 2014.
Evonik Rohm GmbH product brochure: EUDRAGIT acrylic polymers for solid oral dosage forms (2009).
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Oliveira et al., "Production and characterization of laminar coextrudates at room temperature in the absence of solvents," AAPS Annual Meeting and Exposition, Oct. 14-18, 2012, Chicago, USA.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2013). pp. 1250-1258.
Salomies et al., "Determination of Oxycodone Hydrochloride in Oral Solutions by High-Performance Thin-Layer Chromatography/Densitometry," Journal of AOAC International, 83: 1497-1501 (2000).
Vippagunta et al. Advanced Drug Delivery Review 48 (2001), 3-26.

(56) References Cited

OTHER PUBLICATIONS

Bruce et al, Properties of hot-melt extuded tablet formulations for the colonic delivery of 5-aminosalicylic acid, European Journal of Pharmaceutics and Biopharmaceutics, 59 (2005) 85-97.
West, Anthony R., Solid state chemistry and its applications, Wiley, New York, 1988, pp. 358 and 365.
Extended European Search Report and Opinion for Application No. EP 15165067.8-1455, Nov. 2, 2015.
Extended European Search Report and Opinion for Application No. EP 15165065.2-1455, Nov. 2, 2015.
Extended European Search Report and Opinion for Application No. EP 15165069.4-1455, Nov. 2, 2015.
Extended European Search Report and Opinion for Application No. EP 15165064.5-1455, Oct. 16, 2015.
Extended European Search Report and Opinion for Application No. EP 15165070.2-1455, Nov. 2, 2015.
Monolithic: retrieved from internet: http:/merriam-webster.com/dictionary/monolithic. Retrieved on Sep. 2, 2015.
Bingwen et al, 2008, p. 367.
Bingwen et al, 2008, p. 367. (full translation attached).
Extended European Search Report and Opinion for Application No. EP 15153679.4-1455, Jun. 30, 2015.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Extended European Search Report for Application No. EP 16183922.0-1460, Oct. 31, 2016.
Decision of the United States District Court for the Southern District of New York, in In re *Endo Pharmaceuticals Inc. and Grünenthal GmbH* v. *Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re *Oxycontin Antitrust Litigation, Purdue Pharma LP* v. *Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P.* v. *Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 128:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes In and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro at al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the 29th Annual Meeting of the Controlled Release Society, in collaboration with the Korea Society for Biomaterials, Minneapolis, 1st Edition, 2002, 984-985.

Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy Applications (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
Crowley0000001-Crowley0000127.
Davies, N. "Sustained Release and Enteric Coated NSAIDs: Are They Really GI Safe?"J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun., 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
*Endo Pharmaceuticals Inc.* v. *Teva Pharmaceuticals USA, Inc.* (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).
Jaffe, S.L., "Failed Attempts At Intranasal Abuse of Concerta," Letters to the Editor, J. Am. Acad. Child Adolesc. Psychiatry, 41:1 (Jan. 2002).
Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf
Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).

(56) References Cited

OTHER PUBLICATIONS

Kibbe, Coloring Agents, in Handbook of Pharmaceutical Excipients (3d ed. 2000).
Kidokoro, M. et al. ,"Properties of Tablets Containing Granulations of Ibuprofen and Acrylic Copolymers Prepared by Thermal Processes," Pharm Dev. and Tech. , 6:263-275 (2001).
Kinjo, N. et al, "Antiplasticization in the Slightly Plasticized Poly(vinyl chloride)," Polymer Journal 4(2):143-153 (1973).
Larhib, H. et al., "Compressing polyethyelene glycols: the effect of compression pressure and speed," Int'l J Pharmaceutics (1997) 147: 199-205.
Lieberman, H., et al., Pharmaceutical Dosage Forms: Tablets, vol. 2, Ch. 5: Granulation Technology and Tablet Characterization (1990), Table of contents and 245-348.
Lyons et al., "Twitch Interpolation in the Assessment of the Maximum Force-Generating Capacity of the Jaw-Closing Muscles in Man," Arch. Oral. Biol. 41:12, 1161-1168 (1996).
Makki, A, et. al., Eds., A Dictionary of American Idioms, 4th Ed. Barron's, New York (2004), 342-343.
Markovitz, H., et al. "Calculations of Entanglement Coupling Spacings in Linear Polymers." Journal of Physical Chemistry, 1962. 66(8): 1567-1568.
McCrum, N., et al., Principles of Polymer Engineering. 2nd ed., New York: Oxford University Press. 447(1997), Chapter 7, 296-351.
McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.
McQuay, H. et a. "Methods of Therapeutic Trials," Textbook of Pain 1125-1138 (P.D. Wall & R. Melzack eds., Elsevier 4th ed. 1999), Table of Contents and 1125-1138.
Miura et al., "Comparison of Maximum Bite Force and Dentate Status Between Healthy and Frail Elderly Persons," J. Oral Rehabilitation, vol. 28 (2001), pp. 592-595.
Miyagawa, Y. et al., "Controlled-release of diclofenac sodium from wax matrix granulate," Int 'l J. Pharmaceutics (1996) 138:215-224.
National Drug Intelligence Center Information Bulletin "OxyContin Diversion and Abuse" Jan. 2001.
Payne, H. et al., Denatonium Benzoate as a Bitter Aversive Additive in Ethylene Glycol and Methanol-Based Automotive Products, SAE Technical Paper 930589, Abstract (1993).
Pilpel, N., et al. "The effect of temperature on the tensile strength and disintegration of paracetamol and oxytetracylcine tablets," J Pharm Pharmac., 29:389-392 (1977).
Polyox Water-Soluble Resins NF in Pharmaceutical Applications, Dow Chemical Company, Aug. 2002.
Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.
Rauwendaal, Chris, PHD, Responsive Expert Report of Chris Rauwendaal, Ph.D. Regarding Expert Report of Michael M. Crowley, Ph. D., dated Jul. 17, 2015.
Repka, M. et al. Pharmaceutical Applications of Hot-Melt Extrusion: Part II. Drug Dev. & Indus. Pharmacy (2007) 33:1043-1057.
Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.
Seitz, J.A.; et al., "Evaluation of the Physical Properties of Compressed Tablets 1: Tablet Hardness and Friability," J. of Pharm. Sci. , 54:1353-1357 (1965).
Shah, et al., "Some Effects of Humidity and Heat on the Tableting Properties of Microcrystalline Cellulose Formulations 1," J. of Pharm. Sci., 57:181-182 (1967).
Singhal, et al., Handbook of Indices of Food Quality and Authenticity (1997), "Capsicum" p. 398-299.
Smith, K.L. et al. "High Molecular Weight Polymers of Ethylene Oxide—Plastic Properties." Industrial and Engineering Chemistry, 1958. 50(1): 12-16.
Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.
Tiwari, D., et al., "Evaluation of polyoxyethylene homopolymers for buccal bioadhesive drug delivery device formulations." AAPS Pharmsci. 1999. 1(3): Article 13.
Wilkins, J.N., "Pharmacotherapy of Schizophrenia Patients with Comorbid Substance Abuse," Schizophrenia Bulletin, 23:215-228 (1997).
World Health Org., Cancer Pain Relief With a Guide to Opioid Availability (2d ed. 1996).
Yin, T.P., et al., "Viscoelastic Properties of Polyethylene Oxide In Rubber-Like State." Journal of Physical Chemistry, 1961. 65(3): 534-538.
Zacny, J. et al. Drug & Alcohol Dependence (2003) 69:215-232.
Zhang, F., "Hot-Melt Extrusion as a Novel Technology to Prepare Sustained-Release Dosage Forms," Dissertation University of Texas at Austin, Dec. 1999.
Remington, Chapter 45, pp. 996-1035.
Alekseeva et al, Chemical-Pharmaceutical Journal, vol. 41, No. 9, 2007, 49-52. (Full translation attached.).
Borquist et al., "Simulation of the release from a multiparticulate system validated by single pellet and dose release experiements," J. Controlled Release, 97: 453-465 (2004).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Cuesov, Drug Production Technology, Khar'kov, 1999, pp. 351-352.
Efentakis et al, Effects of Excipients on Swelling and Drug Release from Compressed Matrices, in Drug Development and Industrial Pharmacy 23(1):107-112, Jan. 1997, Abstract.
Extended European Search Report and Opinion for Application No. EP 15184634.2-1455, Mar. 3, 2016.
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Saleem et al. "Formulation and Evaluation of Tramadol hydrochloride Rectal Suppositories," Indian J. Pharm Sci. Sep.-Oct. 2008; 70(5), 640-644.
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sidhu et al., "Watch for nonpsychotropics causing psychiatric side effects," Current Psychiatry, vol. 7, No. 4, 2008, 61-74.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics, 63 (2006) 320-330.
Vynckier et al., "Hot-melt co-extrusion for the production of fixed-dose combination products release ethylcellulose matrix core," International Journal of Pharmaceutics 464 (2014), 65-74.
Fathima, N. et al. "Drug-excipient interaction and its importance in dosage form development," Journal of Applied Pharmaceutical Science 01 (06); 2011, pp. 66-71.

(56) References Cited

OTHER PUBLICATIONS

Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella, Biomaterials, 14: 83-90 (1993).
Augustine, R.L., Catalytic Hydrogenation of a, B-Unsaturated Ketones. III The Effect of Quantity and Type of Catalysts, J.Org Chem. 28(1), pp. 152-155, Abstract 1963.
Avis, Kenneth., Parenteral Preparations. Chapter 85. pp. 1518-1541, In Remington's Pharmaceutical Sciences, 17th Ed, 1985.
C.J. Deighan et al., Rhabdomyolysis and acute renal failure resulting from alcohol and drug abuse, Q.J. Med, vol. 93, 2000, pp. 29-33.
Crowley M.M. et al., Biomaterials 23, 2002, pp. 4241-4248.
DeJong (Pharmaceutisch Weekblad Scientific Edition) 1987, p. 24-28.
Dow Chemical Company, Using Methocel Cellulose Ethers for Controlled Release of Drugs in Hydrophilic Matrix Systems, 2006, pp. 1-36.
Fell, J. Pharm. Sci., 59(5): 688-691 (1970).
Goodman and Gilman, "The Pharmacological Basis of Therapeutics, Seventh Edition", MacMillan Publishing Company, Table of Contents. 1985.
Kalant et al., Death in Amphetamine Users: Causes and Rates, CMA Journal, vol. 112, Feb. 8, 1975 pp. 299-304.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
The McGinity Letter, dated Jan. 26, 2009.
McGinity et al., Hot-Melt Extrusion as a Pharmaceutical Process, American Pharmaceutical Review, vol. 4 (2), pp. 25-36, 2001.
Pinto et al.,"Evaluation of the Potential Use of Poly(ethylene oxide) as Tablet- and Extrudate-Forming Material," AAPS PharmSci, 2004; 6 (2) Article 15, pp. 1-10.
Riippi et al., The effect of compression force on surface structure, crushing strength, friability and disintegration time of erythromycin acistrate tablets, Eur J Pharm Biopharm, vol. 46, 1998, pp. 339-345.
Sax et al., Hawley's Condensed Chemical Dictionary, 11$^{th}$ ed., 1987, p. 1233.
Weiss, U., "Derivatives of Morphine. 1 14-Dihydroxydihydromorphinone," J. Am. Chem. Soc. 77, pp. 5891-5892, Nov. 20, 1955.
Woodburn et al., Vascular complications of injecting drug misuse, Br. J. of Surgery, vol. 83, 1996, pp. 1329-1334.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Zhang et al., "Properties of Sustained-Release Tablets Prepared by Hot-Melt Extrusion" Pharmaceutical Development and Technology, 1999, 4(2), 241-250.
Apicella A.et al., Biomaterials, vol. 14, No. 2, pp. 83-90, 1993.
McGinity, J.W.—Letter of Jan. 26, 2009, pp. 1-4.
Riippi et al., The effect of compression force on surface structure, crushing strength, friability and disintegration time of erythromycin acistrate tablets, Eur J Pharm Biopharm, vol. 46, 1998, pp. 339-345.
Sax et al., Hawley's Condensed Chemical Dictionary, 11th ed., 1987, p. 1233, definition of "wax".
Weiss, U., "Derivatives of Morphine. I 14-Dihydroxydihydromorphinone," J. Am. Chem. Soc. 77, pp. 5891-5892, Nov. 20, 1955.
European Search Report and Written Opinion for EP Application No. 11006253.6-2112 dated Dec. 16, 2011.
European Search Report and Written Opinion for EP Application No. 11006254.4-2112 dated Dec. 16, 2011.
European Search Report and Written Opinion for EP Application No. 11008131.2-1219 dated Feb. 24, 2012.
European Search Report and Written Opinion for EP Application No. 11009129.5-2112 dated Apr. 10, 2012.
European Search Report and Written Opinion for EP Application No. 12001296.8-1219 dated Jun. 26, 2012.
European Search Report and Written Opinion for EP Application No. 12001301.6-1219 dated Jun. 26, 2012.
European Search Report and Written Opinion for EP Application No. 12002708.1-1219 dated Sep. 24, 2012.
European Search Report and Written Opinion for EP Application No. 12003743.7-1219 dated Sep. 24, 2012.
European Search Report and Written Opinion for EP Application No. 13169658.5 dated Aug. 6, 2013.
European Search Report and Written Opinion for EP Application No. 13169659.3 dated Aug. 6, 2013.
European Search Report and Written Opinion for EP Application No. 13176309.9-1460 dated Oct. 9, 2013.
European Search Report and Written Opinion for EP Application No. 13197503.9-1460 dated Feb. 18, 2014.
European Search Report and Written Opinion for EP Application No. 13425151.1-1460, dated Mar. 11, 2014.
European Search Report and Written Opinion for EP Application No. 14169801.9-1455, Oct. 20, 2014.
European Search Report and Opinion Application No. 14176277.3-1460, dated Dec. 15, 2014.
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
PCT International Search Report and Written Opinion for PCT Application No. PCT/EP2009/003290 dated Jul. 9, 2009.
PCT International Search Report and Written Opinion for PCT Application No. PCT/EP2010/004459 dated Dec. 1, 2010.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/061343 dated Jul. 21, 2015.
PCT International Search Report and Written Opinion for PCT Application No. PCT/EP2015/060377 dated Jul. 23, 2015.
Tranquilan-Aranilla et al., "Kappa-carrageenan-polyethylene oxide hydrogel blends prepared by gamma irradiation," Radiation Physics and Chemistry vol. 55, pp. 127-131, 1999.

\* cited by examiner

Figure 13A
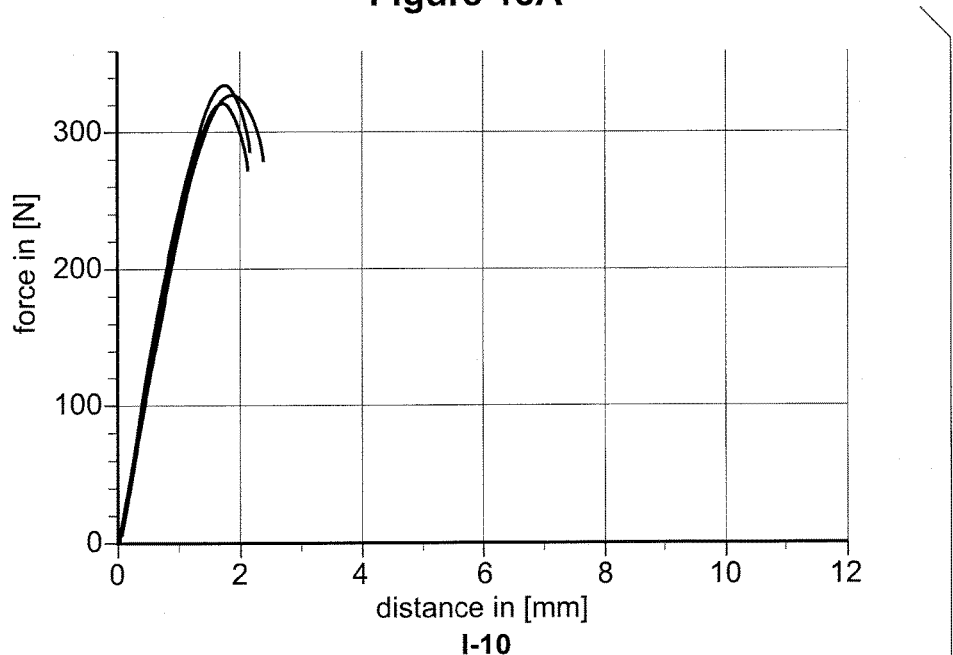
I-10
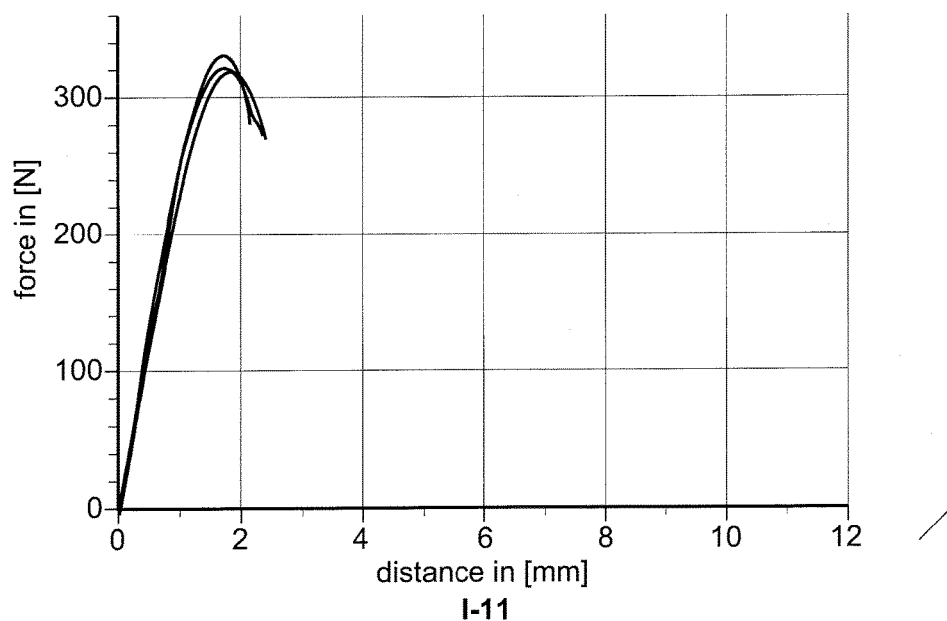
I-11

Figure 13B
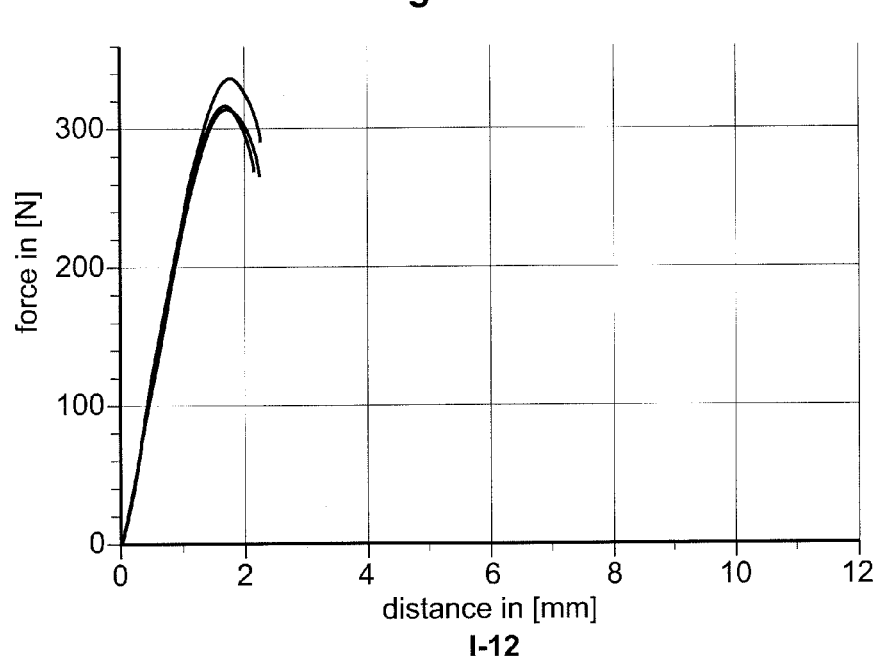
I-12
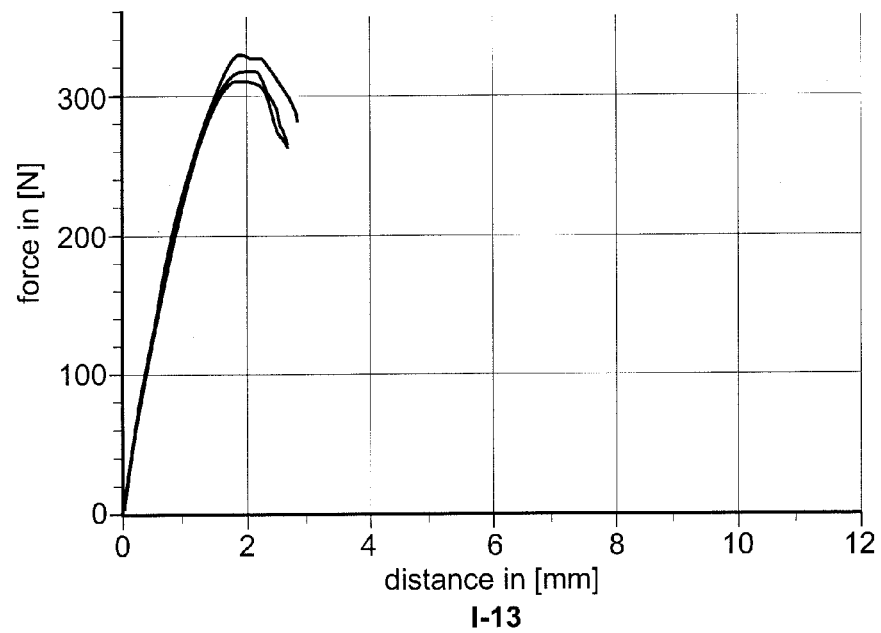
I-13

Figure 13C
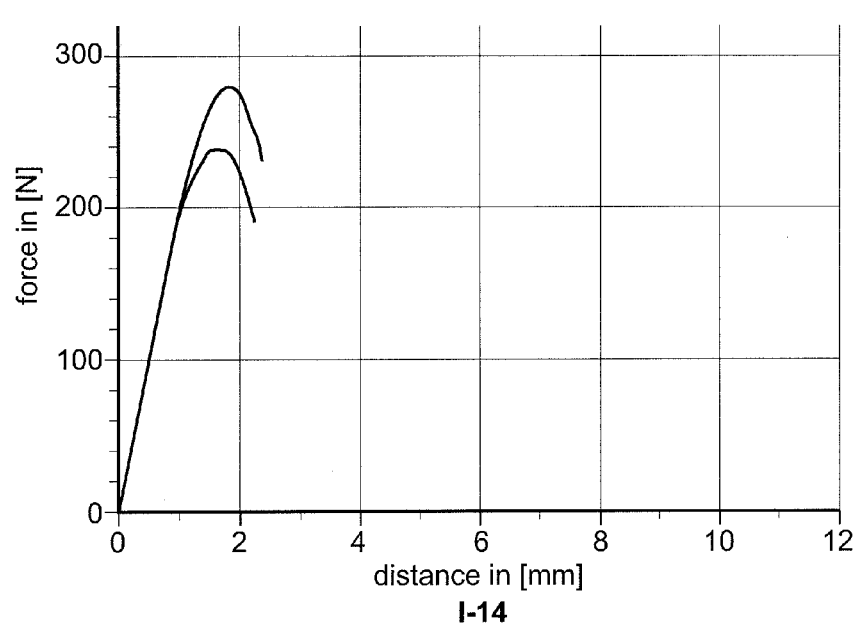
I-14
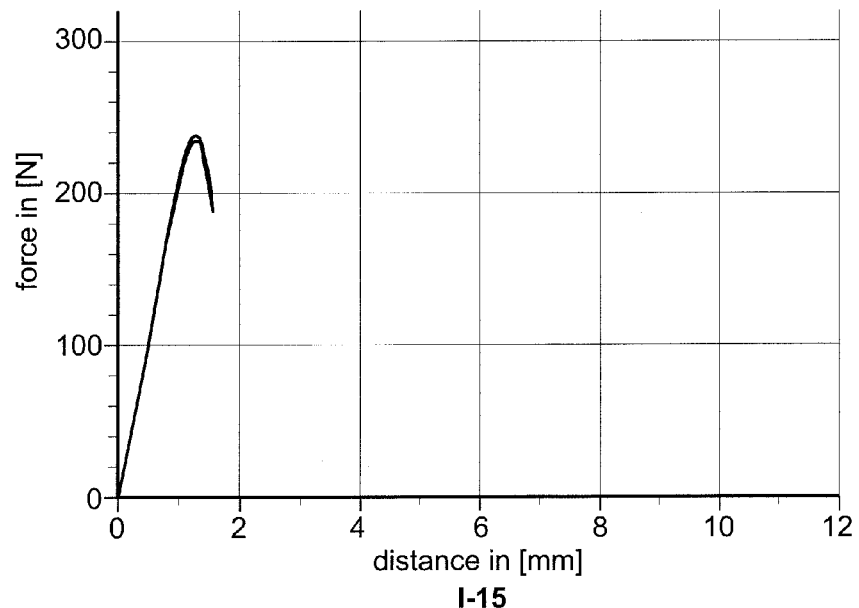
I-15

Figure 13D
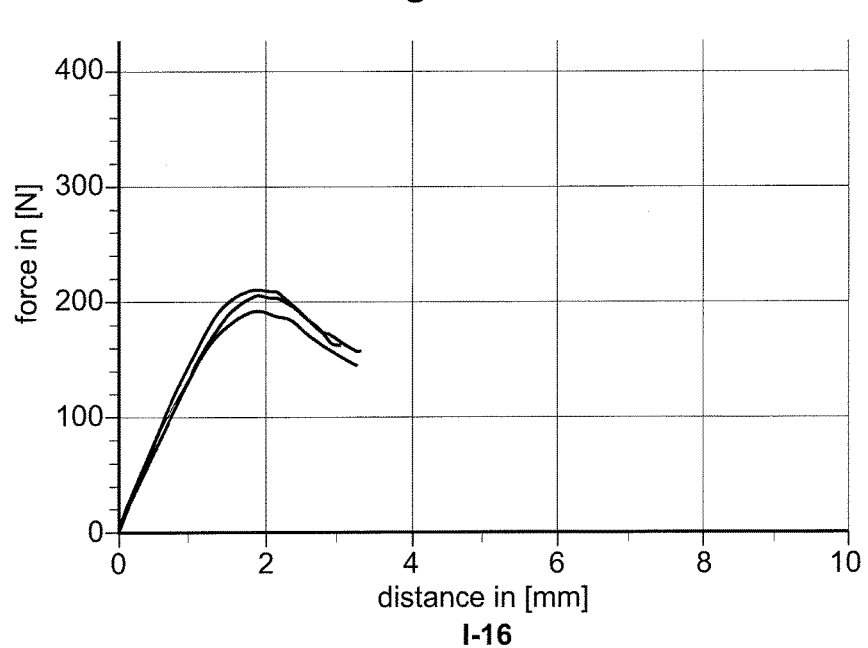
I-16
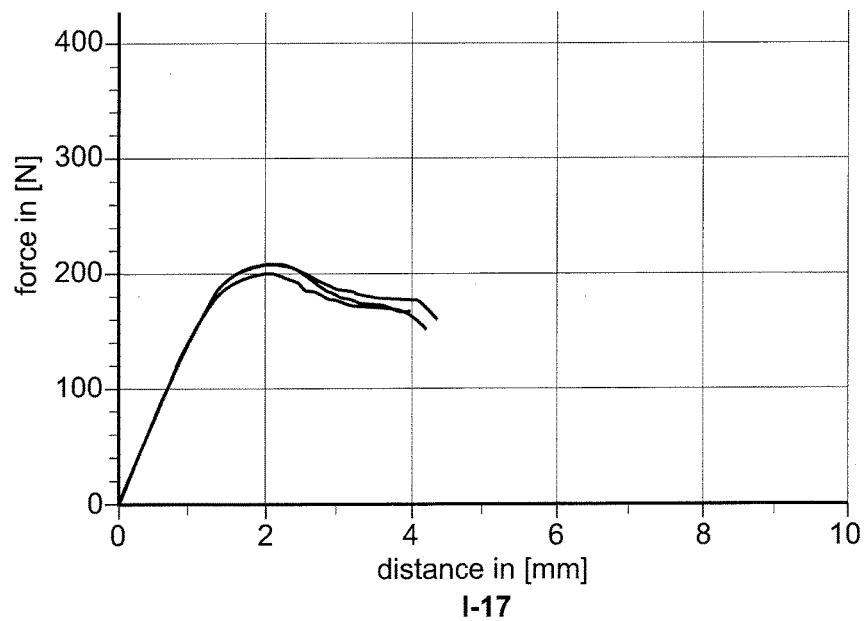
I-17

TAMPER RESISTANT DOSAGE FORM COMPRISING AN ANIONIC POLYMER

This patent application claims priority of U.S. Provisional Patent Application No. 61/379,507, filed on Sep. 2, 2010, and European Patent Application No. 10 009 125.5, filed on Sep. 2, 2010, the entire contents of both of which patent applications are incorporated herein by reference.

The invention relates to a pharmaceutical dosage form exhibiting a breaking strength of at least 500 N, said dosage form containing a pharmacologically active ingredient (A); a physiologically acceptable polymer (B) obtainable by polymerization of a monomer composition comprising an ethylenically unsaturated monomer bearing an anionic functional group, in protonated form or a physiologically acceptable salt thereof; and a polyalkylene oxide (C) having a weight average molecular weight of at least 200,000 g/mol, wherein the content of the polyalkylene oxide (C) is at least 20 wt.-%, based on the total weight of the dosage form; wherein the ingredient (A) is present in a controlled-release matrix comprising the polymer (B) and the polyalkylene oxide (C).

Many pharmacologically active compounds have a potential of being abused and thus, are advantageously provided in form of tamper resistant pharmaceutical dosage forms. Prominent examples of such pharmacologically active compounds are opioids.

It is known that abusers crush conventional tablets, which contain opioids, to defeat the time-release "micro-encapsulation" and then ingest the resulting powder orally, intranasally, rectally, or by injection.

Various concepts for the avoidance of drug abuse have been developed. One concept relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded.

Such pharmaceutical dosage forms are useful for avoiding drug abuse of the pharmacologically active compound contained therein, as they may not be powdered by conventional means and thus, cannot be administered in powdered form, e.g. nasally. The mechanical properties, particularly the high breaking strength of these pharmaceutical dosage forms renders them tamper resistant. In the context of such tamper resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, WO 2008/107149, and WO2009/092601.

The mechanical properties of such conventional tamper resistant dosage forms, however, are not satisfactory in every respect. In particular, when exerting a force of 500 N or more to these conventional dosage forms, they typically tend to escape the force by deformation so that they can be flattened to a certain degree. Though such flattening typically does not render the dosage forms suitable for abuse, it would be desirable to reduce deformability and to increase impact strength, respectively, without at the same time to increase brittleness.

Further, the release kinetics of the pharmacologically active ingredients from such tamper resistant dosage forms is an important factor. It is well known that depending on how a pharmaceutically active ingredient is formulated into a tablet its release pattern can be modified. In this regard, tablets providing a retarded release profile are of primary importance. With retarded release tablets care has to be taken that under no circumstances the pharmaceutically active ingredient will be released completely and instantaneously in an uncontrolled manner ("dose-dumping") since regularly the dosage used for retarded release tablets is much higher than for non-retarded release tablets. This may cause serious adverse effects or even death depending on the active ingredient and potency thereof.

US 2007/190142 discloses a dosage form and method for the delivery of drugs, particularly drugs of abuse, characterized by resistance to solvent extraction, tampering, crushing, or grinding, and providing an initial burst of release of drug followed by a prolonged period of controllable drug release WO 2008/148798 discloses layered pharmaceutical composition suitable for oral use in the treatment of diseases where absorption takes place over a large part of the gastrointestinal tract.

WO 2006/058249 relates to an abuse deterrent formulation of an oral dosage form of a therapeutically effective amount of any active drug substance that can be subject to abuse combined with a gel forming polymer, a nasal mucosal irritating surfactant and a flushing agent. Such a dosage form is intended to deter abuse of the active drug substance via injection, nasal inhalation or consumption of quantities of the dosage unit exceeding the usual therapeutically effective dose.

WO 03/024426 discloses a controlled release pharmaceutical composition for oral use comprising a solid dispersion of: i) at least one therapeutically, prophylactically and/or diagnostically active substance, which at least partially is in an amorphous form, ii) a pharmaceutically acceptable polymer that has plasticizing properties, and iii) optionally, a stabilizing agent, the at least one active substance having a limited water solubility, and the composition being designed to release the active substance with a substantially zero order release.

Controlled release (e.g. delayed release, prolonged release, sustained release, and the like) may be based upon various concepts such as coating the pharmaceutical dosage form with a controlled release membrane, embedding the pharmacologically active compound in a matrix, binding the pharmacologically active compound to an ion-exchange resin, forming a complex of the pharmacologically active compound, and the like. In this context it can be referred to, e.g., W. A. Ritschel, Die Tablette, 2. Auflage, Editio Cantor Verlag Aulendorf, 2002.

It is well known that a pharmaceutical formulation or its mode of manufacture, e.g. for an oral dosage form, might undergo modifications during clinical testing, for example with respect to the ingredients used or to the relative amounts of the excipients, or with respect to the reaction conditions and reactants used during manufacture. Frequently, such modifications at least to some extent have an impact on the release profile of pharmaceutically active ingredients. This is particularly unpleasant if for a specific formulation an approved optimized release profile has already been found which can not be reproduced with the modified formulation. In such a case, the clinical tests have either to be interrupted or have to be started from the beginning. Given the huge expenditures necessary to bring a new drug formulation up to and through clinical testing the above scenario has indeed proven to be rather unsatisfactory.

Particular problems arise when the dose of the pharmacologically active compound and thus, also the total weight of the pharmaceutical dosage form is comparatively high.

Depending upon the content and the nature of the pharmacologically active compound and of the pharmaceutical excipients, the retardant effect of the polymer may be too weak so that the pharmaceutical dosage form cannot be adapted to a specific dosing regimen, e.g., twice daily, particularly when the increased breaking strength is to be maintained.

An increase of the content of the retardant polymer for the purpose of decelerating drug release would substantially increase the total weight of the pharmaceutical dosage form and in a worst case scenario, would lead to a size that could not be swallowed by a subject.

Thus, there is a demand for tamper-resistant pharmaceutical dosage forms, the release profile of which may be varied within certain limits without diminishing the tamper resistance and without deteriorating the compliance of the pharmaceutical dosage form. Furthermore, there is a demand for tamper-resistant pharmaceutical dosage forms exhibiting mechanical properties that are even further improved compared to the break-resistant dosage forms of the prior art.

T. Ozeki et al., International Journal of Pharmaceutics, 165 (1998) 239-244 disclose poly(ethylene oxide)-carboxyvinylpolymer solid dispersions prepared from water/ethanol mixture as a solvent. Similarly, T. Ozeki et al., Journal of Controlled Release, 63 (2000) 287-295 relates to controlled release from solid dispersion composed of poly(ethylene oxide)-Carbopol® interpolymer complex with various cross-linking degrees of Carbopol®. However, these solid dispersions prepared from water/ethanol are not suitable for the avoidance of drug abuse. Further, the polyethylene oxide employed in these studies had an average molecular weight of below 150,000 g/mol only.

Hong et al., Int. J. Pharm. 356 (2008) 121-129 discloses poyl(ethylene oxide) tablets which have three-layered structure prepared by direct compression. Carbopol was coated on both sides of the central PEO matrix which contains solid-dispersed nifedipine in PEG4000.

It is an object of the invention to provide pharmaceutical dosage forms having advantages compared to pharmaceutical dosage forms of the prior art.

This object has been achieved by the subject-matter defined hereinbelow.

It has been surprisingly found that comparatively low amounts of matrix polymers bearing anionic functional groups provide a further delay of the release of the pharmacologically active ingredients from the tamper resistant dosage forms without diminishing the specific mechanical properties and without leading to a substantial increase of the overall weight.

It has been surprisingly found that by selection of an appropriate amount of an appropriate matrix polymer bearing anionic functional groups the release profile of the pharmaceutical dosage form can be varied over a broad range and that the release of the pharmacologically active ingredient can be particularly retarded compared to a pharmaceutical dosage form not containing said amount of said matrix polymer bearing anionic functional groups.

This is even more surprising considering that these polymers are highly hydrophilic and thus should tend to rapidly swell upon contact with an aqueous medium thereby accelerating the hydration of the matrix in which they are embedded. Therefore, one would typically expect that the faster the swelling and dilution of the matrix, the faster the release. It has been surprisingly found, however, that the release is retarded by the addition of the hydrophilic polymers.

Further, it has been surprisingly found that said matrix polymers bearing anionic functional groups even improve the mechanical properties of the dosage forms. In particular, it has been unexpectedly found that the deformability of the dosage forms can be decreased by the presence of the matrix polymers bearing anionic functional groups thereby leading to dosage forms having improved mechanical strength and hardness, respectively, without becoming brittle. It has been unexpectedly found that the matrix polymers bearing anionic functional groups improve the cut resistance of break resistant dosage forms that are based on high molecular weight polyalkylene oxides. This is of particular importance, as it is known that tampering of conventional dosage forms is often achieved by means of knives and other cutting tools. Thus, the dosage forms according to the invention provide specific resistance against this type of tampering.

BRIEF DESCRIPTION OF THE DRAWINGS

The invention will now be described in greater detail with reference to the drawings.

Figure 1:
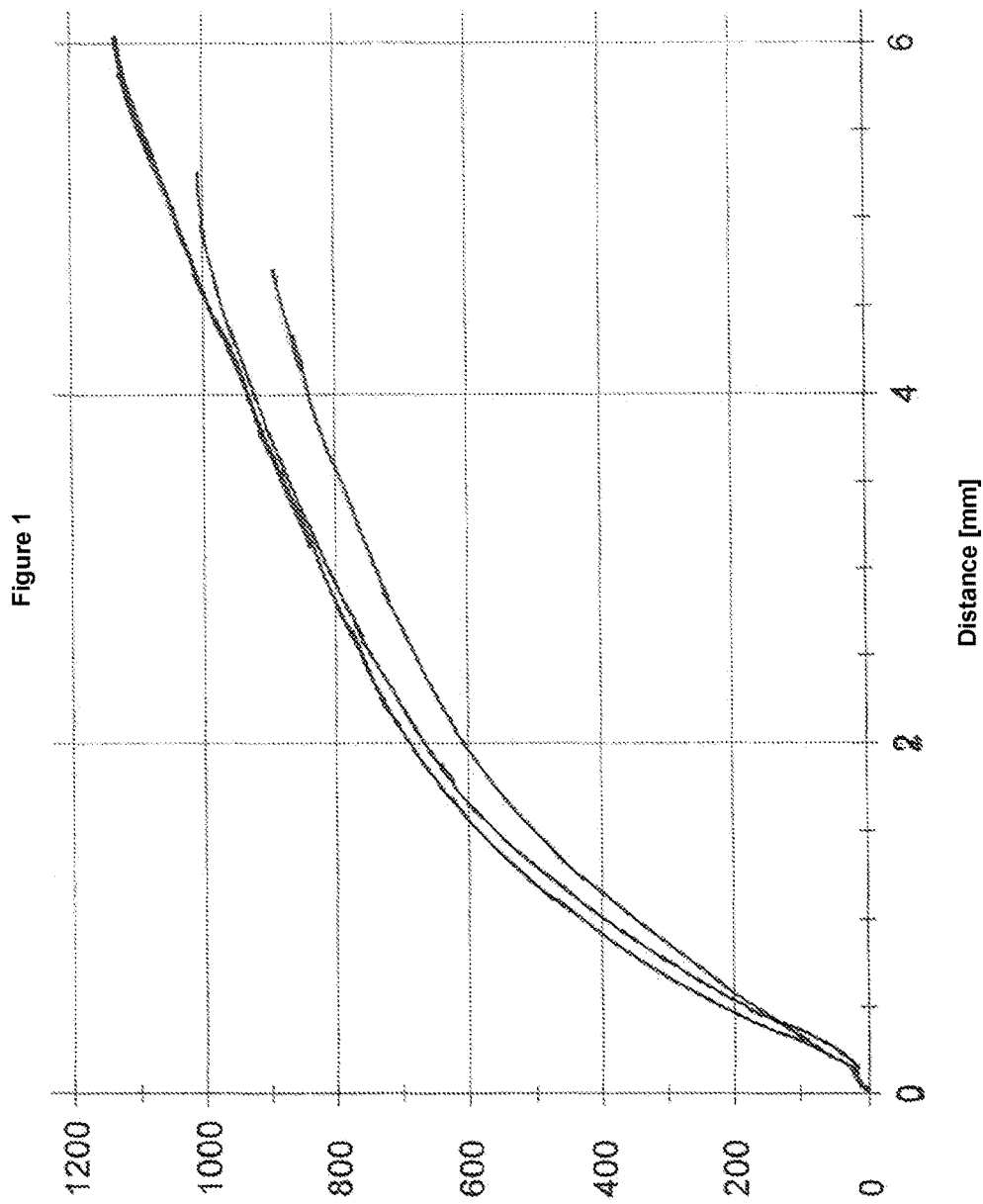
FIG. 1 shows the force-to-distance diagrams of the breaking strength measurements (120 mm/min) of the dosage form according to inventive example I-1 containing 10 wt.-% of Carbopol® 971P as physiologically acceptable polymer (B) and tramadol hydrochloride as ingredient (A).

A first aspect of the invention relates to a pharmaceutical dosage form exhibiting a breaking strength of at least 500 N, said dosage form containing
- a pharmacologically active ingredient (A);
- a physiologically acceptable polymer (B) obtainable by polymerization of a monomer composition comprising an ethylenically unsaturated monomer bearing an anionic functional group, in protonated form or a physiologically acceptable salt thereof; and
- a polyalkylene oxide (C) having a weight average molecular weight of at least 200,000 g/mol, wherein the content of the polyalkylene oxide (C) is at least 20 wt.-%, based on the total weight of the dosage form;

wherein the pharmacologically active ingredient (A) is present in a controlled-release matrix comprising the polymer (B) and the polyalkylene oxide (C).

The dosage form according to the invention contains one or more pharmacologically active ingredients (A).

There are generally no limitations as to the pharmacologically active ingredient (A) (pharmacologically active compound) which can be incorporated into the tablet of the invention.

In a preferred embodiment, the pharmaceutical dosage form contains only a single pharmacologically active ingredient (A). In another preferred embodiment, the pharmaceutical dosage form contains a combination of two or more pharmacologically active ingredients (A).

Preferably, pharmacologically active ingredient (A) is an active ingredient with potential for being abused. Active ingredients with potential for being abused are known to the person skilled in the art and comprise e.g. tranquillisers, stimulants, barbiturates, narcotics, opioids or opioid derivatives.

Preferably, the pharmacologically active ingredient (A) exhibits psychotropic action.

Preferably, the pharmacologically active ingredient (A) is selected from the group consisting of opiates, opioids, stimulants, tranquilizers, and other narcotics.

Particularly preferably, the pharmacologically active ingredient (A) is an opioid. According to the ATC index, opioids are divided into natural opium alkaloids, phenylpiperidine derivatives, diphenylpropylamine derivatives, benzomorphan derivatives, oripavine derivatives, morphinan derivatives and others.

The following opiates, opioids, tranquillisers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, faxeladol, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, Papaver somniferum, papavereturn, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclo-hex-1-enyl)-phenyl 2-(6-methoxy-naphthalen-2-yl) propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, and corresponding stereoisomers, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the acid or base addition salts thereof and solvates, e.g. hydrochlorides.

In a preferred embodiment the pharmaceutical dosage form according to the invention contains an opioid selected from the group consisting of DPI-125, M6G (CE-04-410), ADL-5859, CR-665, NRP290 and sebacoyl dinalbuphine ester.

In a preferred embodiment the pharmaceutical dosage form according to the invention contains one pharmacologically active compound (A) or more pharmacologically active compounds (A) selected from the group consisting of oxymorphone, hydromorphone and morphine.

In another preferred embodiment, the pharmacologically active compound (A) is selected from the group consisting of tapentadol, faxeladol and axomadol.

In still another preferred embodiment, the pharmacologically active compound (A) is selected from the group consisting of 1,1-(3-dimethylamino-3-phenylpentamethylene)-6-fluoro-1,3,4,9-tetrahydropyrano[3,4-b]indole, particularly its hemicitrate; 1,1-[3-dimethylamino-3-(2-thienyl)-pentamethylene]-1,3,4,9-tetrahydropyrano[3,4-b]indole, particularly its citrate; and 1,1-[3-dimethylamino-3-(2-thienyl)pentamethylene]-1,3,4,9-tetrahydropyrano[3,4-b]-6-fluoroindole, particularly its hemicitrate. These compounds are known from, e.g., WO 2004/043967, WO 2005/066183.

The pharmacologically active ingredient (A) may be present in form of a physiologically acceptable salt, e.g. physiologically acceptable acid addition salt.

Physiologically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like.

The pharmacologically active ingredient (A) is present in the dosage form in a therapeutically effective amount. The amount that constitutes a therapeutically effective amount varies according to the active ingredients being used, the condition being treated, the severity of said condition, the patient being treated, and whether the dosage form is designed for an immediate or retarded release.

The content of the pharmacologically active ingredient (A) in the pharmaceutical dosage form is not limited. The dose of the pharmacologically active ingredient (A) which is adapted for administration preferably is in the range of 0.1 mg to 500 mg, more preferably in the range of 1.0 mg to 400 mg, even more preferably in the range of 5.0 mg to 300 mg, and most preferably in the range of 10 mg to 250 mg. In a preferred embodiment, the total amount of the pharmacologically active ingredient (A) that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

Preferably, the content of the pharmacologically active ingredient (A) is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of pharmacologically active ingredient (A) is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of pharmacologically active ingredient (A) is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of pharmacologically active ingredient (A) is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

In a preferred embodiment, the pharmacologically active ingredient (A) is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, or 160±5 mg. In another preferred embodiment, the pharmacologically active ingredient (A) is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, or 160±2.5 mg.

In a particularly preferred embodiment, pharmacologically active ingredient (A) is tapentadol, preferably its HCl salt, and the pharmaceutical dosage form is adapted for administration once daily or twice daily. In this embodiment, pharmacologically active ingredient (A) is preferably contained in the pharmaceutical dosage form in an amount of from 25 to 250 mg.

In a particularly preferred embodiment, pharmacologically active ingredient (A) is oxymorphone, preferably its HCl salt, and the pharmaceutical dosage form is adapted for administration twice daily. In this embodiment, pharmacologically active ingredient (A) is preferably contained in the pharmaceutical dosage form in an amount of from 5 to 40 mg. In another particularly preferred embodiment, pharmacologically active ingredient (A) is oxymorphone, preferably its HCl salt, and the pharmaceutical dosage form is adapted for administration once daily. In this embodiment, pharmacologically active ingredient (A) is preferably contained in the pharmaceutical dosage form in an amount of from 10 to 80 mg.

In another particularly preferred embodiment, pharmacologically active ingredient (A) is oxycodone, preferably its HCl salt, and the pharmaceutical dosage form is adapted for administration twice daily. In this embodiment, pharmacologically active ingredient (A) is preferably contained in the pharmaceutical dosage form in an amount of from 5 to 80 mg. In another particularly preferred embodiment, pharmacologically active ingredient (A) is oxycodone, preferably its HCl, and the pharmaceutical dosage form is adapted for administration once daily. In this embodiment, pharmacologically active ingredient (A) is preferably contained in the pharmaceutical dosage form in an amount of from 10 to 320 mg.

In still another particularly preferred embodiment, pharmacologically active ingredient (A) is hydromorphone, preferably its HCl, and the pharmaceutical dosage form is adapted for administration twice daily. In this embodiment, pharmacologically active ingredient (A) is preferably contained in the pharmaceutical dosage form in an amount of from 2 to 52 mg. In another particularly preferred embodiment, pharmacologically active ingredient (A) is hydromorphone, preferably its HCl, and the pharmaceutical dosage form is adapted for administration once daily. In this embodiment, pharmacologically active ingredient (A) is preferably contained in the pharmaceutical dosage form in an amount of from 4 to 104 mg.

The pharmaceutical dosage form according to the invention is characterized by excellent storage stability. Preferably, after storage for 4 weeks at 40° C. and 75% rel. humidity, the content of pharmacologically active ingredient (A) amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active ingredient (A) in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers.

The dosage form according to the invention contains a physiologically acceptable polymer (B) obtainable by polymerization of a monomer composition comprising an ethylenically unsaturated monomer bearing an anionic functional group, in protonated form or a physiologically acceptable salt thereof. The active ingredient (A) is embedded into a controlled-release matrix comprising said physiologically acceptable polymer (B).

Preferably, the anionic functional group is selected from carboxyl groups, sulfonyl groups, sulfate groups, and phosphoryl groups.

Preferably, the monomer composition comprises an ethylenically unsaturated monomer selected from ethylenically unsaturated carboxylic acids, ethylenically unsaturated carboxylic acid anhydrides, ethylenically unsaturated sulfonic acids and mixtures thereof.

Preferred ethylenically unsaturated carboxylic acid and ethylenically unsaturated carboxylic acid anhydride monomers include the acrylic acids typified by acrylic acid itself, methacrylic acid, ethacrylic acid, alpha-chloracrylic acid, alpha-cyano acrylic acid, beta-methyl-acrylic acid (crotonic acid), alpha-phenyl acrylic acid, beta-acryloxy propionic acid, sorbic acid, alpha-chloro sorbic acid, angelic acid, cinnamic acid, p-chloro cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, tricarboxy ethylene and maleic acid anhydride.

Preferred ethylenically unsaturated sulfonic acids include aliphatic or aromatic vinyl sulfonic acids such as vinylsulfonic acid, allyl sulfonic acid, vinyltoluenesulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-acryloxy propyl sulfonic acid, 2-hydroxy-3-methacryloxy propyl sulfonic acid and 2-acrylamido-2-methyl propane sulfonic acid.

Preferably, the monomer composition comprises acrylic acid, methacrylic acid, and/or 2-acrylamido-2-methyl propane sulfonic acid. Acrylic acid is especially preferred.

The physiologically acceptable polymer (B) is obtainable by polymerization of such a monomer composition. This does not necessarily require that it has been obtained from such a monomer composition indeed. In other words, the physiologically acceptable polymer (B) is a polymer comprising at least one repeating unit which results from polymerization of an ethylenically unsaturated monomer bearing an anionic functional group, in protonated form or a physiologically acceptable salt thereof.

The physiologically acceptable polymer (B) may be linear or branched or cross-linked.

Preferably, physiologically acceptable polymer (B) is hydrophilic, more preferably water-soluble or water-swellable.

The physiologically acceptable polymer (B) may be a homopolymer or a copolymer. When polymer (B) is a homopolymer, it comprises a single type of repeating unit, i.e. is the polymerization product of a monomer composition comprising a single type of monomer. When polymer (B) is a copolymer, it may comprise two, three or more different repeating units, i.e. may be the polymerization product of a monomer composition comprising two, three or more different monomers.

In a preferred embodiment, the physiologically acceptable polymer (B) is a copolymer, comprising from about 50 mol-% to 99.999 mol-%, and more preferably from about 75 mol-% to 99.99 mol-% repeating units bearing anionic functional groups, preferably acid groups, more preferably carboxylic groups.

Preferably, the physiologically acceptable polymer (B) has an average equivalent weight of 76±50 g/mol, more preferably of 76±30 g/mol, still more preferably of 76±20 g/mol and most preferably of 76±10 g/mol per carboxyl group.

In a preferred embodiment, the monomer composition from which physiologically acceptable polymer (B) is derivable, further comprises a cross-linking agent, i.e. in this embodiment the physiologically acceptable polymer (B) is cross-linked.

Suitable cross-linking agents include
  compounds having at least two polymerizable double bonds, e.g. ethylenically unsaturated functional groups;
  compounds having at least one polymerizable double bond, e.g. an ethylenically unsaturated functional group, and at least one functional group that is capable of reacting with another functional group of one or more of the repeating units of polymer (B);
  compounds having at least two functional groups that are capable of reacting with other functional groups of one or more of the repeating units of polymer (B); and
  polyvalent metal compounds which can form ionic cross-linkages, e.g. through the anionic functional groups.

Cross-linking agents having at least two polymerizable double bonds, preferably allyl groups, are particularly preferred.

Cross-linking agents having at least two polymerizable double bonds include (i) di- or polyvinyl compounds such as divinylbenzene and divinyltoluene; (ii) di- or poly-esters of unsaturated mono- or poly-carboxylic acids with polyols including, for example, di- or triacrylic acid esters of polyols such as ethylene glycol, trimethylol propane, glycerine, or polyoxyethylene glycols; (iii) bisacrylamides such as N,N-methylenebisacrylamide; (iv) carbamyl esters that can be obtained by reacting polyisocyanates with hydroxyl group-containing monomers; (v) di- or poly-allyl ethers of polyols; (vi) di- or poly-allyl esters of polycarboxylic acids such as diallyl phthalate, diallyl adipate, and the like; (vii) esters of unsaturated mono- or poly-carboxylic acids with mono-allyl esters of polyols such as acrylic acid ester of polyethylene glycol monoallyl ether; and (viii) di- or triallyl amine.

In a preferred embodiment, divinyl glycol (1,5-hexadiene-3,4-diol) is contained as cross-linking agent, whereas allyl or vinyl derivatives of polyols, such as allylsucrose or allyl pentaerythritol, are less preferred. This embodiment is preferably realized by polyacrylic acid polymers of polycarbophil type according to USP.

In another preferred embodiment, allyl derivatives of polyols, such as allylsucrose or allyl pentaerythritol, are contained as cross-linking agent, whereas divinyl glycol (1,5-hexadiene-3,4-diol) is less preferred. This embodiment is preferably realized by polyacrylic acid polymers of carbomer type according to USP or Ph. Eur.

Cross-linking agents having at least one polymerizable double bond and at least one functional group capable of reacting with other functional groups of one or more of the repeating units of polymer (B) include N-methylol acrylamide, glycidyl acrylate, and the like.

Suitable cross-linking agents having at least two functional groups capable of reacting with other functional groups of one or more of the repeating units of polymer (B) include glyoxal; polyols such as ethylene glycol; polyamines such as alkylene diamines (e.g., ethylene diamine), polyalkylene polyamines, polyepoxides, di- or polyglycidyl ethers and the like.

Suitable polyvalent metal cross-linking agents which can form ionic cross-linkages include oxides, hydroxides and weak acid salts (e.g., carbonate, acetate and the like) of alkaline earth metals (e.g., calcium magnesium) and zinc, including, for example, calcium oxide and zinc diacetate.

Of all of these types of cross-linking agents, the most preferred for use herein are diol derivatives and polyol derivatives, more specifically those selected from the group consisting of allyl sucrose, allyl pentaerythritol, divinyl glycol, divinyl polyethylene glycol and (meth)acrylic acid esters of diols.

In a preferred embodiment, the monomer composition from which the physiologically acceptable polymer (B) is derivable comprises the cross-linking agent in an amount of at most 1.0 mol-%, more preferably at most 0.1 mol-%, even more preferably at most about 0.01 mol-%, and most preferably at most 0.005 mol-% based on all monomers forming polymer (B).

In a preferred embodiment, physiologically acceptable polymer (B) is a homopolymer of acrylic acid, optionally cross-linked, preferably with allyl sucrose or allyl pentaerythritol, in particular with allyl pentaerythritol. In another preferred embodiment, physiologically acceptable polymer (B) is a copolymer of acrylic acid and $C_{10}$-$C_{30}$-alkyl acrylate, optionally cross-linked, preferably with allyl pentaerythritol. In another preferred embodiment, physiologically acceptable polymer (B) is a so-called interpolymer, namely a homopolymer of acrylic acid, optionally cross-linked, preferably with allyl sucrose or allyl pentaerythritol; or a copolymer of acrylic acid and $C_{10}$-$C_{30}$-alkyl acrylate, optionally cross-linked, preferably with allyl pentaerythritol; which contain a block copolymer of polyethylene glycol and a long chain alkyl acid, preferably a $C_8$-$C_{30}$-alkyl acid. Polymers of this type are commercially available, e.g. under the trademark Carbopol®.

In another preferred embodiment, polymer (B), preferably the dosage form according to the invention does not contain a block copolymer of polyethylene glycol and an alkyl acid ester.

When polymer (B) is an interpolymer, it preferably has a viscosity in 1.0 wt.-% solution at pH 7.5 within the range of from 47,000 to 77,000 mPa·s, more preferably 52,000 to 72,000 mPa·s, still more preferably 57,000 to 67,000 mPa·s.

Preferably, at least some of the anionic functional groups contained in the physiologically acceptable polymer (B) are present in neutralized form, i.e. they are not present in their protonated forms, but are salts with salt-forming cations instead. Suitable salt-forming cations include alkali metal, ammonium, substituted ammonium and amines. More preferably, at least some of the anionic functional groups, e.g. carboxylate and/or sulfonate anions, are salts of sodium or potassium cations.

This percentage of neutralized anionic functional groups, based on the total amount of anionic functional groups, is referred to herein as the "degree of neutralization." In a preferred embodiment, the degree of neutralization is within the range of from 2.5±2.4%, more preferably 2.5±2.0%, still more preferably 2.5±1.5%, yet more preferably 2.5±1.0%, and most preferably 2.5±0.5%. In another preferred embodiment, the degree of neutralization is within the range of 35±30%, more preferably 35±25%, still more preferably 35±20%, yet more preferably 35±15%, most preferably 35±10%, and in particular 35±5%. In yet another preferred embodiment, the degree of neutralization is in the range of 65±30%, more preferably 65±25%, still more preferably 65±20%, yet more preferably 65±15%, most preferably 65±10%, and in particular 65±5%.

Preferably, the pharmaceutical dosage form according to the invention contains a physiologically acceptable polymer (B) which—at a content of at least 10 wt.-% based on the total weight of the pharmaceutical dosage form—causes a retardation of the in vitro release profile. A skilled person can easily determine by routine experimentation which physiologically acceptable polymers (B) satisfy this requirement.

In a preferred embodiment, the pharmaceutical dosage form according to the invention contains a physiologically acceptable polymer (B) which—at a content of at least 10 wt.-% based on the total weight of the pharmaceutical dosage form—causes a retardation of the in vitro release profile compared to a pharmaceutical dosage form not containing said amount of said physiologically acceptable polymer (B) so that after 360 min the in vitro release is relatively retarded by at least 2%, more preferably at least 4%, still more preferably at least 6%, yet more preferably at least 8%, most preferably at least 10% and in particular at least 12%.

Preferably, the in vitro release is measured in accordance with the conditions specified in the experimental section. For example, when a comparative dosage form not containing said amount of said physiologically acceptable polymer (B) releases in vitro after 360 min e.g. 34.7% of the pharmacologically active ingredient, the pharmaceutical dosage form according to the invention preferably releases under the same conditions at most 32.7% of the pharmacologically active ingredient (Δ 2%).

In another preferred embodiment, the pharmaceutical dosage form according to the invention contains a physiologically acceptable polymer (B) which—at a content of at least 10 wt.-% based on the total weight of the pharmaceutical dosage form—causes a retardation of the in vitro release profile compared to a pharmaceutical dosage form not containing said amount of said physiologically acceptable polymer (B) so that after 720 min the in vitro release is relatively retarded by at least 2%, more preferably at least 4%, still more preferably at least 6%, yet more preferably at least 8%, most preferably at least 10% and in particular at least 12%.

The content of physiologically acceptable polymer (B) ranges preferably from 0.1 wt.-% to 95 wt.-%, more preferably from 1.0 wt.-% to 80 wt.-%, still more preferably from 2.0 wt.-% to 50 wt.-%, and most preferably from 5 wt.-% to 30% wt.-%, and in particular 9 wt.-% to 21 wt.-%, based on the total weight of the pharmaceutical dosage form.

In a preferred embodiment, the content of physiologically acceptable polymer (B) amounts to 0.5 to 25 wt.-%, more preferably 1.0 to 20 wt.-%, still more preferably 2.0 to 22.5 wt.-%, yet more preferably 3.0 to 20 wt.-% and most preferably 4.0 to 17.5 wt.-% and in particular 5.0 to 15 wt.-%, based on the total weight of the pharmaceutical dosage form.

In a preferred embodiment, the content of physiologically acceptable polymer (B) is within the range of 10±9 wt.-%, more preferably 10±8 wt.-%, still more preferably 10±7 wt.-%, yet more preferably 10±6 wt.-%, most preferably 10±5 wt.-%, and in particular 10±2.5 wt.-%, based on the total weight of the pharmaceutical dosage form.

In still another preferred embodiment, the content of physiologically acceptable polymer (B) is within the range of 15±14 wt.-%, more preferably 15±12.5 wt.-%, still more preferably 15±10 wt.-%, yet more preferably 15±7.5 wt.-%, most preferably 15±5 wt.-%, and in particular 15±2.5 wt.-%, based on the total weight of the pharmaceutical dosage form.

In still another preferred embodiment, the content of physiologically acceptable polymer (B) is within the range of 20±15 wt.-%, more preferably 20±12.5 wt.-%, still more preferably 20±10 wt.-%, yet more preferably 20±7.5 wt.-%, most preferably 20±5 wt.-%, and in particular 20±2.5 wt.-%, based on the total weight of the pharmaceutical dosage form.

In a preferred embodiment, the physiologically acceptable polymer (B) has a weight average molecular weight ($M_W$) of at least 100,000 g/mol, preferably at least 200,000 g/mol or at least 400,000 g/mol, more preferably in the range of about 500,000 g/mol to about 5,000,000 g/mol, and most preferably in the range of about 600,000 g/mol to about 2,000,000 g/mol. Suitable methods to determine $M_W$ are known to a person skilled in the art. For instance, $M_W$ can be determined by gel permeation chromatography (GPC).

In a preferred embodiment, the $pK_A$ of the physiologically acceptable polymer (B) is 6.0±2.0, more preferably 6.0±1.5, even more preferably 6.0±1.0, and most preferably 6.0±0.5. In another preferred embodiment, the $pK_A$ of the physiologically acceptable polymer (B) is 7.0±2.0, more preferably 7.0±1.5, even more preferably 7.0±1.0, and most preferably 7.0±0.5. In still another preferred embodiment, the $pK_A$ of the physiologically acceptable polymer (B) is 8.0±2.0, more preferably 8.0±1.5, even more preferably 8.0±1.0, and most preferably 8.0±0.5.

In a preferred embodiment, the pH (in 1 wt % aqueous dispersion) of the physiologically acceptable polymer (B) is 3.0±3.0, more preferably 3.0±2.0, even more preferably 3.0±1.5, and most preferably 3.0±1.0.

In another preferred embodiment, the pH (in 1 wt % aqueous dispersion) of the physiologically acceptable polymer (B) is 6.0±3.0, more preferably 6.0±2.0, even more preferably 6.0±1.5, and most preferably 6.0±1.0.

The physiologically acceptable polymer (B) preferably exhibits a viscosity of 2,000 to 100,000 mPa s (cp), more preferably 3,000 to 80,000 mPa s, still more preferably 4,000 to 60,000 mPa s, measured by means of a Brookfield viscometer (RVF, 20 rpm) in a 0.5 wt.-% aqueous solution at pH 7.5 and 25° C.

In a preferred embodiment, the physiologically acceptable polymer (B) exhibits a viscosity of more than 10,000 mPa s (cp), preferably at least 11,000 mPa s, more preferably at least 15,000 mPa s, still more preferably at least 20,000 mPa s or at least 30,000 mPa s, measured by means of a Brookfield viscometer (RVF, 20 rpm) in a 0.5 wt.-% aqueous solution at pH 7.5 and 25° C.

In a preferred embodiment, physiologically acceptable polymer (B) is homogeneously distributed in the pharmaceutical dosage form according to the invention. Preferably, the pharmacologically active ingredient (A) and physiologically acceptable polymer (B) are intimately homogeneously distributed in the pharmaceutical dosage form so that the pharmaceutical dosage form does not contain any segments where either pharmacologically active ingredient (A) is present in the absence of physiologically acceptable polymer (B) or where physiologically acceptable polymer (B) is present in the absence of pharmacologically active ingredient (A).

When the pharmaceutical dosage form is film coated, the physiologically acceptable polymer (B) is preferably homogeneously distributed in the core of the pharmaceutical dosage form, i.e. the film coating preferably does not contain physiologically acceptable polymer (B). Nonetheless, the film coating as such may of course contain one or more polymers, which however, preferably differ from the physiologically acceptable polymer (B) contained in the core.

The pharmaceutical dosage form according to the invention contains a polyalkylene oxide (C). The active ingredient (A) is embedded into a controlled-release matrix comprising said polyalkylene oxide (C) and the physiologically acceptable polymer (B).

Preferably, the polyalkylene oxide (C) is selected from polymethylene oxide, polyethylene oxide and polypropylene oxide, or copolymers thereof.

The polyalkylene oxide (C) has a weight average molecular weight ($M_W$) and preferably, also a viscosity average molecular weight ($M_\eta$) of at least 200,000 or preferably at least 500,000 g/mol, preferably at least 1,000,000 g/mol or at least 2,500,000 g/mol, more preferably in the range of about 1,000,000 g/mol to about 15,000,000 g/mol, and most preferably in the range of about 5,000,000 g/mol to about 10,000,000 g/mol. Suitable methods to determine $M_W$ and $M_\eta$ are known to a person skilled in the art. $M_\eta$ is preferably determined by rheological measurements, whereas $M_W$ can be determined by gel permeation chromatography (GPC).

Preferably, the content of the polyalkylene oxide (C) is within the range of from 20 to 99 wt.-%, more preferably 25 to 95 wt.-%, still more preferably 30 to 90 wt.-%, yet more preferably 30 to 85 wt.-%, most preferably 30 to 80 wt.-% and in particular 30 to 75 wt.-% or 45 to 70 wt.-%, based on the total weight of the pharmaceutical dosage form. The content of the polyalkylene oxide is at least 20 wt.-%, preferably at least 25 wt.-%, more preferably at least 30 wt.-%, yet more preferably at least 35 wt.-% and in particular at least 40 wt.-%.

In a preferred embodiment, the overall content of polyalkylene oxide (C) is within the range of 25±20 wt.-%, more preferably 25±15 wt.-%, most preferably 25±10 wt.-%, and in particular 25±5 wt.-%. In another preferred embodiment, the overall content of polyalkylene oxide (C) is within the range of 35±20 wt.-%, more preferably 35±15 wt.-%, most preferably 35±10 wt.-%, and in particular 35±5 wt.-%. In still another preferred embodiment, the overall content of polyalkylene oxide (C) is within the range of 45±20 wt.-%, more preferably 45±15 wt.-%, most preferably 45±10 wt.-%, and in particular 45±5 wt.-%. In yet another preferred embodiment, the overall content of polyalkylene oxide (C) is within the range of 55±20 wt.-%, more preferably 55±15 wt.-%, most preferably 55±10 wt.-%, and in particular 55±5 wt.-%. In a further preferred embodiment, the overall content of polyalkylene oxide (C) is within the range of 65±20 wt.-%, more preferably 65±15 wt.-%, most preferably 65±10 wt.-%, and in particular 65±5 wt.-%. In still a further a preferred embodiment, the overall content of polyalkylene oxide (C) is within the range of 75±20 wt.-%, more preferably 75±15 wt.-%, most preferably 75±10 wt.-%, and in particular 75±5 wt.-%. In a still further a preferred embodiment, the overall content of polyalkylene oxide (C) is within the range of 80±15 wt.-%, more preferably 80±10 wt.-%, and most preferably 80±5 wt.-%.

Polyalkylene oxide (C) may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the pharmaceutical dosage form is at least 200,000 g/mol. Thus, polyalkylene glycols, if any, are preferably not taken into consideration when determining the weight average molecular weight of polyalkylene oxide (C).

In a preferred embodiment, polyalkylene oxide (C) is homogeneously distributed in the pharmaceutical dosage form according to the invention. Preferably, the pharmacologically active ingredient (A) and polyalkylene oxide (C) are intimately homogeneously distributed in the pharmaceutical dosage form so that the pharmaceutical dosage form does not contain any segments where either pharmacologically active ingredient (A) is present in the absence of polyalkylene oxide (C) or where polyalkylene oxide (C) is present in the absence of pharmacologically active ingredient (A).

When the pharmaceutical dosage form is film coated, the polyalkylene oxide (C) is preferably homogeneously distributed in the core of the pharmaceutical dosage form, i.e. the film coating preferably does not contain polyalkylene oxide (C). Nonetheless, the film coating as such may of course contain one or more polymers, which however, preferably differ from the polyalkylene oxide (C) contained in the core.

The polyalkylene oxide (C) may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) poly(hydroxyvaleric acid); polycaprolactone, polyvinyl alcohol, polyesteramide, polyethylene succinate, polylactone, polyglycolide, polyurethane, polyamide, polylactide, polyacetal (for example poly-saccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, the molecular weight dispersity $M_w/M_n$ of polyalkylene oxide (C) is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide (C) preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt.-% aqueous solution using the stated viscosimeter (spindle no. 2/rotational speed 2 rpm).

In a preferred embodiment, the relative weight ratio of polymer (C) to polymer (B) is within the range of from 10:1 to 1:1, more preferably 9:1 to 1.25:1, still more preferably 8:1 to 1.5:1, yet more preferably 7:1 to 1.75:1, most preferably 6.5:1 to 2:1 and in particular 6:1 to 2.5:1.

In another preferred embodiment the relative weight ratio of polyalkylene oxide (C) to polymer (B) is within the range of from 20:1 to 1:20, more preferably 10:1 to 1:10, still more preferably 7:1 to 1:5, yet more preferably 5:1 to 1:1, most preferably 4:1 to 1, 5:1 and in particular 3:1 to 2:1. In a preferred embodiment, the relative weight ratio of polyalkylene oxide (C) and polymer (B) is within the range of from 10:1 to 5:1, more preferably 8:1 to 5:1, most preferably 7:1 to 5:1.

Preferably, the relative weight ratio of the polyalkylene oxide (C) to the pharmacologically active ingredient (A) is at least 0.5:1, more preferably at least 1:1, at least 2:1, at least 3:1, at least 4:1, at least 5:1, at least 6:1, at least 7:1, at least 8:1 or at least 9:1; still more preferably at least 10:1 or at least 15:1, yet more preferably at least 20:1, most preferably at least 30:1 and in particular at least 40:1. In a preferred embodiment, the relative weight ratio of the polyalkylene oxide (C) to the pharmacologically active ingredient (A) is within the range of from 3:1 to 50:1, more preferably 3:1 to 40:1 and in particular 3:1 to 30:1.

Besides the pharmacologically active ingredient (A), the physiologically acceptable polymer (B) and the polyalkylene oxide (C) the pharmaceutical dosage form according to the invention may contain further ingredients, e.g. one or more conventional pharmaceutical excipient(s), e.g. fillers, glidants, binding agents, granulating agents, anti-caking agents, lubricants, flavors, dyes, and/or preservatives.

Preferably, the pharmaceutical dosage form contains at least one lubricant.

Especially preferred lubricants are selected from
magnesium stearate and stearic acid;
glycerides of fatty acids, including monoglycerides, diglycerides, triglycerides, and mixtures thereof; preferably of $C_6$ to $C_{22}$ fatty acids; especially preferred are partial glycerides of the $C_{16}$ to $C_{22}$ fatty acids such as glycerol behenat, glycerol palmitostearate and glycerol monostearate;
polyoxyethylene glycerol fatty acid esters, such as mixtures of mono-, di- and triesters of glycerol and di- and monoesters of macrogols having molecular weights within the range of from 200 to 4000 g/mol, e.g., macrogolglycerolcaprylocaprate, macrogolglycerollaurate, macrogolglycerolococoate, macrogolglycerollinoleate, macrogol-20-glycerolmonostearate, macrogol-6-glycerolcaprylocaprate, macrogolglycerololeate; macrogolglycerolstearate, macrogolglycerolhydroxystearate, and macrogolglycerolrizinoleate;

polyglycolyzed glycerides, such as the one known and commercially available under the trade name "Labrasol";

fatty alcohols that may be linear or branched, such as cetylalcohol, stearylalcohol, cetylstearyl alcohol, 2-octyldodecane-1-ol and 2-hexyldecane-1-ol;

polyethylene glycols having a molecular weight between 10.000 and 60.000 g/mol; and natural semi-synthetic or synthetic waxes, preferably waxes with a softening point of at least 50° C., more preferably 60° C., and in particular carnauba wax and bees wax.

Preferably, the amount of the lubricant ranges from 0.1 wt.-% to about 30 wt.-%, more preferably in the range of 1.0 wt.-% to about 25 wt.-%, most preferably in the range of 2.0 wt.-% to about 20 wt.-%, and in particular in the range of 5 wt.-% to about 15 wt.-%.

In a preferred embodiment, the relative weight ratio of the polyalkylene oxide (C) to the lubricant is within the range of 4.5±2:1, more preferably 4.5±1.5:1, still more preferably 4.5±1:1, yet more preferably 4.5±0.5:1, most preferably 4.5±0.2:1, and in particular 4.5±0.1:1.

Preferably, the pharmaceutical dosage form further comprises a plasticizer. The plasticizer improves the processability of the polyalkylene oxide (C) and optionally, also of the physiologically acceptable polymer (B). A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.5 to 30 wt.-%, more preferably 1.0 to 25 wt.-%, still more preferably 2.5 wt.-% to 22.5 wt.-%, yet more preferably 5.0 wt.-% to 20 wt.-%, most preferably 7.5 to 20 wt.-% and in particular 10 wt.-% to 17.5 wt.-%, based on the total weight of the pharmaceutical dosage form.

In a preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the plasticizer is a polyalkylene glycol having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

In a preferred embodiment, the relative weight ratio of the polyalkylene oxide (C) to the polyalkylene glycol is within the range of 4.2±2:1, more preferably 4.2±1.5:1, still more preferably 4.2±1:1, yet more preferably 4.2±0.5:1, most preferably 4.2±0.2:1, and in particular 4.2±0.1:1. This ratio satisfies the requirements of relative high polyalkylene oxide (C) content and good extrudability.

When manufacturing the dosage forms from slices that are obtained by cutting the extrudate strand, the weight of the slices determines the weight of the resulting dosage form. Pronounced variation in weight of these slices results in an accordant weight deviation of dosage forms from the target weight. The weight variation of slices depends strongly on the surface properties of the extrudate strand. A strand with a thoroughly smooth surface allows the generation of slices exhibiting a low weight variation. In contrast, a wavy or shark skinning strand results in slices exhibiting a higher weight variation thereby increasing the number of rejects. It has been surprisingly found that the surface properties of the extrudate strand can be triggered by the polyalkylene oxide:polyalkylene glycol weight ratio.

Preferably, the pharmaceutical dosage form further comprises an anti-oxidant. Suitable oxidants include ascorbic acid, butylated hydroxyanisole (BHA), butylated hydroxytoluene (BHT), salts of ascorbic acid, monothioglycerol, phosphorous acid, vitamin C, vitamin E and the derivatives thereof, coniferyl benzoate, nordihydroguajaretic acid, gallus acid esters, sodium bisulfite, particularly preferably butylhydroxytoluene or butylhydroxyanisole and α-tocopherol. The antioxidant is preferably used in quantities of 0.01 wt.-% to 10 wt.-%, more preferably of 0.03 wt.-% to 5 wt.-%, most preferably of 0.05 wt.-% to 2.5 wt.-% relative to the total weight of the pharmaceutical dosage form.

In a preferred embodiment, the pharmaceutical dosage form further comprises an acid, preferably citric acid. The amount of acid is preferably in the range of 0.01 wt.-% to about 20 wt.-%, more preferably in the range of 0.02 wt.-% to about 10 wt.-%, and still more preferably in the range of 0.05 wt.-% to about 5 wt.-%, and most preferably in the range of 0.1 wt.-% to about 1.0 wt.-%.

In a preferred embodiment, the pharmaceutical dosage form further comprises another polymer which is preferably selected from cellulose esters and cellulose ethers, in particular hydroxypropyl methylcellulose (HPMC).

Other preferred polymers are polyvinyl caprolactam-polyvinyl acetate-polyethylene glycol graft co-polymers, such as the one commercially available under the trade name Soluplus®.

The amount of the further polymer, preferably hydroxypropyl methylcellulose, preferably ranges from 0.1 wt.-% to about 30 wt.-%, more preferably in the range of 1.0 wt.-% to about 20 wt.-%, most preferably in the range of 2.0 wt.-% to about 15 wt.-%, and in particular in the range of 7.5 wt.-% to about 12.5 wt.-%.

In a preferred embodiment, the relative weight ratio of the polyalkylene oxide (C) to the further polymer is within the range of 4.5±2:1, more preferably 4.5±1.5:1, still more preferably 4.5±1:1, yet more preferably 4.5±0.5:1, most preferably 4.5±0.2:1, and in particular 4.5±0.1:1.

In another preferred embodiment, the pharmaceutical dosage form according to the invention does not contain any further polymer besides the physiologically acceptable polymer (B), the polyalkylene oxide (C) and optionally, the polyethylene glycol.

The pharmaceutical dosage form according to the invention is preferably an oral dosage form, particularly a tablet. It is also possible, however, to administer the pharmaceutical dosage form via different routes and thus, the pharmaceutical dosage form may alternatively be adapted for buccal, lingual, rectal or vaginal administration. Implants are also possible. Preferably, the pharmaceutical dosage form is monolithic. Preferably, the pharmaceutical dosage form is neither in film form, nor multi-particulate.

In a preferred embodiment, the pharmaceutical dosage form according to the invention is a round tablet. Tablets of this embodiment preferably have a diameter in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

In another preferred embodiment, the pharmaceutical dosage form according to the invention is an oblong tablet. Tablets of this embodiment preferably have a lengthwise extension (longitudinal extension) of about 1 mm to about 30 mm, in particular in the range of about 2 mm to about 25 mm, more in particular about 5 mm to about 23 mm, even more in particular about 7 mm to about 20 mm; a width in the range of about 1 mm to about 30 mm, in particular in the range of about 2 mm to about 25 mm, more in particular about 5 mm to about 23 mm, even more in particular about 7 mm to about 13 mm; and a thickness in the range of about 1.0 mm to about 12 mm, in particular in the range of about 2.0 mm to about 10 mm, even more in particular from 3.0 mm to about 9.0 mm, even further in particular from about 4.0 mm to about 8.0 mm.

The pharmaceutical dosage form according to the invention has preferably a weight in the range of 0.01 to 1.5 g, more preferably in the range of 0.05 to 1.2 g, still more preferably in the range of 0.1 g to 1.0 g, yet more preferably in the range of 0.2 g to 0.9 g, and most preferably in the range of 0.25 g to 0.8 g.

The pharmaceutical dosage form according to the invention is preferably prepared by melt-extrusion, although also other methods of thermoforming may be used in order to manufacture the pharmaceutical dosage form according to the invention such as press-molding at elevated temperature or heating of tablets that were manufactured by conventional compression in a first step and then heated above the softening temperature of the polymer in the tablet in a second step to form hard tablets. In this regards, thermoforming means the forming, or molding of a mass after the application of heat. In a preferred embodiment, the pharmaceutical dosage form is thermoformed by hot-melt extrusion.

In a preferred embodiment, the pharmaceutical dosage form is prepared by hot melt-extrusion, preferably by means of a twin-screw-extruder. Melt extrusion preferably provides a melt-extruded strand that is preferably cut into monoliths, which are then compressed and formed into tablets. In this regard, the term "tablets" is preferably not to be understood as dosage forms being made by compression of powder or granules (compressi) but rather, as shaped extrudates. Preferably, compression is achieved by means of a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C. The strands obtained by way of extrusion can either be subjected to the compression step as such or can be cut prior to the compression step. This cutting can be performed by usual techniques, for example using rotating knives or compressed air. Alternatively, the shaping can take place as described in EP-A 240 906 by the extrudate being passed between two counter-rotating calender rolls and being shaped directly to tablets. It is of course also possible to subject the extruded strands to the compression step or to the cutting step when still warm, that is more or less immediately after the extrusion step. The extrusion is preferably carried out by means of a twin-screw extruder.

The pharmaceutical dosage form of the invention can optionally be provided, partially or completely, with a conventional coating. The dosage forms of the present invention are preferably film coated with conventional film coating compositions.

Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinyl-acetatephthalate, polyvinyl alcohol, polyvinylacetate; and natural film formers, such as shellack.

In a particularly preferred embodiment, the coating is water-soluble. In a preferred embodiment, the coating is based on polyvinyl alcohol, such as polyvinyl alcohol-part hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

The coating can also be applied e.g. to improve the aesthetic impression and/or the taste of the dosage forms and the ease with which they can be swallowed. Coating the dosage forms of the present invention can also serve other purposes, e.g. improving stability and shelf-life. Suitable coating formulations comprise a film forming polymer such as, for example, polyvinyl alcohol or hydroxypropyl methylcellulose, e.g. hypromellose, a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Optionally, the coating can contain a therapeutically effective amount of one or more active ingredients to provide for an immediate release of said active ingredient (A) and thus for an immediate relief of the symptoms treated by said active ingredient (A). Coated dosage forms of the present invention are preferably prepared by first making the cores and subsequently coating said cores using conventional techniques, such as coating in a coating pan.

According to the invention, the active ingredient (A) is embedded in a controlled-release matrix comprising physiologically acceptable polymer (B) and polyalkylene oxide (C).

Controlled release of an active ingredient from an oral dosage form is known to a person skilled in the art. For the purpose of the specification, controlled release encompasses delayed release, retarded release, sustained release, prolonged release, and the like.

Controlled or prolonged release is understood according to the invention preferably to mean a release profile in which the pharmacologically active ingredient (A) is released over a relatively long period with reduced intake frequency with the purpose of extended therapeutic action. Preferably, the meaning of the term "prolonged release" is in accordance with the European guideline on the nomenclature of the release profile of pharmaceutical dosage forms (CHMP). This is achieved in particular with peroral administration. The expression "at least partially delayed or prolonged release" covers according to the invention any pharmaceutical dosage forms which ensure modified release of the opioids (A) contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release time profile of a controlled release form may be modified e.g. as follows: extended release, repeat action release, prolonged release and sustained release.

For the purpose of the specification "controlled release" preferably means a product in which the release of active compound over time is controlled by the type and composition of the formulation. For the purpose of the specification "extended release" preferably means a product in which the release of active compound is delayed for a finite lag time, after which release is unhindered. For the purpose of the specification "repeat action release" preferably means a product in which a first portion of active compound is released initially, followed by at least one further portion of active compound being released subsequently. For the purpose of the specification "prolonged release" preferably means a product in which the rate of release of active compound from the formulation after administration has been reduced over time, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and Eur. Ph.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active ingredient (A). Further preferred release profiles $R_1$ to $R_6$ are summarized in the table here below [all data in wt.-% of released pharmacologically active ingredient (A)]:

| time | $R_1$ | $R_2$ | $R_3$ | $R_4$ | $R_5$ | $R_6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1440 min | 50-100 | 50-100 | >90 | | | |
| 2160 min | >80 | >80 | | | | |

Further preferred release profiles $R_1$ to $R_6$ are summarized in the table here below [all data in wt.-% of released pharmacologically active ingredient (A)]:

| time | $R_7$ | $R_8$ | $R_9$ | $R_{10}$ | $R_{11}$ | $R_{12}$ |
|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 |
| 60 min | 27.0 ± 8.0 | 27.0 ± 7.0 | 27.0 ± 6.0 | 27.0 ± 5.0 | 27.0 ± 4.0 | 27.0 ± 3.0 |
| 120 min | 41.5 ± 9.5 | 41.5 ± 8.5 | 41.5 ± 7.5 | 41.5 ± 6.5 | 41.5 ± 5.5 | 41.5 ± 4.5 |
| 240 min | 64.5 ± 12.5 | 64.5 ± 11.5 | 64.5 ± 10.5 | 64.5 ± 9.5 | 64.5 ± 8.5 | 64.5 ± 7.5 |
| 480 min | 88.0 ± 12.0 | 88.0 ± 11.0 | 88.0 ± 10.0 | 88.0 ± 9.0 | 88.0 ± 8.0 | 88.0 ± 7.0 |
| 720 min | 96.0 ± 9.0 | 96.0 ± 8.0 | 96.0 ± 7.0 | 96.0 ± 6.0 | 96.0 ± 5.0 | 96.0 ± 4.0 |
| 840 min | 97.5 ± 7.5 | 97.5 ± 6.5 | 97.5 ± 5.5 | 97.5 ± 4.5 | 97.5 ± 3.5 | 97.5 ± 2.5 |

Preferably, the release profile of the pharmaceutical dosage form according to the present invention is stable upon storage, preferably upon storage at elevated temperature, e.g. 40° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active ingredient (A) that was originally contained in the pharmaceutical dosage form.

Suitable in vitro conditions are known to the skilled artisan. In this regard it can be referred to, e.g., the Eur. Ph. Preferably, the release profile is measured under the following conditions: Paddle apparatus equipped with sinker, 50 rpm, 37±5° C., 900 mL simulated intestinal fluid pH 6.8 (phosphate buffer) or pH 4.5. In a preferred embodiment, to rotational speed of the paddle is increased to 100 rpm.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

Preferably the pharmaceutical dosage form according to the invention releases after 5 h at most 99%, more preferably at most 90%, still more preferably at most 75%, and most preferably at most 60% of the active ingredient (A).

The physiologically acceptable polymer (B) is preferably hydrophilic, meaning that a matrix comprising polymer (B) and polyalkylene oxide (C) tends to swell upon contact with aqueous fluids following administration, and preferably results in a viscous, drug release regulating gel layer.

In a preferred embodiment, the matrix comprising the physiologically acceptable polymer polymer (B) and the polyalkylene oxide (C) contains polymer (B) in such a quantity that:
a) under in vitro conditions the release of the active ingredient (A) is additionally retarded; and/or
b) upon exposure to water the hydration process of the pharmaceutical dosage form is accelerated; during this process the pharmaceutical dosage form forms a water-containing shell (gel) around a dry core in such a way that preferably during the first 270 minutes the core/gel ratio decreases while the volume of the said dosage form increases not more than 20%, in particular not more than 10% of the original volume of the dosage form;
in each case compared to a thus identical, comparative pharmaceutical dosage form wherein the physiologically acceptable polymer (B) is substituted with the corresponding amount of hydroxylpropyl methyl cellulose (HPMC).

In a particular preferred embodiment,
the pharmaceutical dosage form is thermoformed, preferably by hot melt-extrusion; and/or
the pharmaceutical dosage form exhibits a breaking strength of at least 1500 N; and/or
the pharmaceutical dosage form is adapted for administration once-daily, twice daily or thrice-daily; and/or
the pharmacologically active ingredients (A) is selected from the group of opioids and opiates; and or
polymer (B) is obtainable by polymerization of a monomer composition comprising a cross-linking agent and a monomer, selected from ethylenically unsaturated carboxylic acids and acid anhydrides, ethylenically unsaturated sulfonic acids and mixtures thereof; and/or
the content of polymer (B) ranges from 2.0 wt.-% to 50 wt.-%; and/or
the polyalkylene oxide (C) is selected from polymethylene oxide, polyethylene oxide and polypropylene oxide, or copolymers thereof; having a weight average molecular weight ($M_W$) of at least 500,000 g/mol, more preferably within the range of from 1,000,000 g/mol to 10,000,000 g/mol; and/or
the content of polyalkylene oxide (C) is at least 30 wt.-%, based on the total weight of the dosage form.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen and ihre Inhaltsstoffe" by Prof. Dr. Hildebert Wagner, 2nd, revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredient (A), preferably no antagonists against psychotropic substances, in particular no antagonists against opioids (A). Antagonists suitable for a given pharmacologically active ingredient (A) are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen and ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference.

Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredient (A), nor emetics, nor bitter substances.

The pharmaceutical dosage from according to the invention has a breaking strength of at least 500 N.

The pharmaceutical dosage form according to the invention is preferably tamper-resistant. Preferably, tamper-resistance is achieved based on the mechanical properties of the pharmaceutical dosage form so that comminution is avoided or at least substantially impeded. According to the invention, the term comminution means the pulverization of the pharmaceutical dosage form using conventional means usually available to an abuser, for example a pestle and mortar, a hammer, a mallet or other conventional means for pulverizing under the action of force. Thus, tamper-resistance preferably means that pulverization of the pharmaceutical dosage form using conventional means is avoided or at least substantially impeded.

Preferably, the mechanical properties of the pharmaceutical dosage form according to the invention, particularly its breaking strength, substantially rely on the presence and spatial distribution of polymer (B) and polyalkylene oxide (C), although their mere presence does typically not suffice in order to achieve said properties. The advantageous mechanical properties of the pharmaceutical dosage form according to the invention may not automatically be achieved by simply processing pharmacologically active ingredient (A), polymer (B), polyalkylene oxide (C), and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

In general, the dosage forms exhibiting the desired properties may be obtained only if, during preparation of the dosage form,
suitable components
in suitable amounts
are exposed to
a sufficient pressure
at a sufficient temperature
for a sufficient period of time.

Thus, regardless of the apparatus used, the process protocols must be adapted in order to meet the required criteria. Therefore, the breaking strength is separable from the composition.

The pharmaceutical dosage form according to the invention has a breaking strength of at least 500 N, preferably at least 600 N, more preferably at least 700 N, still more preferably at least 800 N, yet more preferably at least 1000 N, most preferably at least 1250 N and in particular at least 1500 N.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the pharmaceutical dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The pharmaceutical dosage forms according to the invention are distinguished from conventional pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active compound (A) in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10× Diameter Of The Tablet [in mm]. Thus, according to said empirical formula, a round tablet having a breaking strength of at least 300 N would require a diameter of at least 30 mm). Such a tablet, however, could not be swallowed. The above empirical formula preferably does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468). This means that conventional tablets having a breaking strength well below 200 N may be crushed upon spontaneous chewing, whereas the pharmaceutical dosage forms according to the invention may not.

Still further, when applying a gravitational acceleration of about 9.81 m/s$^2$, 500 N correspond to a gravitational force of more than 50 kg, i.e. the pharmaceutical dosage forms according to the invention can preferably withstand a weight of more than 50 kg without being pulverized.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2005/016313, WO 2005/016314, and WO 2006/082099, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In a preferred embodiment of the invention, the breaking strength is measured by means of a breaking strength tester e.g. Sotax®, type HT100 or type HT1 (Allschwil, Switzerland). Both, the Sotax® HT100 and the Sotax® HT1 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the pharmaceutical dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, in direction of extension $E_1$ the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed, e.g. plastically, when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break (plastic deformation or plastic flow) is preferably to be regarded as having the desired breaking strength in said direction of extension.

It has been surprisingly found, however, that the pharmaceutical dosage forms according to the invention, due to the presence of the physiologically acceptable polymer (B), exhibit mechanical properties that are even superior over the mechanical properties of conventional tamper-resistant dosage forms exhibiting an increased breaking strength such as disclosed in WO 2005/016313, WO 2005/016314, WO 2005/063214, WO 2005/102286, WO 2006/002883, WO 2006/002884, WO 2006/002886, WO 2006/082097, WO 2006/082099, WO 2008/107149, and WO2009/092601. It has been surprisingly found that the mechanical strength of the pharmaceutical dosage forms is increased compared to comparative pharmaceutical dosage forms which have the same composition but where the physiologically acceptable polymer (B) does not comprise anionic functional groups such as hydroxypropylmethyl cellulose.

Said superior mechanical properties seem to basically result in an increased hardness and/or a decreased deformability upon exposure to an external force. In particular, when measuring the breaking strength of the pharmaceutical dosage forms according to the invention by means of a breaking strength tester equipped with plain jaws, the pharmaceutical dosage forms according to the invention preferably do not break, even if the exerted force amounts to 1500 N, i.e. the pharmaceutical dosage forms preferably exhibit a breaking strength of at least 1500 N.

Furthermore, under these circumstances, i.e. when the pharmaceutical dosage forms are subjected to a force of 1500 N in a breaking strength tester (Zwick) equipped with plain jaws, the dimensions of the pharmaceutical dosage forms in direction of the force preferably decrease by not more than 75% or not more than 70% of the original dimensions, more preferably not more than 65% or not more than 60%, still more preferably not more than 55% or not more than 50%, yet more preferably not more than 45% or not more than 40%, even more preferably not more than 35% or not more than 30%, most preferably not more than 25% or not more than 20%, and in particular not more than 15% or not more than 10% of the original dimensions. For example, a pharmaceutical dosage form according to the invention having a height of e.g. 5 mm and being exposed to a force of 1500 N in a breaking strength tester equipped with plain jaws is compressed and deformed to a sample in the course of the measurement, the height of which sample preferably is still at least 65% of 5 mm, i.e. 3.25 mm.

When the pharmaceutical dosage forms are subjected to a force of 1000 N in a breaking strength tester equipped with plain jaws, the dimensions of the pharmaceutical dosage forms in direction of the force preferably decrease by not more than 60% of the original dimensions, more preferably not more than 55%, still more preferably not more than 50%, yet more preferably not more than 45%, even more preferably not more than 40%, most preferably not more than 35%, and in particular not more than 30%, not more than 25%, not more than 20%, not more than 15% or not more than 10% of the original dimensions.

When the pharmaceutical dosage forms are subjected to a force of 800 N in a breaking strength tester equipped with plain jaws, the dimensions of the pharmaceutical dosage forms in direction of the force preferably decrease by not more than 40% of the original dimensions, more preferably not more than 35%, still more preferably not more than 30%, and most preferably not more than 25%, not more than 20%, not more than 15% or not more than 10% of the original dimensions.

The pharmaceutical dosage form according to the invention contains the physiologically acceptable polymer (B), which due to its anionic functional groups preferably is a hydrophilic polymer. Hydrophilic polymers tend to swell rapidly upon contact to an aqueous medium, thereby accelerating the hydration of a matrix in which they are embedded. The pharmaceutical dosage form according to the invention is characterized by such an accelerated hydration process. Surprisingly, however, the release of the pharmacologically active ingredient (A) is not accelerated by this process, but is additionally retarded instead.

The pharmaceutical dosage form according to the invention is further characterized by a hydration process during which the pharmaceutical dosage form forms a water-containing shell (gel) around a dry core in such a way that the core/gel ratio decreases while the volume of the said dosage form does not increase visibly.

This does include slight degrees of volume change, but compared to conventional hydration processes of hydrophilic polymers, which swell upon contact to an aqueous medium, the volume of the pharmaceutical dosage form does substantially not change during the hydration process.

In a preferred embodiment the invention relates to a tamper-resistant pharmaceutical dosage form having a retarded release profile, especially a tamper-resistant oral dosage form having a retarded release profile, particularly a tamper-resistant tablet having a retarded release profile comprising at least one pharmaceutically active ingredient (A) (pharmacologically active compound) with potential for abuse.

The pharmaceutical dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

The present invention also relates to pharmaceutical dosage forms that are obtainable by any of the processes described here below.

In general, the process for the production of the pharmaceutical dosage form according to the invention preferably comprises the following steps:
(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide (C) up to its softening point;
(c) hardening the mixture by applying heat and force, it being possible to supply the heat during and/or before the application of force and the quantity of heat supplied being sufficient to heat the polyalkylene oxide (C) at least up to its softening point; and thereafter allowing the material to cool and removing the force
(d) optionally singulating the hardened mixture;
(e) optionally shaping the pharmaceutical dosage form; and
(f) optionally providing a film coating.

Heat may be supplied directly, e.g. by contact or by means of hot gas such as hot air, or with the assistance of ultrasound; or is indirectly supplied by friction and/or shear. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide (C). However, extrusion at lower temperatures, e.g. ambient temperature, is also possible and may be preferred.

Shaping can be performed, e.g., by means of a tabletting press comprising die and punches of appropriate shape.

A particularly preferred process for the manufacture of the pharmaceutical dosage form of the invention involves hot-melt extrusion. In this process, the pharmaceutical dosage form according to the invention is produced by thermoforming with the assistance of an extruder, preferably without there being any observable consequent discoloration of the extrudate.

This process is characterized in that
a) all components are mixed,
b) the resultant mixture is heated in the extruder at least up to the softening point of the polyalkylene oxide (C) and extruded through the outlet orifice of the extruder by application of force,
c) the still plastic extrudate is singulated and formed into the pharmaceutical dosage form or
d) the cooled and optionally reheated singulated extrudate is formed into the pharmaceutical dosage form.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

The, preferably molten, mixture which has been heated in the extruder at least up to the softening point of polyalkylene oxide (C) is extruded from the extruder through a die with at least one bore.

The process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 30%, i.e. that when using a die with a bore having a diameter of e.g. 6 mm, the extruded strand should have a diameter of not more than 8 mm. More preferably, the expansion of the strand is not more than 25%, still more preferably not more than 20%, most preferably not more than 15% and in particular not more than 10%.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide (C) proceeding in the first zone, which is downstream from a feed zone and optionally mixing zone. The throughput of the mixture is preferably from 1.0 kg to 15 kg/hour. In a preferred embodiment, the throughput is from 1 to 3.5 kg/hour. In another preferred embodiment, the throughput is from 4 to 15 kg/hour.

In a preferred embodiment, the die head pressure is within the range of from 25 to 100 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide (C) and does not rise above a temperature at which the pharmacologically active ingredient (A) to be processed may be damaged. Preferably, the temperature of the mixture to be extruded is adjusted to below 180° C., preferably below 150° C., but at least to the softening temperature of polyalkylene oxide (C). Typical extrusion temperatures are 120° C. and 130° C.

In a preferred embodiment, the extruder torque is within the range of from 30 to 95%. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

Preferably, intermediate or final storage of the optionally singulated extrudate or the final shape of the pharmaceutical dosage form according to the invention is performed under oxygen-free atmosphere which may be achieved, e.g., by means of oxygen-scavengers.

The singulated extrudate may be press-formed into tablets in order to impart the final shape to the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE27 (Leistritz, Nürnberg, Germany), screw diameters of 18 or 27 mm. Screws having eccentric ends may be used. A heatable die with a round bore having a diameter of 7, 8, or 9 mm may be used. The extrusion parameters may be adjusted e.g. to the following values: rotational speed of the screws: 120 Upm; delivery rate2 kg/h for a ZSE 18 or 8 kg/h for a ZSE27; product temperature: in front of die 125° C. and behind die 135° C.; and jacket temperature: 110° C.

Preferably, extrusion is performed by means of twin-screw-extruders or planetary-gear-extruders, twin-screw extruders (co-rotating or contra-rotating) being particularly preferred.

The pharmaceutical dosage form according to the invention is preferably produced by thermoforming with the assistance of an extruder without any observable consequent discoloration of the extrudates.

In order to make the composition of the pharmaceutical dosage form according to the invention thermo-formable, preferably by melt-extrusion, the polyalkylene oxide (C) is preferably contained in excess relative to physiologically acceptable polymer (B). More preferably, the weight ratio of the polyalkylene oxide (C) to the physiologically acceptable polymer (B) is within the range from 10:1 to 1.1:1, still more preferably within the range from 8:1 to 1.5:1 yet more preferably within the range of from 7:1 to 2:1, and most preferably within the range from 6:1 to 2.5:1.

The process for the preparation of the pharmaceutical dosage form according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

A further aspect of the invention relates to the use of a pharmacologically active ingredient (A) for the manufacture of the pharmaceutical dosage form as described above for the treatment of pain.

A further aspect of the invention relates to the use of a pharmaceutical dosage form as described above for avoiding or hindering the abuse of the pharmacologically active ingredient (A) contained therein.

A further aspect of the invention relates to the use of a pharmaceutical dosage form as described above for avoiding or hindering the unintentional overdose of the pharmacologically active ingredient (A) contained therein.

In this regard, the invention also relates to the use of a pharmacologically active ingredient (A) as described above and/or a polyalkylene oxide (C) as described above for the manufacture of the pharmaceutical dosage form according to the invention for the prophylaxis and/or the treatment of a disorder, thereby preventing an overdose of the pharmacologically active ingredient (A), particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active ingredient (A), particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The following examples further illustrate the invention but are not to be construed as limiting its scope:

EXAMPLE 1

Pharmaceutical dosage forms were manufactured from the following compositions (per tablet):

|  | I-1 | | I-2 | | I-3 | | C-1 | |
|---|---|---|---|---|---|---|---|---|
| Composition | [mg] | [wt %] | [mg] | [wt %] | [mg] | [wt %] | [mg] | [wt %] |
| Tramadol HCl | 80.0 | 13.3% | 80.0 | 13.3% | 80.0 | 13.3% | 80.0 | 13.3% |
| Polyethylene oxide 7000000 | 365.8 | 61.0% | 305.8 | 51.0% | 305.8 | 51.0% | 365.8 | 61.0% |
| Carbopol 971P | 60.0 | 10.0% | 120.0 | 20.0% | 60.0 | 10.0% | — | — |
| Hypromellose 100000 | — | — | — | — | 60.0 | 10.0% | 60.0 | 10.0% |
| Macrogol 6000 | 90.0 | 15.0% | 90.0 | 15.0% | 90.0 | 15.0% | 90.0 | 15.0% |
| α-Tocopherol | 1.2 | 0.2% | 1.2 | 0.2% | 1.2 | 0.2% | 1.2 | 0.2% |
| Citric acid (anhydrous) | 3.0 | 0.5% | 3.0 | 0.5% | 3.0 | 0.5% | 3.0 | 0.5% |
| Total weight | 600.0 | | 600.0 | | 600.0 | | — | |

General Procedure:

Polyethylene oxide, α-tocopherol, tramadol hydrochloride, Carbopol 971P, Macrogol 6000 and Hypromellose (in case of inventive example I-3) were weighted and sieved. The powder was mixed and dosed gravimetrically to an extruder. Hot-melt extrusion was performed by means of a twin screw extruder of type Micro 27 GL 40 D (Leistritz, Nürnberg, Germany) that was equipped with a heatable round die having a diameter of 10 mm.

The following additional extrusion conditions depended on the corresponding composition of the extrudate:

|  | I-1 | I-2 | I-3 |
|---|---|---|---|
| Temperature of the melt | 118° C. | 117° C. | 114° C. |
| Power consumption (%) | 69% | 80% | 79% |
| Force (bar) | 43 bar | 56 bar | 47 bar |
| Strand diameter | 11.1 mm | 12.08 mm | 11.2 mm |
| Strand length | 5.3 mm | n.d. | 6.2 mm |

The hot extrudate was cooled on a conveyor belt and the cooled extrusion strand was comminuted to cut pieces weighing 600 mg each. The cut pieces were shaped by means of an excenter press. The tablets of inventive examples I-1, I-2 and I-3 were shaped by means of a tabletting tool with upper punch, lower punch and die for tablets with a 12 mm diameter and a radius of curvature of 9 mm.

The tablets of inventive examples I-1, I-2 and I-3 had the following dimensions (average values n=10):

|  |  | I-1 | I-2 | I-3 |
|---|---|---|---|---|
| Diameter [mm] | Min | 11.48 | 11.16 | 11.64 |
| n = 10 | Max | 12.01 | 11.83 | 11.85 |
|  | ∅ | 11.80 | 11.49 | 11.74 |
| Width [mm] | Min | 5.43 | 5.79 | 6.24 |
| n = 10 | Max | 6.21 | 6.21 | 6.34 |
|  | ∅ | 5.77 | 5.96 | 6.30 |

The breaking strength of the pharmaceutical dosage forms was measured by means of a Zwick Z 2.5 at a constant speed of 10 mm/min. A tablet was regarded as failing the breaking strength test when during the measurement the force dropped below the threshold value of 25% of the maximum force that was observed during the measurement, regardless of whether the dosage form was fractured into separate pieces or not. All values are given as mean of 3 measurements (n=3).

Figure 2:
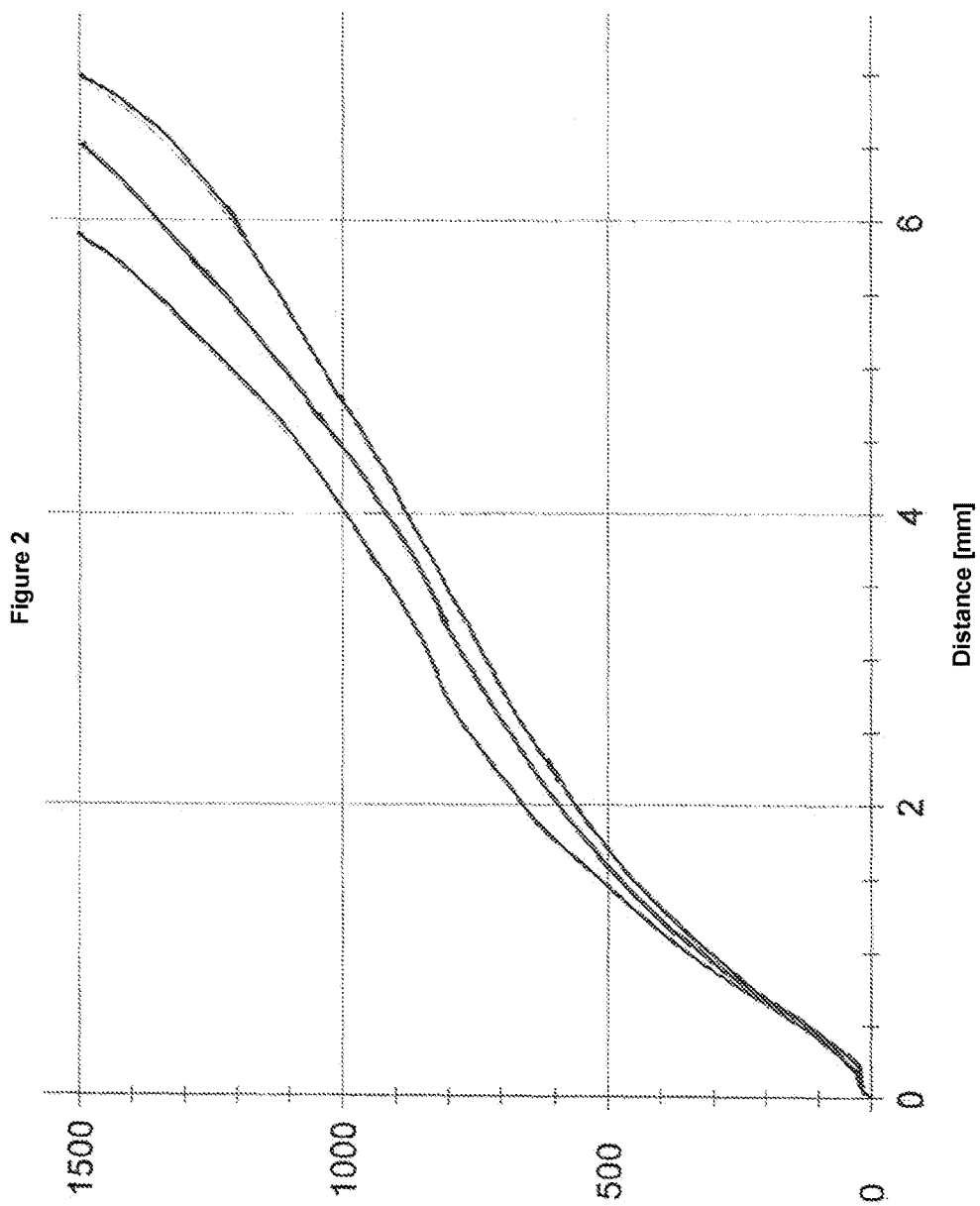
FIG. 2 shows the force-to-distance diagrams of the breaking strength measurements (120 mm/min) of the dosage form according to inventive example I-2 containing 20 wt.-% of Carbopol® 971P as physiologically acceptable polymer (B) and tramadol hydrochloride as ingredient (A).
Figure 3:
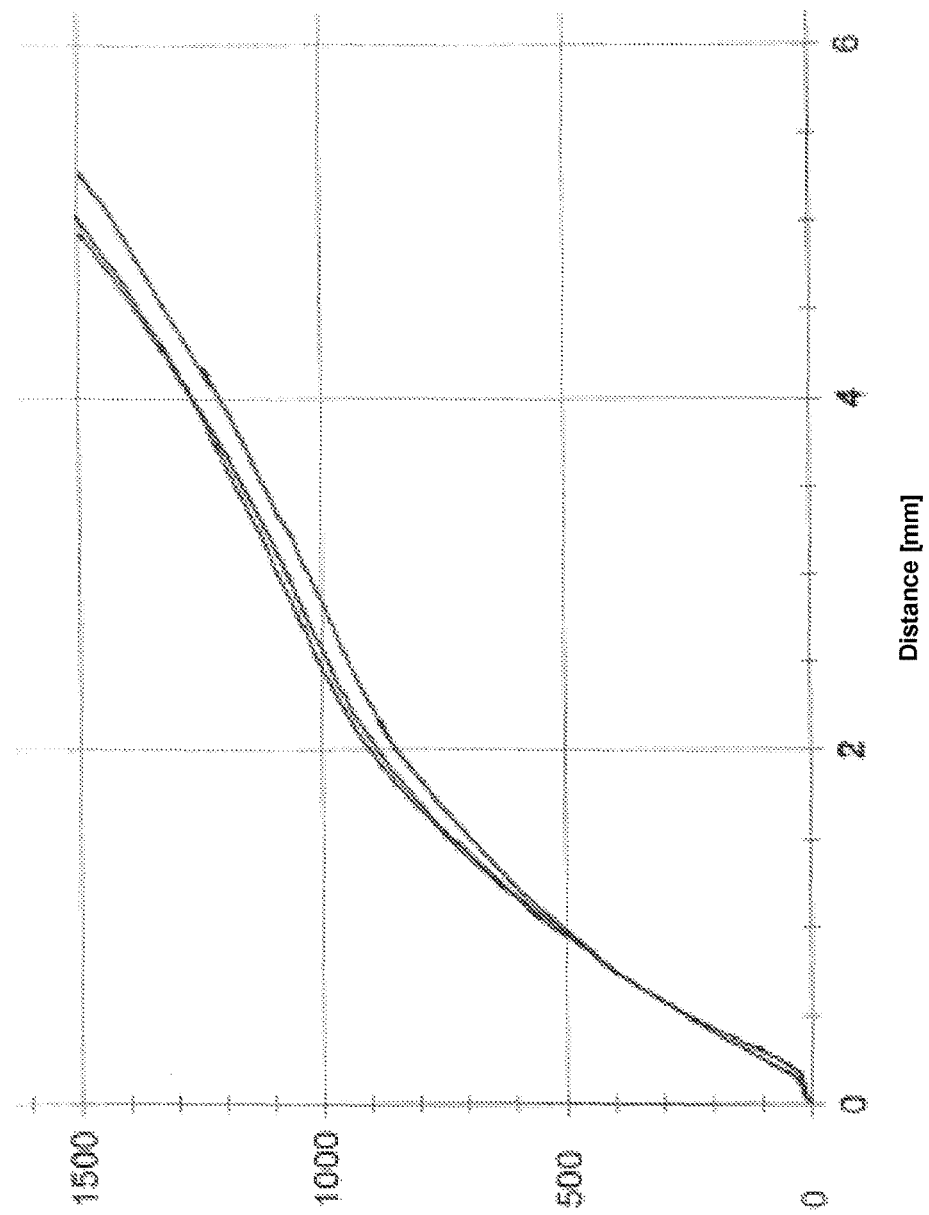
FIG. 3 shows the force-to-distance diagrams of the breaking strength measurements (120 mm/min) of the dosage form according to inventive example I-3 containing 10 wt.-% of Carbopol® 971P as physiologically acceptable polymer (B), 10 wt.-% of HPMC 100000 and tramadol hydrochloride as ingredient (A).
Figure 4:
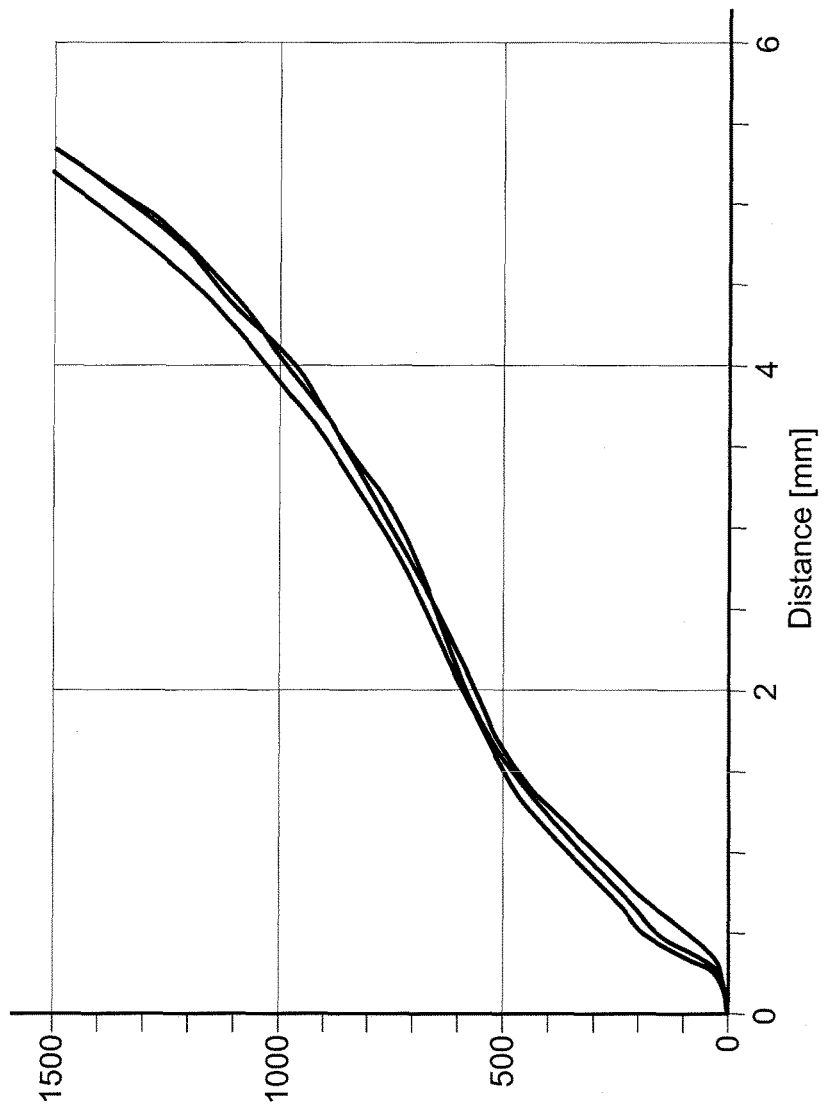
FIG. 4 shows the force-to-distance diagrams of the breaking strength measurements (120 mm/min) of the dosage form according to comparative example C-1.

The results of the breaking strength measurements are depicted for inventive example I-1 in FIG. 1, for inventive example I-2 in FIG. 2, for inventive example I-3 in FIG. 3 and for comparative example C-1 in FIG. 4, respectively. Additionally, the results are summarized in the table here below:

|  | Breaking strength |
|---|---|
| I-1 | >800 N |
| I-2 | >1500 N |
| I-3 | >1500 N |
| C-1 | >1500 N |

It has been surprisingly found that the presence of polymer (B) substantially improves the mechanical strength of the dosage forms according to the invention. In particular, it becomes evident from a comparison of the force-to-distance diagrams (FIGS. 1 to 4) that the dosage forms according to the invention (I-1, I-2 and I-3) are less deformed when being subjected to external forces in the course of the breaking strength measurement than comparative example C-1. For example, when exerting an external force of 800 N (at a constant speed of 120 mm/min in diameter direction) the dosage form according to inventive example I-3 is compressed by about 14%, whereas the dosage form according to comparative example C-1 is compressed by about 39%.

EXAMPLE 2

In accordance with example 1, pharmaceutical dosage forms were manufactured from the following composition (per tablet):

| Composition | I-4 | |
|---|---|---|
| Oxymorphone HCl (anhydrous) | 80.0 mg | 11.1% |
| Polyethylene oxide 7000000 | 395.4 mg | 54.9% |
| Carbopol 971P | 144.0 mg | 20.0% |
| Macrogol 6000 | 95.6 mg | 13.3% |
| α-Tocopherol | 1.4 mg | 0.2% |
| Citric acid (anhydrous) | 3.6 mg | 0.5% |
| Total weight | 720.0 mg | |

Deviating from example 1, extrusion was performed by means of a twin screw extruder of type Micro 27 GL 40 D (Leistritz, Nürnberg, Germany) that was equipped with a heatable round die having a diameter of 8 mm.

The following extrusion conditions depended on the corresponding composition of the extrudate:

| | I-4 |
|---|---|
| Temperature of the melt | 121° C. |
| Power consumption (%) | 79% |
| Force (bar) | 64 bar |
| Strand diameter | 9.0 mm |
| Strand length | 9.5 mm |

The hot extrudate was cooled on a conveyor belt and the cooled extrusion strand was comminuted to cut pieces weighing 720 mg each. The cut pieces were shaped by means of an excenter press. The tablets of inventive examples I-4 were shaped by means of a conventional oblong plunger (9×21 mm).

The tablets of inventive example I-4 had the following dimensions (average values n=10):

| | | I-4 |
|---|---|---|
| Length [mm] | Min | 15.06 |
| n = 10 | Max | 15.65 |
| | Ø | 15.35 |
| Height [mm] | Min | 8.97 |
| n = 10 | Max | 9.11 |
| | Ø | 9.04 |
| Width [mm] | Min | 6.37 |
| n = 10 | Max | 6.97 |
| | Ø | 6.70 |

Figure 5:
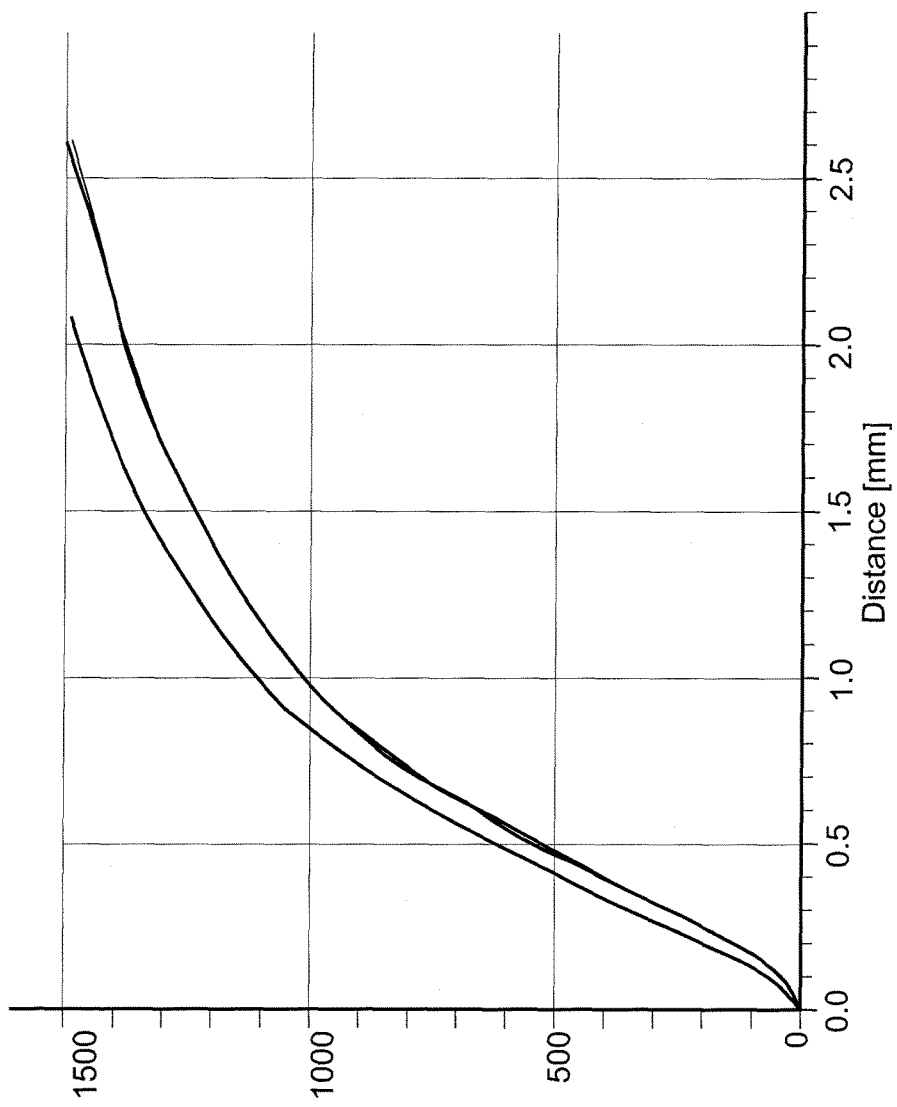
FIG. 5 shows the force-to-distance diagrams of the breaking strength measurements of the dosage form according to inventive example I-4 containing 10 wt.-% of Carbopol® 971P as physiologically acceptable polymer (B) and oxymorphone hydrochloride as ingredient (A).

The breaking strength of the pharmaceutical dosage forms was measured according to example 1. The results of the breaking strength measurements are depicted in FIG. 5.

Surprisingly, the pharmaceutical dosage form of inventive example I-4 was able to withstand a force of 1500 N (n=3) without breaking or being deformed significantly. For example, when exerting an external force of 800 N (at a constant speed of 10 mm/min in longitudinal direction) the dosage form is compressed by only about 5%; and when increasing this external force to 1500 N, the dosage form is compressed to about 15%.

EXAMPLE 3

In accordance with example 1, pharmaceutical dosage forms were manufactured from the following compositions (per tablet):

| Composition [mg] | C-1 | I-5 | I-6 |
|---|---|---|---|
| Tramadol HCl | 80.0 | 80.0 | 80.0 |
| Polyethylene oxide 7000000 | 365.8 | 365.8 | 305.8 |
| Polyethylene glycol 6000 | 90.0 | 90.0 | 90.0 |
| α-Tocopherol | 1.2 | 1.2 | 1.2 |
| Citric acid (anhydrous) | 3.0 | 3.0 | 3.0 |
| HPMC 100000 | 60.0 | — | — |
| Luquasorb B1110 | — | 60.0 | 120.0 |
| Total weight | 600.0 | 600.0 | 600.0 |

The dissolution profile of the tablets was investigated under the following conditions: Paddle apparatus equipped with sinker, 75 rpm, 37±5° C., 600 mL simulated intestinal fluid pH 6.8 (phosphate buffer). The release profile of tramadol was detected spectrometrically at 271 nm.

Figure 6:
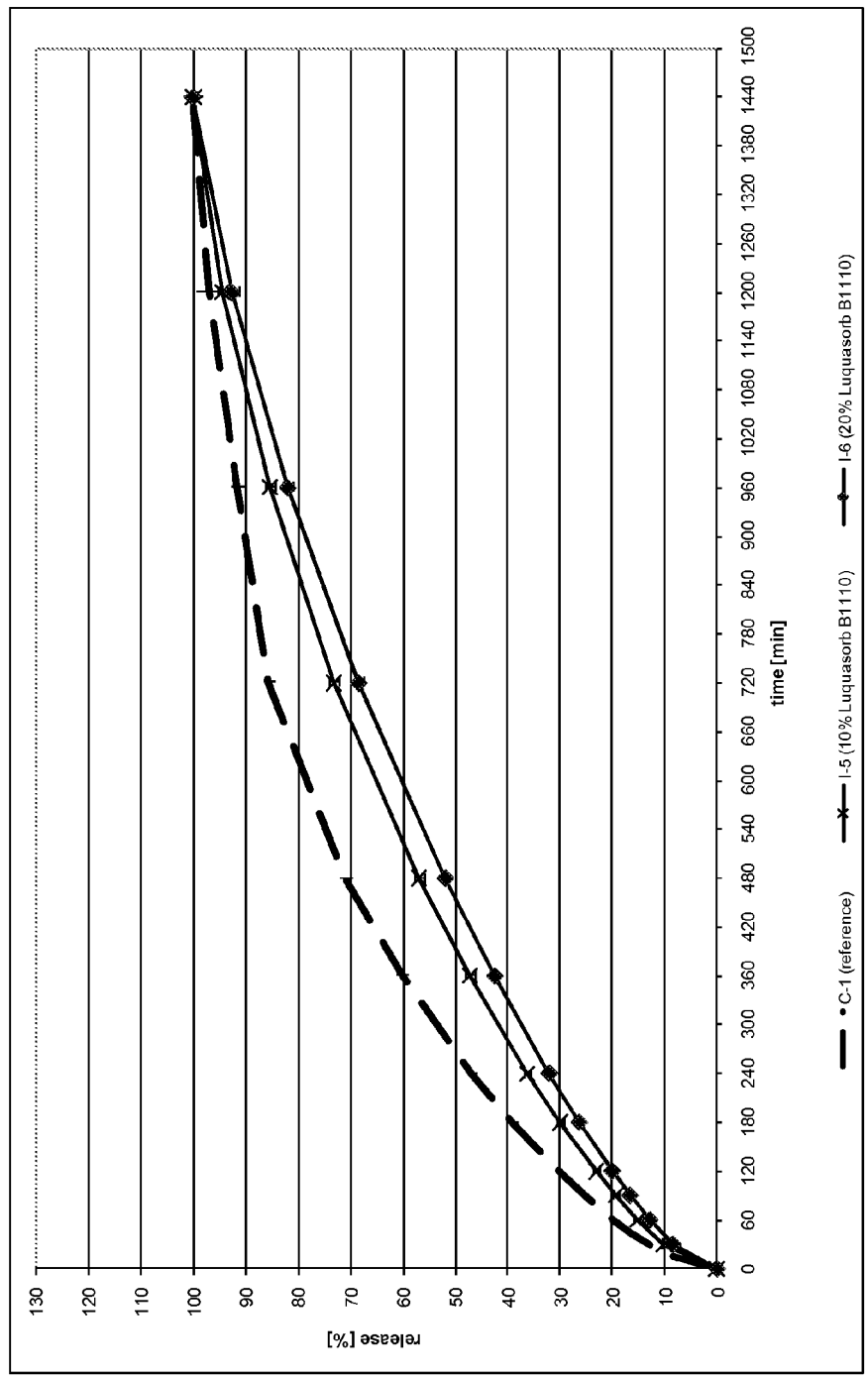
FIG. 6 shows the in vitro release profile of a pharmaceutical dosage forms according to comparative example C-1 and the inventive examples I-5 and I-6, containing different amounts of Luquasorb® B1110 (0 wt.-%, 10 wt.-%, 20 wt.-%) as physiologically acceptable polymer (B).

The results are displayed in FIG. 6. Data were normalized to 100% release after 24 h.

FIG. 6 shows that the release of tramadol from the tablet according to inventive example I-5 (10% Luquasorb) is significantly reduced compared to the release of tramadol from the tablet according to comparative example C-1. It is further reduced when a tablet according to inventive example I-6 (20% Luquasorb) is employed indicating a dependence of the release profile on the content of the superabsorbent Luquasorb.

The swelling behaviors of inventive examples I-5, I-6 and comparative example C-1 was investigated next under the following conditions: A beaker (100 mL) was placed onto a mm-graduated scale and a tablet of each batch was added at room temperature. A photograph of the tablet was taken every 45 min.

Figure 7:
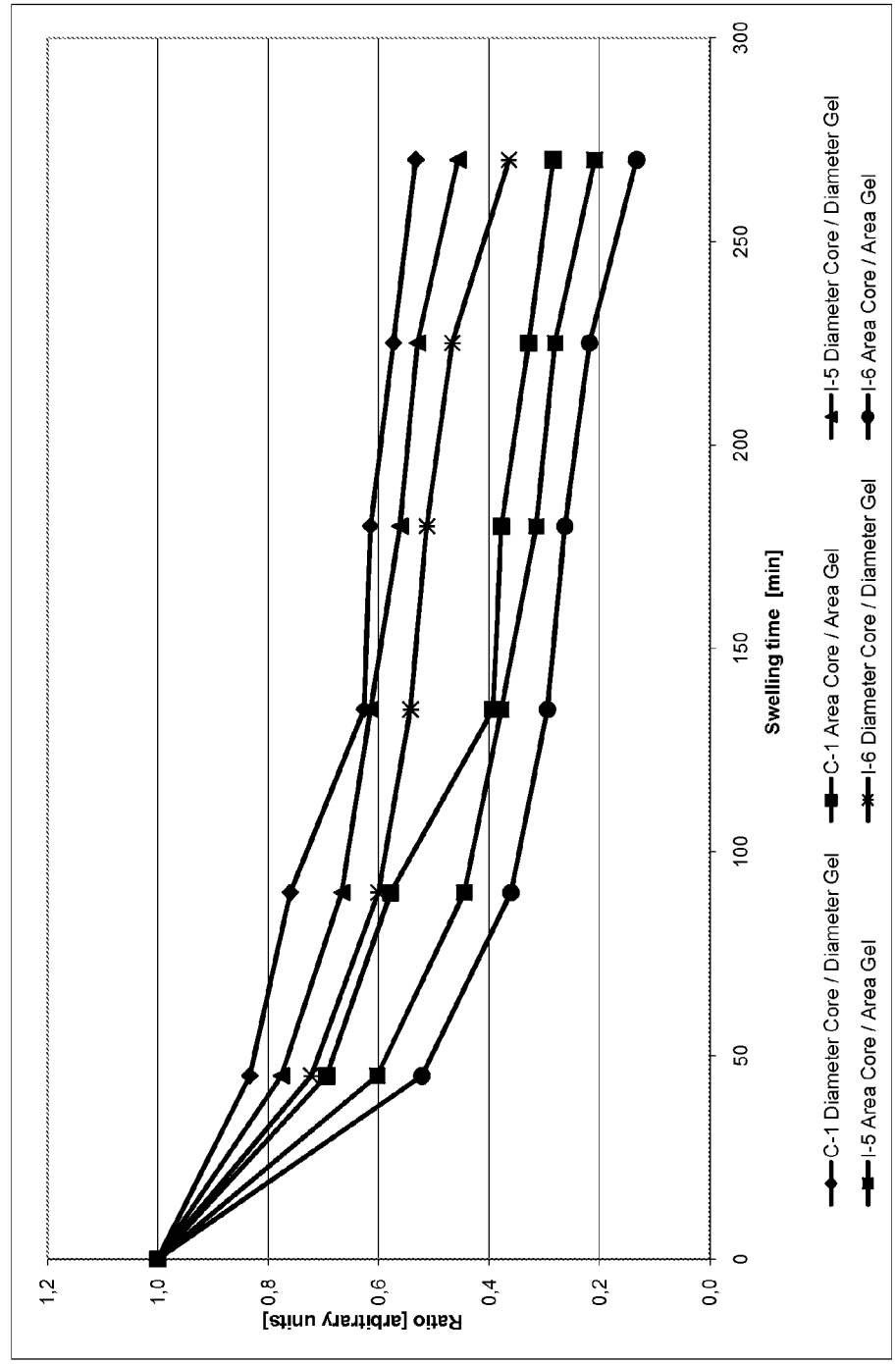
FIG. 7 shows the area core/area gel and diameter core/diameter gel ratios for the swelling experiments of the dosage form according to comparative example C-1 and inventive example I-5 and I-6.

The results of the swelling behavior experiment are listed in the table below and depicted in FIG. 7:

| Diameter | C-1 | | | I-5 | | | I-6 | | |
|---|---|---|---|---|---|---|---|---|---|
| [mm] | Core | Gel | Core/Gel | Core | Gel | Core/Gel | Core | Gel | Core/Gel |
| 45.0 min | 4.5 | 5.4 | 0.8 | 5.2 | 6.7 | 0.8 | 5.2 | 7.2 | 0.7 |
| 90.0 min | 5.7 | 7.5 | 0.8 | 5.0 | 7.5 | 0.7 | 4.5 | 7.5 | 0.6 |
| 135.0 min | 5.2 | 8.3 | 0.6 | 5.1 | 8.3 | 0.6 | 4.5 | 8.3 | 0.5 |
| 180.0 min | 5.1 | 8.3 | 0.6 | 4.6 | 8.2 | 0.6 | 4.2 | 8.2 | 0.5 |
| 225.0 min | 5.5 | 9.6 | 0.6 | 4.5 | 8.5 | 0.5 | 4.9 | 10.5 | 0.5 |
| 270.0 min | 5.7 | 10.7 | 0.5 | 4.7 | 10.3 | 0.5 | 4.0 | 11.0 | 0.4 |

These results show that the ratio between the diameter of core and gel according to inventive examples I-5 and I-6 is decreased faster compared to the ratio between the diameter of core and gel according to example C-1, indicating a faster hydration of the tablet in presence of Luquasorb. At the same time the volume of the tablet according to inventive examples I-5 and I-6 is not increased compared to the volume of the tablet according to comparative example C-1.

EXAMPLE 4

In accordance with Example 1, pharmaceutical dosage forms were manufactured from the following compositions (per tablet):

| Composition [mg] | C-1 | I-7 | I-8 | I-9 |
|---|---|---|---|---|
| Tramadol HCl | 80.0 | 80.0 | 80.0 | 80.0 |
| Polyethylene oxide 7000000 | 365.8 | 365.8 | 305.8 | 305.8 |
| Polyethylene glycol 6000 | 90.0 | 90.0 | 90.0 | 90.0 |
| α-Tocopherol | 1.2 | 1.2 | 1.2 | 1.2 |
| Citric acid (anhydrous) | 3.0 | 3.0 | 3.0 | 3.0 |
| HPMC 100000 | 60.0 | — | — | 60.0 |
| Carbopol 971P | — | 60.0 | 120.0 | 60.0 |
| Total weight | 600.0 | 600.0 | 600.0 | 600.0 |

The dissolution profile of the tablets was investigated according to example 3 (at pH 6.8). Additionally, the dissolution profile of the tablets was investigated at pH 1.2.

Figure 8:
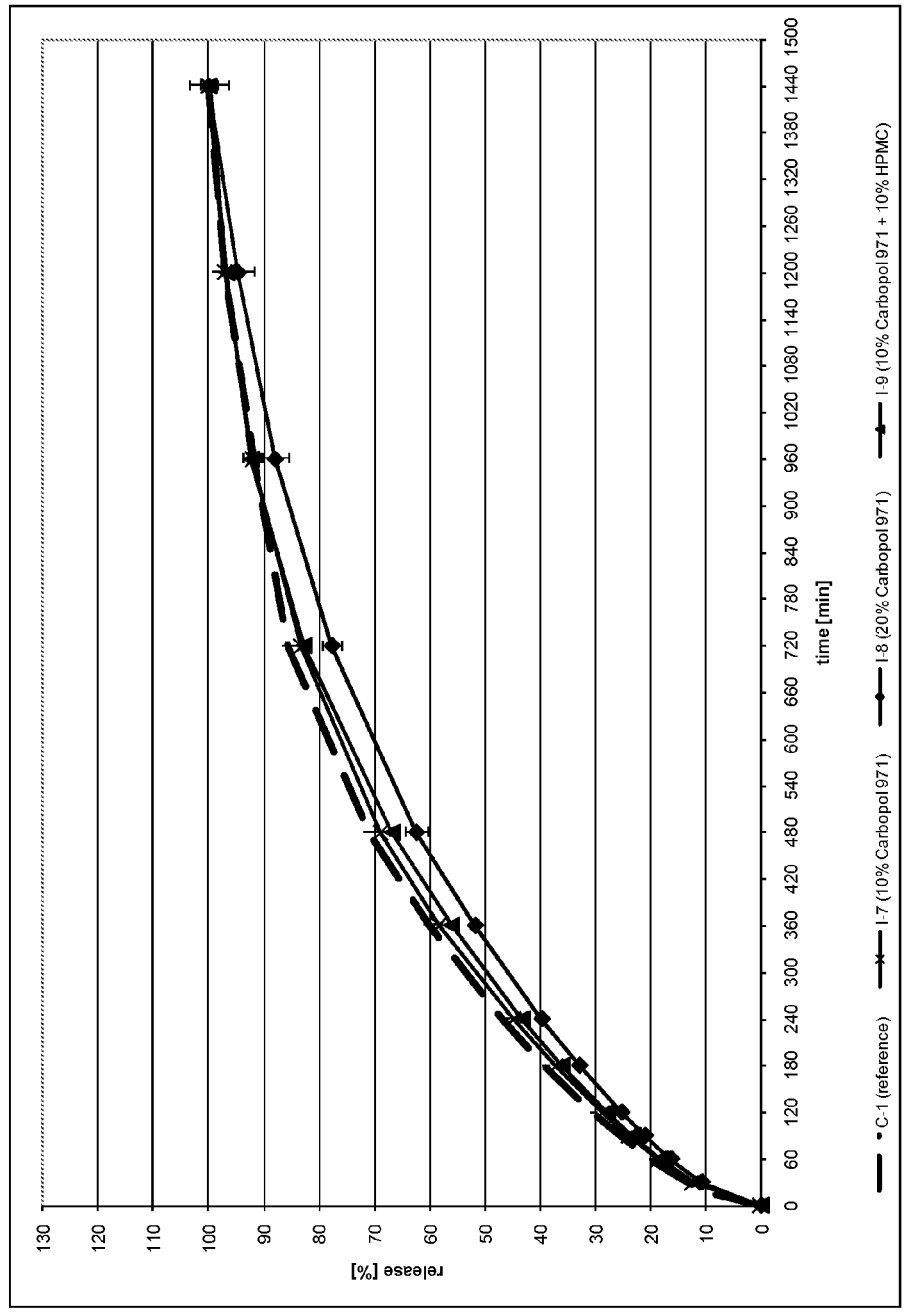
FIG. 8 shows the in vitro release profile of a pharmaceutical dosage forms according to comparative example C-1 and the inventive examples I-7, I-8 and I-9, containing different amounts of Carbopol® 971P (0 wt.-%, 10 wt.-%, 20 wt.-%, 10 wt.-%) as physiologically acceptable polymer (B).
Figure 9:
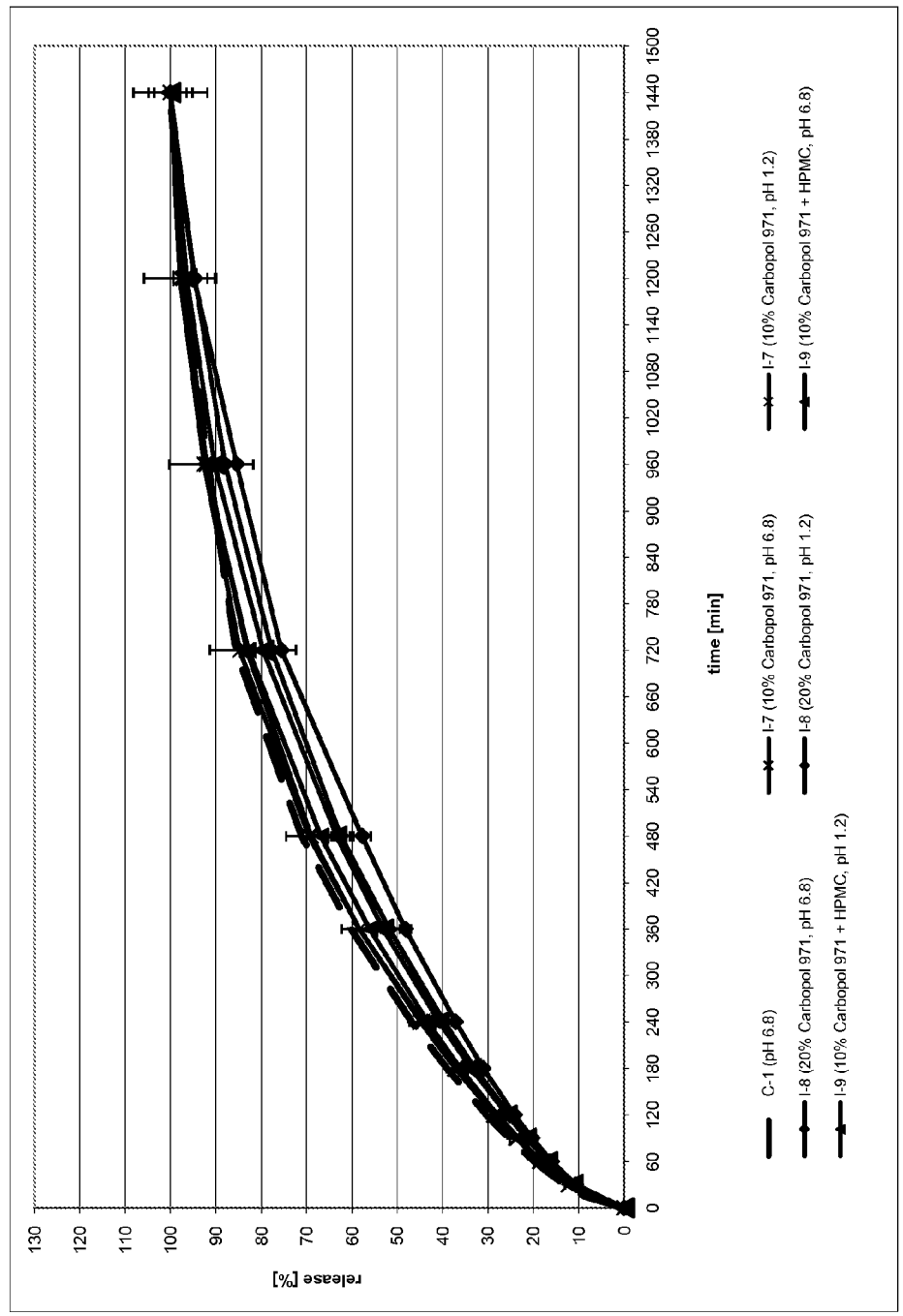
FIG. 9 shows the in vitro release profile of pharmaceutical dosage forms according to comparative example C-1 and the inventive examples I-7, I-8 and I-9 depending on the pH value (for pH 1.2 and pH 6.8).

The results are displayed in FIGS. 8 and 9.

FIG. 8 shows that the release of tramadol from the tablet according to inventive examples I-7 (10% Carbopol 971) is reduced compared to the release profile of the tablet according to comparative example C-1. It is further reduced when a tablet according to inventive example I-8 (20% Carbopol 971) is employed indicating a dependence of the release profile on the content of Carbopol. FIG. 8 also shows that the release profile of a tablet according to inventive example I-9 (10% Carbopol 971, 10% HPMC 10000) is comparable to the release profile of a tablet according to inventive example I-7 (10% Carbopol 971).

FIG. 9 shows that the release profile of the tablet of each inventive example at pH 6.8 is comparable to the release profile of the tablet of the same inventive example at pH 1.2, i.e. that the release profile does not depend on the pH of the release medium.

EXAMPLE 5

In accordance with Example 1, pharmaceutical dosage forms were manufactured from the following compositions (per tablet):

| Composition [mg] | C-1 | C-2 | C-3 |
|---|---|---|---|
| Tramadol HCl | 80.0 | 80.0 | 80.0 |
| Polyethylene oxide 7000000 | 365.8 | 365.8 | 305.8 |
| Polyethylene glycol 6000 | 90.0 | 90.0 | 90.0 |
| α-Tocopherol | 1.2 | 1.2 | 1.2 |
| Citric acid (anhydrous) | 3.0 | 3.0 | 3.0 |
| HPMC 100000 | 60.0 | — | — |
| Povidon (Kollidon 90 F, BASF) | — | 60.0 | 120.0 |
| Total weight | 600.0 | 600.0 | 600.0 |

The dissolution profile of the tablets was investigated according to example 3.

Figure 10:
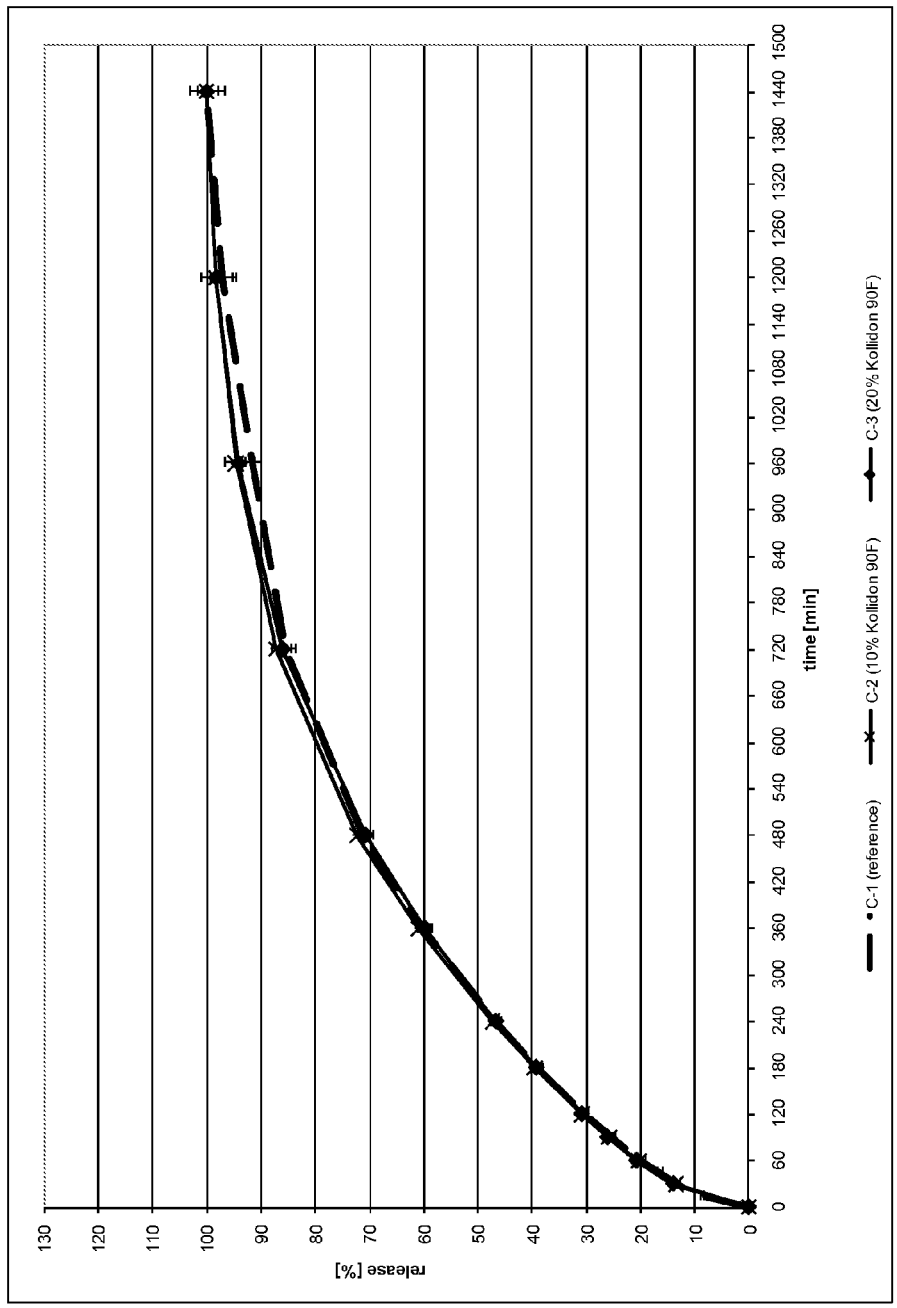
FIG. 10 shows the in vitro release profile of pharmaceutical dosage forms according to comparative examples C-1, C-2 and C-3, containing different amounts of the disintegrant Kollidon® (0 wt.-%, 10 wt.-%, 20 wt.-%).

The results are displayed in FIG. 10.

FIG. 10 shows that the release profiles of the tablets according to comparative examples C-2 (10% Kollidon 90F) and C-3 (20% Kollidon 90F) are comparable to the release profile of a tablet according to comparative example C-1, i.e. that the presence of the disintegrant Kollidon does not influence the release profile.

EXAMPLE 6

In accordance with Example 1, pharmaceutical dosage forms were manufactured from the following compositions (per tablet):

| Composition [mg] | C-1 | C-4 | C-5 |
|---|---|---|---|
| Tramadol HCl | 80.0 | 80.0 | 80.0 |
| Polyethylene oxide 7000000 | 365.8 | 365.8 | 305.8 |
| Polyethylene glycol 6000 | 90.0 | 90.0 | 90.0 |
| α-Tocopherol | 1.2 | 1.2 | 1.2 |
| Citric acid (anhydrous) | 3.0 | 3.0 | 3.0 |
| HPMC 100000 | 60.0 | — | — |
| Calcium hydrogen phosphate dihydrate | — | 60.0 | 120.0 |
| Total weight | 600.0 | 600.0 | 600.0 |

The dissolution profile of the tablets was investigated according to example 3.

Figure 11:
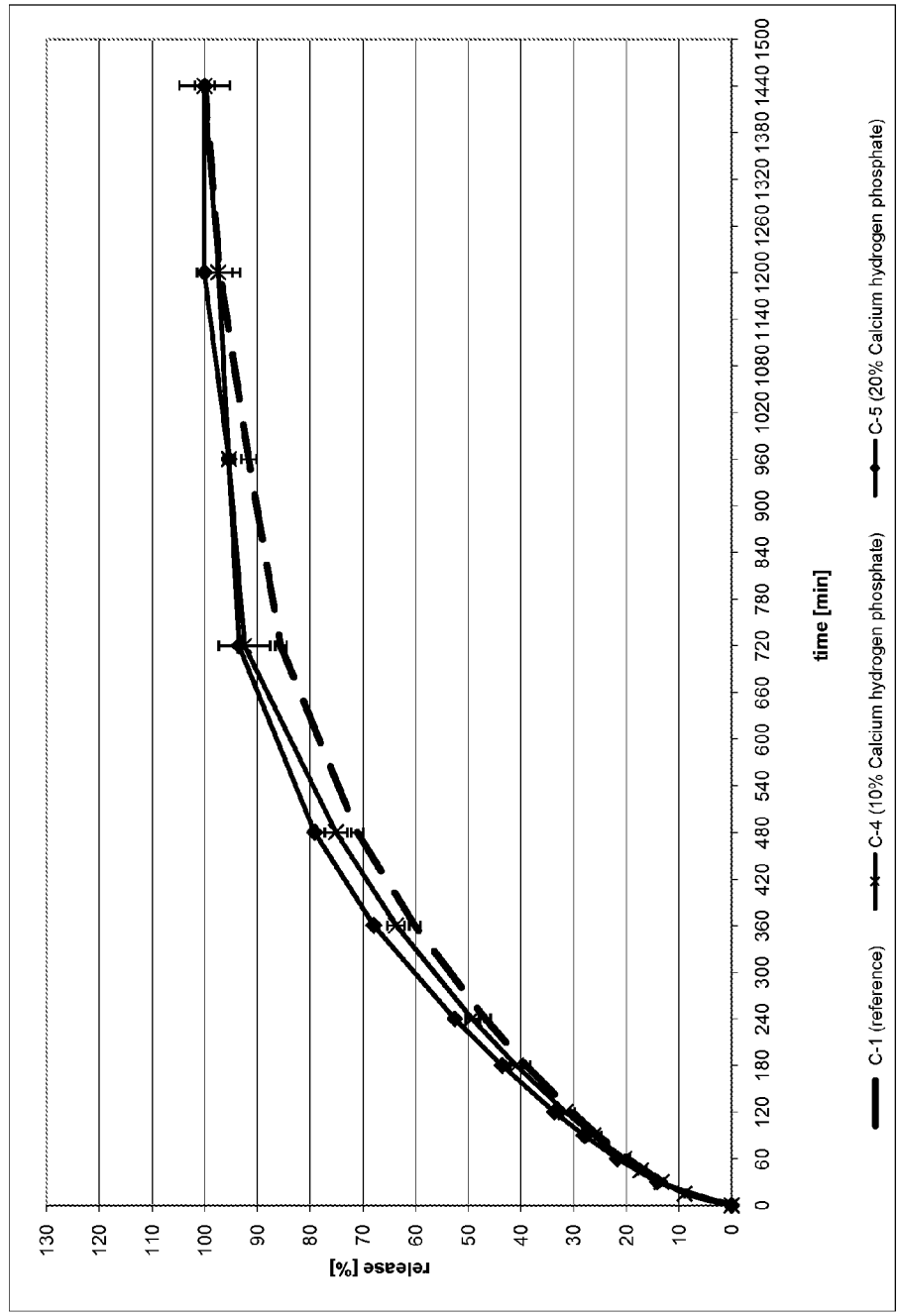
FIG. 11 shows the in vitro release profile of a pharmaceutical dosage form according to comparative examples C-1, C-4 and C-5, containing different amounts of the disintegrant calcium hydrogen phosphate dihydrate (0 wt.-%, 10 wt.-%, 20 wt.-%).

The results are displayed in FIG. 11.

FIG. 11 shows that the release profiles of the tablets according to comparative examples C-4 (10% Calcium hydrogen phosphate) and C-5 (20% Calcium hydrogen phosphate) are comparable to the release profile of a tablet according to comparative example C-1, i.e. that the presence of the disintegrant calcium hydrogen phosphate does not influence the release profile.

EXAMPLE 7

In accordance with Example 1, pharmaceutical dosage forms were manufactured from the following compositions (per tablet):

| Composition [%] | I-10 | I-11 | I-12 | I-13 | I-14 | I-15 | I-16 | I-17 | C-6 |
|---|---|---|---|---|---|---|---|---|---|
| Tramadol HCl | 13.3 | 13.3 | 13.3 | 13.3 | 13.3 | 13.3 | 13.3 | 13.3 | 13.3 |
| Polyethylene oxide $7 \cdot 10^6$ | 44.8 | 44.8 | 44.8 | 44.8 | 44.8 | 44.8 | 44.8 | 44.8 | 61.7 |
| Macrogol 6000 | 11.2 | 11.2 | 11.2 | 11.2 | 11.2 | 11.2 | 11.2 | 11.2 | 15.0 |
| α-Tocopherol | 0.2 | 0.2 | 0.2 | 0.2 | 0.2 | 0.2 | 0.2 | 0.2 | — |
| Citric acid (anhydrous) | 0.5 | 0.5 | 0.5 | 0.5 | 0.5 | 0.5 | 0.5 | 0.5 | — |
| HPMC 100000 | 10.0 | 10.0 | 10.0 | 10.0 | 10.0 | 10.0 | 10.0 | 10.0 | 10.0 |
| Carbopol 934 NF | 20.0 | — | — | — | — | — | — | — | — |
| Carbopol 974P NF | — | 20.0 | — | — | — | — | — | — | — |
| Carbopol 980 NF | — | — | 20.0 | — | — | — | — | — | — |
| Carbopol 981 NF | — | — | — | 20.0 | — | — | — | — | — |
| Carbopol ETD 2020 NF | — | — | — | — | 20.0 | — | — | — | — |
| Carbopol 71G NF | — | — | — | — | — | 20.0 | — | — | — |
| Carbopol Ultrez 10 | — | — | — | — | — | — | 20.0 | — | — |
| Polycarbophil Noveon ® | — | — | — | — | — | — | — | 20.0 | — |

Carbopol 934 NF, Carbopol 974P NF, Carbopol 980 NF, Carbopol 981 NF, and Carbopol 71G NF are homopolymers, namely polymers of acrylic acid crosslinked with allyl sucrose or allyl pentaerythritol. Carbopol ETD 2020 NF and Carbopol Ultrez 10 are interpolymers, namely a carbomer hompolymer or copolymer that contains a block copolymer of polyethylene glycol and a long chain alkyl acid ester. Polycarbophil is a high molecular weight acrylic acid polymer crosslinked with divinyl glycol.

The tablets of inventive examples I-10 to I-15 had the following dimensions (average values n=10):

|  |  | I-10 | I-11 | I-12 | I-13 | I-14 | I-15 | I-16 | I-17 | C-6 |
|---|---|---|---|---|---|---|---|---|---|---|
| Weight | Min | 608 | 581 | 582 | 586 | 583 | 590 | 583 | 582 | 595 |
| [mg] | Max | 619 | 611 | 609 | 609 | 606 | 623 | 611 | 594 | 610 |
| n = 10 | Ø | 613 | 596 | 596 | 595 | 598 | 603 | 592 | 586 | 603 |
| Diameter | Min | 10.92 | 11.29 | 11.56 | 11.06 | 10.88 | 11.49 | 11.55 | 11.74 | 11.63 |
| [mm] | Max | 11.08 | 11.61 | 11.93 | 11.28 | 11.36 | 11.67 | 11.86 | 12.15 | 11.79 |
| n = 10 | Ø | 10.99 | 11.45 | 11.74 | 11.18 | 11.18 | 11.55 | 11.67 | 11.89 | 11.69 |
| Width | Min | 5.58 | 5.04 | 4.97 | 5.36 | 5.64 | 5.81 | 5.59 | 5.36 | 6.43 |
| [mm] | Max | 5.77 | 5.29 | 5.26 | 5.55 | 5.93 | 6.20 | 6.20 | 5.72 | 6.58 |
| n = 10 | Ø | 5.69 | 5.17 | 5.13 | 5.47 | 5.82 | 5.98 | 5.76 | 5.53 | 6.53 |

The breaking strength of the pharmaceutical dosage forms was measured by means of a Sotax® HT100 at a constant speed of 120 mm/min. A tablet was regarded as failing the breaking strength test when during the measurement the force dropped below the threshold value of 25% of the maximum force that was observed during the measurement, regardless of whether the dosage form was fractured into separate pieces or not. All values are given as mean of 10 measurements (n=10).

All tablets of inventive examples I-10 to I-1-17 were able to withstand a force of 1000 N without breaking or being deformed significantly.

The dissolution profile of the tablets was investigated according to example 3 (at pH 6.8, n=3).

The results are displayed in FIG. 12 and summarized in the table here below.

| Dissolution [%] | I-10 | I-11 | I-12 | I-13 | I-14 | I-15 | I-16 | I-17 | C-6 |
|---|---|---|---|---|---|---|---|---|---|
| after 60 min | 18 | 18 | 17 | 23 | 19 | 18 | 18 | 17 | 24 |
| 120 min | 27 | 29 | 26 | 35 | 29 | 28 | 26 | 25 | 38 |
| 480 min | 57 | 66 | 57 | 74 | 67 | 64 | 59 | 59 | 89 |
| 720 min | 70 | 81 | 73 | 89 | 84 | 81 | 74 | 74 | 102 |
| 1440 min | 90 | 106 | 90 | 105 | 105 | 115 | 96 | 94 | 105 |

Figure 12:
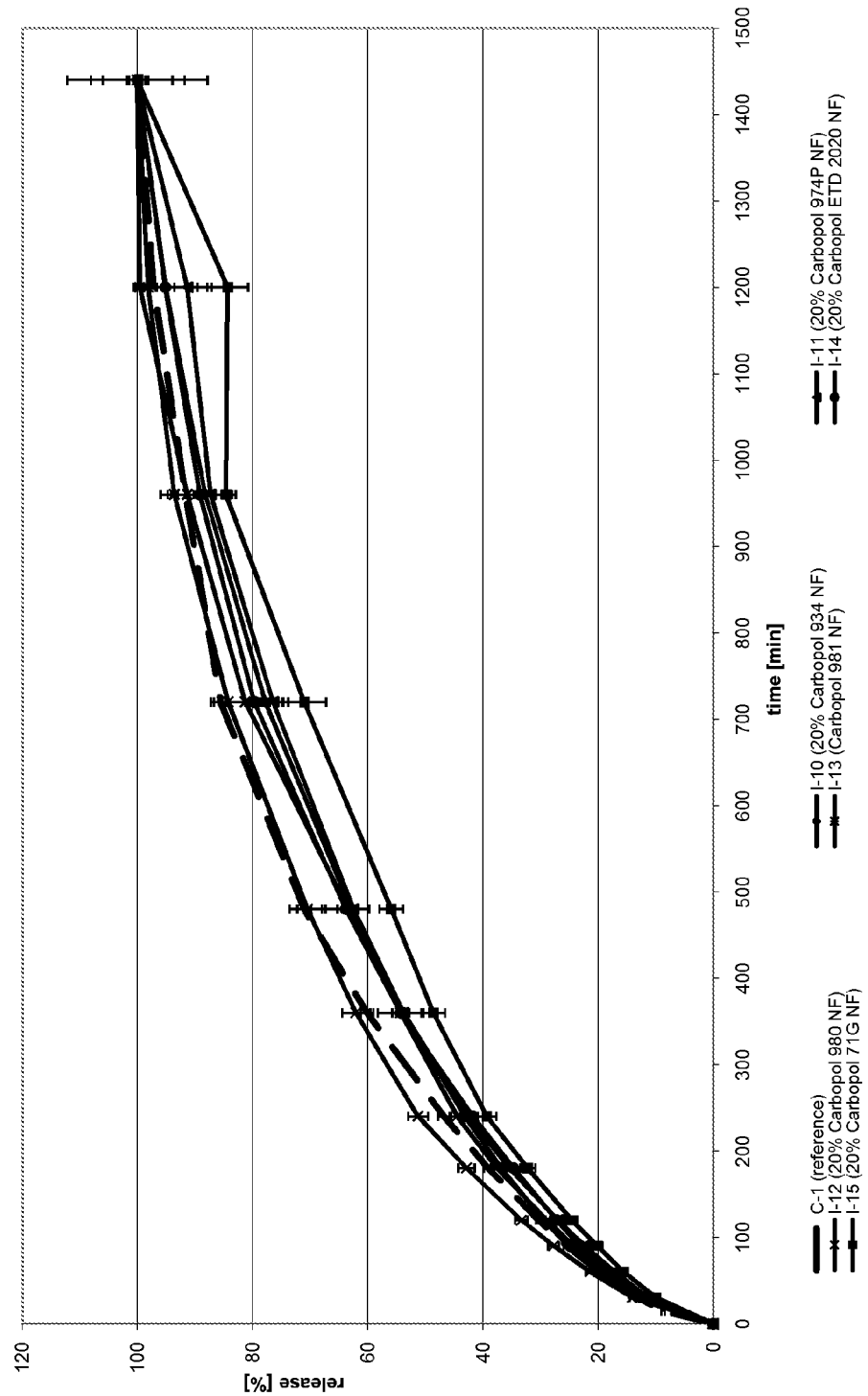
FIG. 12 shows the in vitro release profile of pharmaceutical dosage forms according to comparative example C-1 and the inventive examples I-10 to I-15, containing different types of Carbopol polymers.

FIG. 12 shows that the release of tramadol from the tablets according to inventive examples I-10, I-11, I-12, I-14 and I-15 (containing different types of Carbopol polymers) is reduced compared to the release profile of the tablet according to comparative example C-1 and C-6.

The tablets were cut on a material tester (Zwick Roell) equipped with a cutting blade no. 106 SICURI (Martor). The cutting blade was mounted in an individually designed adapter to achieve optimal guidance of the cutting blade through the tablet (central) and optimal monitoring of measurement. For protecting the force sensor, the cutting process and the measurement were interrupted once the force had dropped by 200 N relative to the measured maximum force.

Figure 13E:
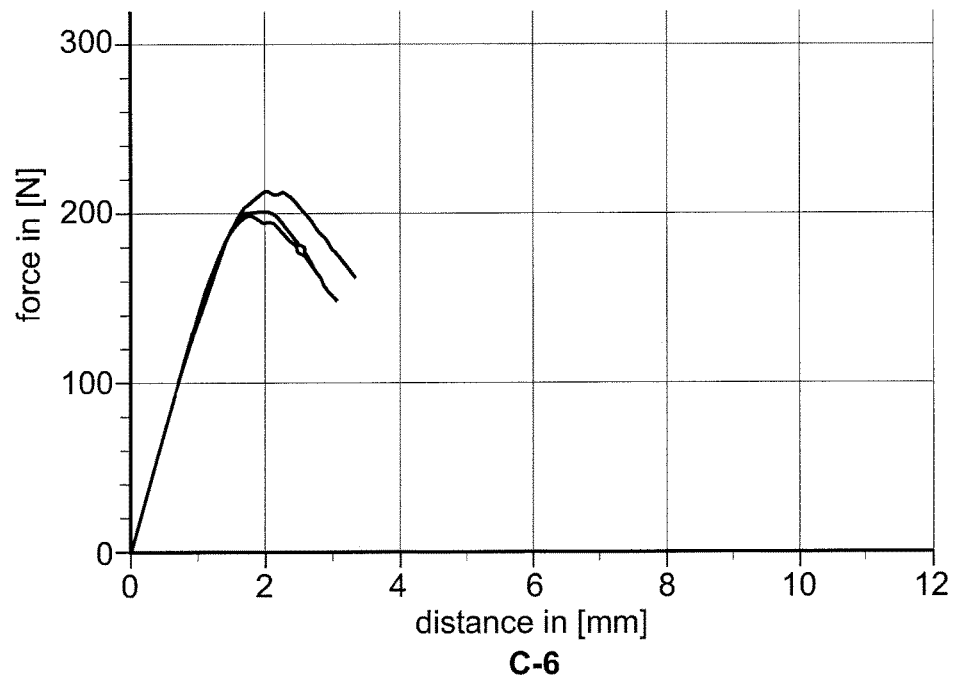
FIG. 13 (A to E) show the force-to-distance diagrams when subjecting the dosage forms according to inventive examples I-10 to I-17 and comparative example C-6 to a cut resistance test.

The results are shown in FIGS. 13 A to 13 E.

EXAMPLE 8

In accordance with Example 1, pharmaceutical dosage forms were manufactured from the following compositions (per tablet):

| Composition [%] | I-15 | I-18 | I-19 | I-20 | I-21 | I-22 |
|---|---|---|---|---|---|---|
| Tramadol HCl | 13.3 | 13.3 | 13.3 | 13.3 | 13.3 | 13.3 |
| Polyethylene oxide 7000000 | 44.8 | 44.8 | 44.8 | 44.8 | 44.8 | 44.8 |
| Macrogol 6000 | 11.2 | 11.2 | 11.2 | 11.2 | 11.2 | 11.2 |
| α-Tocopherol | 0.2 | 0.2 | 0.2 | 0.2 | 0.2 | 0.2 |
| Citric acid (anhydrous) | 0.5 | 0.5 | 0.5 | 0.5 | 0.5 | 0.5 |
| Carbopol 71G | 20.0 | 20.0 | 20.0 | 20.0 | 20.0 | 20.0 |
| HPMC 100000 | 10.0 | — | — | — | — | — |
| Soluplus | — | 10.0 | — | — | — | — |
| Magnesiumstearat | — | — | 10.0 | — | — | — |
| Glycerolmonostearat | — | — | — | 10.0 | — | — |
| Glycerolbehenat (Compritol 888) | — | — | — | — | 10.0 | — |
| Polyethylenoxid 600000 | — | — | — | — | — | 10.0 |

The tablets of inventive examples I-15 and I-18 to I-22 had the following dimensions (average values n=10):

|  |  | I-15 | I-18 | I-19 | I-20 | I-21 | I-22 |
|---|---|---|---|---|---|---|---|
| Weight [mg] n = 10 | Min | 590 | 575 | 584 | 577 | 579 | 577 |
|  | Max | 623 | 634 | 616 | 616 | 627 | 629 |
|  | Ø | 603 | 599 | 602 | 599 | 599 | 598 |
| Diameter [mm] n = 10 | Min | 11.49 | 11.79 | 11.88 | 12.00 | 12.02 | 12.00 |
|  | Max | 11.67 | 11.99 | 11.95 | 12.50 | 12.19 | 12.08 |
|  | Ø | 11.55 | 11.90 | 11.91 | 12.22 | 12.08 | 12.04 |
| Width [mm] n = 10 | Min | 5.81 | 5.83 | 6.28 | 4.95 | 4.93 | 5.32 |
|  | Max | 6.20 | 6.15 | 6.43 | 5.51 | 5.29 | 6.21 |
|  | Ø | 5.98 | 5.99 | 6.34 | 5.24 | 5.15 | 5.73 |

The breaking strength of the pharmaceutical dosage forms was measured according to Example 7. The results are summarized in the table here below:

|  | Breaking strength |
|---|---|
| I-15 | ≥1000 N |
| I-18 | ≥1000 N |
| I-19 | ≥1000 N |
| I-20 | ≥1000 N |
| I-21 | ≥1000 N |
| I-22 | approx. 988 N |

The dissolution profile of the tablets was investigated according to example 3 (at pH 6.8, n=3).

The results are summarized in the table here below.

| Dissolution [%] | I-15 | I-18 | I-19 | I-20 | I-21 | I-22 |
|---|---|---|---|---|---|---|
| after 60 min | 18 | 17 | 15 | 18 | 15 | 19 |
| 120 min | 28 | 27 | 22 | 27 | 23 | 29 |
| 480 min | 64 | 61 | 49 | 62 | 55 | 72 |
| 720 min | 81 | 75 | 63 | 81 | 67 | 89 |
| 1440 min | 115 | 90 | 88 | 103 | 79 | 104 |

The invention claimed is:

1. A pharmaceutical dosage form comprising:
   a pharmacologically active ingredient (A) selected from the group consisting of opioids;
   a physiologically acceptable polymer (B) selected from the group consisting of: (i) optionally cross-linked homopolymers of acrylic acid; (ii) optionally cross-linked copolymers of acrylic acid and $C_{10-30}$-alkyl acrylates; and (iii) interpolymers of (a) or (b) each taken with (c), wherein (a) is an optionally crosslinked homopolymer of acrylic acid, (b) is an optionally crosslinked copolymer of acrylic acid and $C_{10-30}$-alkyl acrylate, and (c) is a block copolymer of polyethylene glycol and a long chain alkyl acid;
   a polyalkylene oxide (C) having a weight average molecular weight of at least 200,000 g/mol, wherein the content of the polyalkylene oxide (C) is at least 20 wt.-%, based on the total weight of the dosage form;
   wherein the pharmacologically active ingredient (A) is present in a controlled-release matrix comprising the polymer (B) and the polyalkylene oxide (C);
   wherein the dosage form is thermoformed; and
   wherein the dosage form exhibits a breaking strength of at least 500 N.

2. The pharmaceutical dosage form according to claim 1, wherein the monomer composition further comprises a cross-linking agent.

3. The pharmaceutical dosage form according to claim 2, wherein the cross-linking agent is selected from the group consisting of allyl sucrose, allyl pentaerythritol, divinyl glycol, divinyl polyethylene glycol and (meth)acrylic acid esters of diols.

4. The pharmaceutical dosage form according to claim 1, wherein the relative weight ratio of the polyalkylene oxide (C) to the physiologically acceptable polymer (B) is within the range of from 8:1 to 1.5:1.

5. The pharmaceutical dosage form according to claim 1, wherein the polyalkylene oxide (C) is a polyethylene oxide.

6. Pharmaceutical dosage form according to claim 5, wherein the polyethylene oxide (C) has a molecular weight of about 500,000 g/mol to about 15,000,000 g/mol.

7. Pharmaceutical dosage form according to claim 1, which has been prepared by melt-extrusion.

8. Pharmaceutical dosage form according to claim 1, which further comprises polyethylene glycol.

9. The pharmaceutical dosage form according to claim 1, which is adapted for administration once-daily, twice daily or thrice-daily.

10. Pharmaceutical dosage form according to claim 1, which is a tablet.

* * * * *